US010661453B2

(12) United States Patent
Koenig et al.

(10) Patent No.: US 10,661,453 B2
(45) Date of Patent: May 26, 2020

(54) ROBOTIC ARMS

(71) Applicant: Verb Surgical Inc., Mountain View, CA (US)

(72) Inventors: Karen Shakespear Koenig, San Jose, CA (US); Pablo E. Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 366 days.

(21) Appl. No.: 15/706,536

(22) Filed: Sep. 15, 2017

(65) Prior Publication Data

US 2018/0079090 A1    Mar. 22, 2018

Related U.S. Application Data

(60) Provisional application No. 62/395,704, filed on Sep. 16, 2016.

(51) Int. Cl.
*B25J 18/04* (2006.01)
*A61B 34/30* (2016.01)
(Continued)

(52) U.S. Cl.
CPC ........... *B25J 18/04* (2013.01); *A61B 1/00149* (2013.01); *A61B 34/30* (2016.02); *A61B 34/35* (2016.02);
(Continued)

(58) Field of Classification Search
CPC .......... A61B 1/00149; A61B 2034/301; A61B 2034/302; A61B 2034/303;
(Continued)

(56) References Cited

U.S. PATENT DOCUMENTS 2,212,823 A    8/1940 Jan Bulk
4,568,371 A    2/1986 Nebelung et al.
(Continued)

FOREIGN PATENT DOCUMENTS

WO    20151132549 A1    9/2015
WO    20181053349 A1    3/2018
(Continued)

OTHER PUBLICATIONS

Australian Examination Report dated Apr. 23, 2019 for related Australian Appln. No. 2017326462 3 Pages.
(Continued)

*Primary Examiner* — Tan-Uyen T Ho
*Assistant Examiner* — Chima U Igboko
(74) *Attorney, Agent, or Firm* — Womble Bond Dickinson (US) LLP

(57) ABSTRACT

A robotic surgical system includes a robotic arm comprising a first segment having a first plurality of links and a first plurality of actuated joint modules providing the robotic arm with at least five degrees of freedom, and a second segment having a proximal end coupled to a distal end of the first segment, and comprising a second plurality of links and a second plurality of actuated joint modules providing the robotic arm with at least two degrees or freedom. The robotic surgical system further comprises an instrument driver coupled to the second segment and configured to hold a surgical instrument. The second arm segment is configured to move the surgical instrument within a generally spherical workspace, and the first arm segment is configured to move the location of the spherical workspace.

26 Claims, 30 Drawing Sheets

(51) Int. Cl.

| | | |
|---|---|---|
| *A61B 34/35* | (2016.01) | |
| *A61B 34/37* | (2016.01) | |
| *A61B 34/00* | (2016.01) | |
| *G16H 20/40* | (2018.01) | |
| *G16H 40/63* | (2018.01) | |
| *A61B 1/00* | (2006.01) | |
| *B25J 9/10* | (2006.01) | |
| *B25J 13/02* | (2006.01) | |
| *B25J 15/00* | (2006.01) | |
| *B25J 17/02* | (2006.01) | |
| *G01L 1/14* | (2006.01) | |
| *G01L 3/14* | (2006.01) | |
| *G01L 5/22* | (2006.01) | |
| *A61B 1/313* | (2006.01) | |
| *B25J 13/08* | (2006.01) | |
| *G06F 19/00* | (2018.01) | |

(52) U.S. Cl.
CPC .............. *A61B 34/37* (2016.02); *A61B 34/70* (2016.02); *A61B 34/71* (2016.02); *A61B 34/77* (2016.02); *B25J 9/10* (2013.01); *B25J 9/1045* (2013.01); *B25J 13/02* (2013.01); *B25J 15/0019* (2013.01); *B25J 17/0283* (2013.01); *G01L 1/14* (2013.01); *G01L 3/14* (2013.01); *G01L 5/226* (2013.01); *G16H 20/40* (2018.01); *G16H 40/63* (2018.01); *A61B 1/3132* (2013.01); *A61B 2034/715* (2016.02); *B25J 13/085* (2013.01); *G06F 19/3418* (2013.01)

(58) Field of Classification Search
CPC ........ A61B 2034/304; A61B 2034/305; A61B 2034/306; A61B 2034/715; A61B 2034/731; A61B 2034/732; A61B 2034/733; A61B 2034/741; A61B 2034/742; A61B 2034/743; A61B 2034/744; A61B 34/30; A61B 34/32; A61B 34/35; A61B 34/37; A61B 34/71; A61B 34/70; A61B 34/72; A61B 34/73; A61B 34/74; A61B 34/75; A61B 34/76; A61B 34/77; A61B 2017/2919; A61B 2017/292; A61B 2017/2922; B25J 9/104; B25J 9/1045; B25J 9/106; B25J 9/1065; B25J 9/107; B25J 9/003; B25J 9/0033; B25J 9/0036; B25J 9/0039; B25J 9/0042; B25J 9/0045; B25J 9/0048; B25J 9/0051; B25J 9/0054; B25J 9/0057; B25J 9/006; B25J 9/0063; B25J 9/0066; B25J 9/0069; B25J 9/0072; B25J 9/0078; B25J 9/06; B25J 9/065; B25J 17/00; B25J 17/02; B25J 17/0216; B25J 17/0225; B25J 17/0233; B25J 17/0241; B25J 17/025; B25J 17/0258; B25J 17/0266; B25J 17/0275; B25J 17/0283; B25J 17/0291; B25J 18/00; B25J 18/02; B25J 18/04
USPC ........................................................ 606/130
See application file for complete search history.

(56) References Cited

U.S. PATENT DOCUMENTS

| | | |
|---|---|---|
| 5,150,759 A | 9/1992 | Borchard |
| 5,797,900 A | 8/1998 | Madhani et al. |
| 6,966,428 B1 | 11/2005 | Flynn |
| 2003/0083648 A1 | 5/2003 | Wang et al. |
| 2003/0195664 A1 | 10/2003 | Nowlin et al. |
| 2006/0167440 A1 | 7/2006 | Cooper et al. |
| 2007/0089557 A1* | 4/2007 | Solomon ............... B25J 9/1045 74/490.01 |
| 2007/0261894 A1 | 11/2007 | Harish |
| 2007/0299427 A1 | 12/2007 | Yeung et al. |
| 2008/0087871 A1 | 4/2008 | Schena |
| 2011/0023651 A1 | 2/2011 | Cooper |
| 2013/0023794 A1 | 1/2013 | Stein et al. |
| 2013/0325033 A1 | 12/2013 | Schena et al. |
| 2013/0331644 A1 | 12/2013 | Pandya et al. |
| 2014/0358162 A1 | 12/2014 | Valdastri et al. |
| 2015/0038982 A1* | 2/2015 | Kilroy ................. A61B 90/361 606/130 |
| 2015/0081098 A1 | 3/2015 | Kogan |
| 2015/0237308 A1 | 8/2015 | Tanaka et al. |
| 2017/0020615 A1* | 1/2017 | Koenig ................. A61B 34/30 |
| 2018/0079074 A1 | 3/2018 | Devengenzo et al. |
| 2018/0080841 A1 | 3/2018 | Cordoba et al. |

FOREIGN PATENT DOCUMENTS

| | | |
|---|---|---|
| WO | 20181053360 A1 | 3/2018 |
| WO | 20181053361 A1 | 3/2018 |

OTHER PUBLICATIONS

Written Opinion of the International Search Authority dated Jan. 23, 2018 for WO Application No. PCT/US17/051921.
Written Opinion of the International Search Authority dated Dec. 1, 2017 for WO Application No. PCT/US17/051922.
Written Opinion of the International Search Authority dated Dec. 1, 2017 for WO Application No. PCT/US17/051908.
Outgoing —ISA/210—International Search Report dated Jan. 23, 2018 for WO Application No. PCT/US17/051921.
Outgoing—ISA/210—International Search Report dated Dec. 1, 2017 for WO Application No. PCT/US17/051922.
Outgoing—ISA/210—International Search Report dated Dec. 1, 2017 for WO Application No. PCT/US17/051908.
Examiner's Report of the Canadian Patent Office dated Jan. 31, 2020, for Canadian application No. 3,034,639.
Extended European search report of the European Patent Office dated Mar. 23, 2020, for European Application No. EP17851661.3.

\* cited by examiner

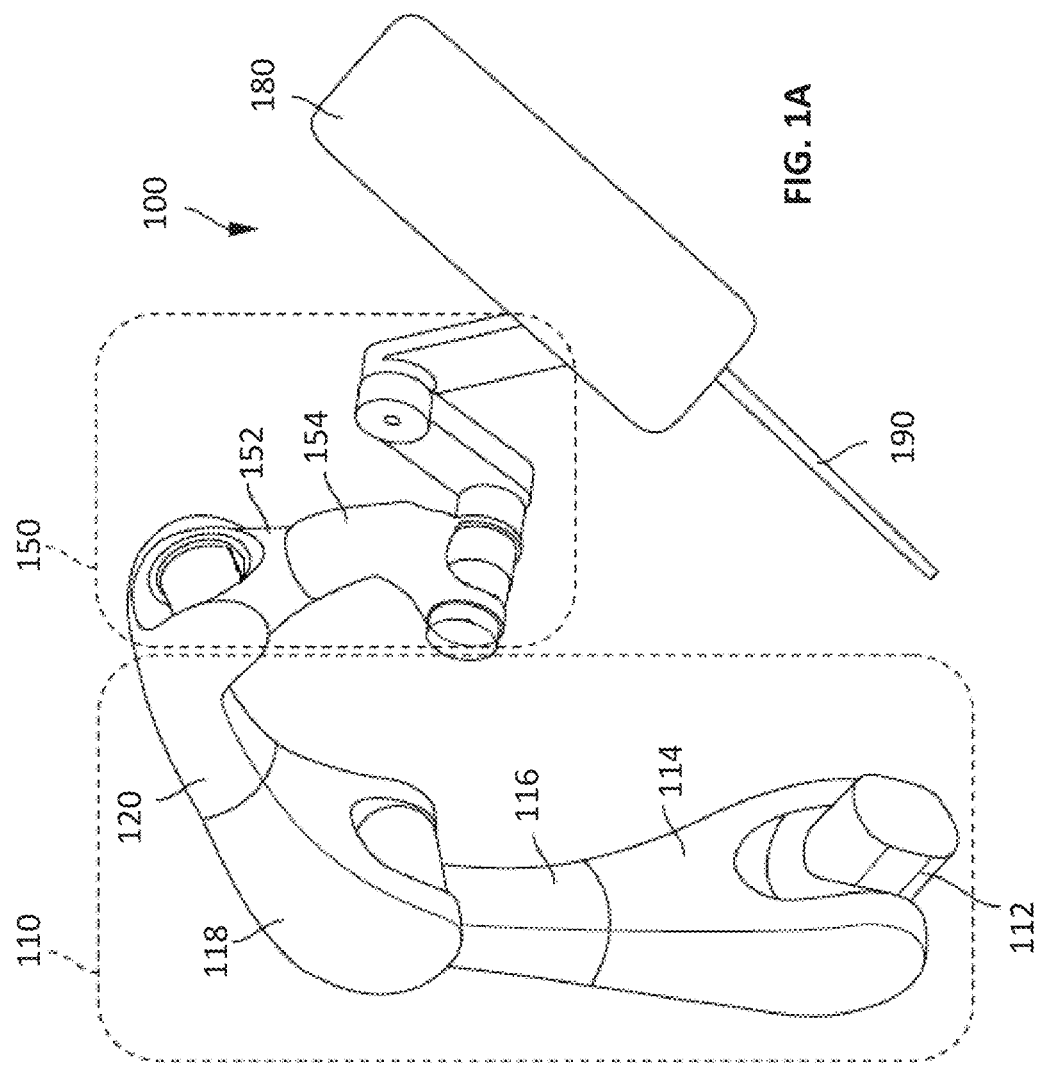

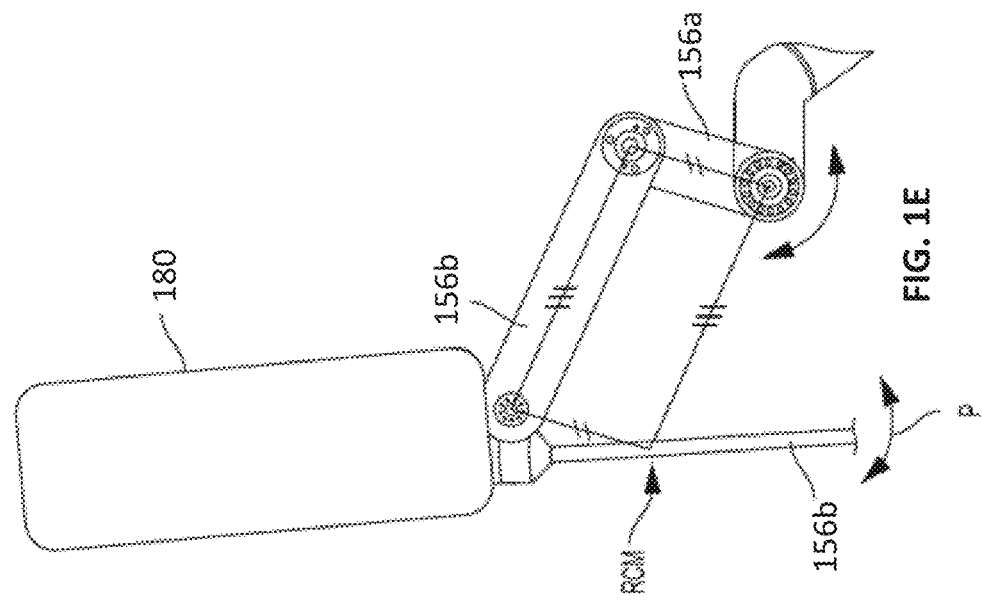
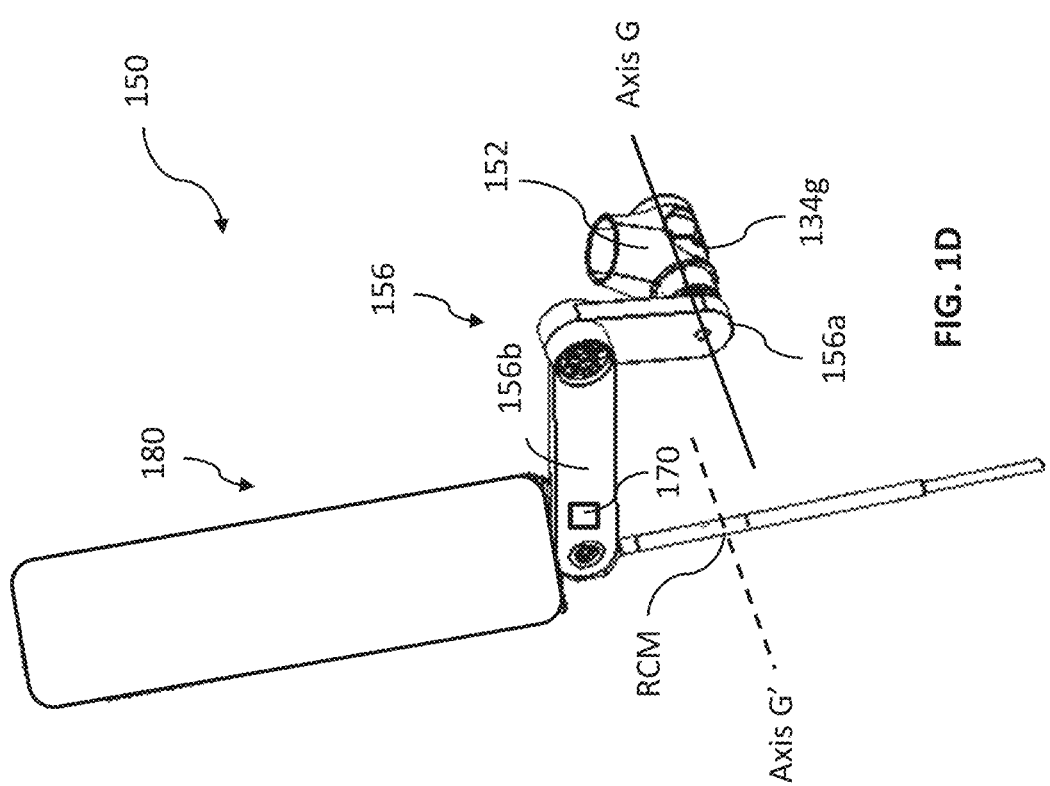

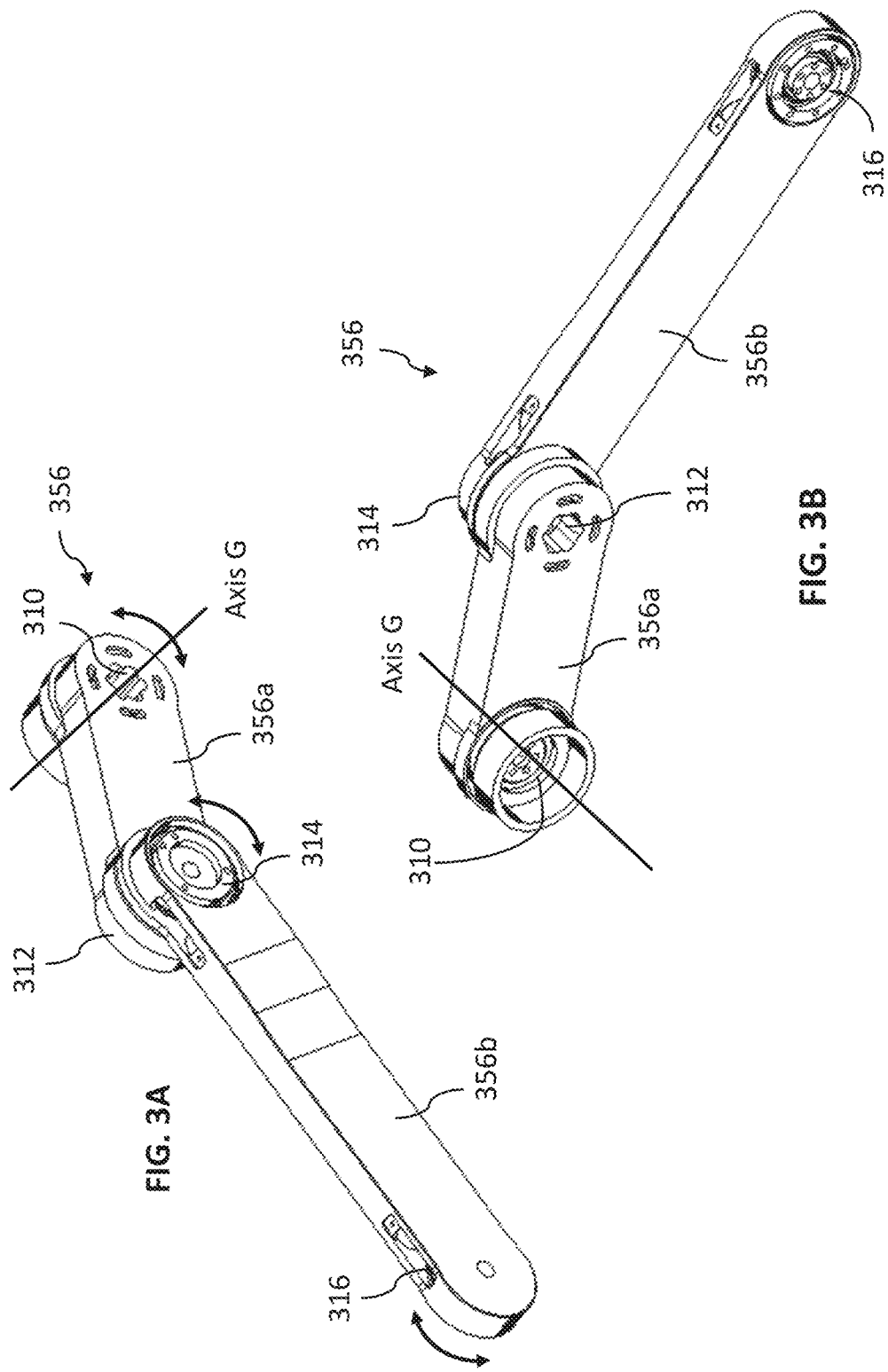

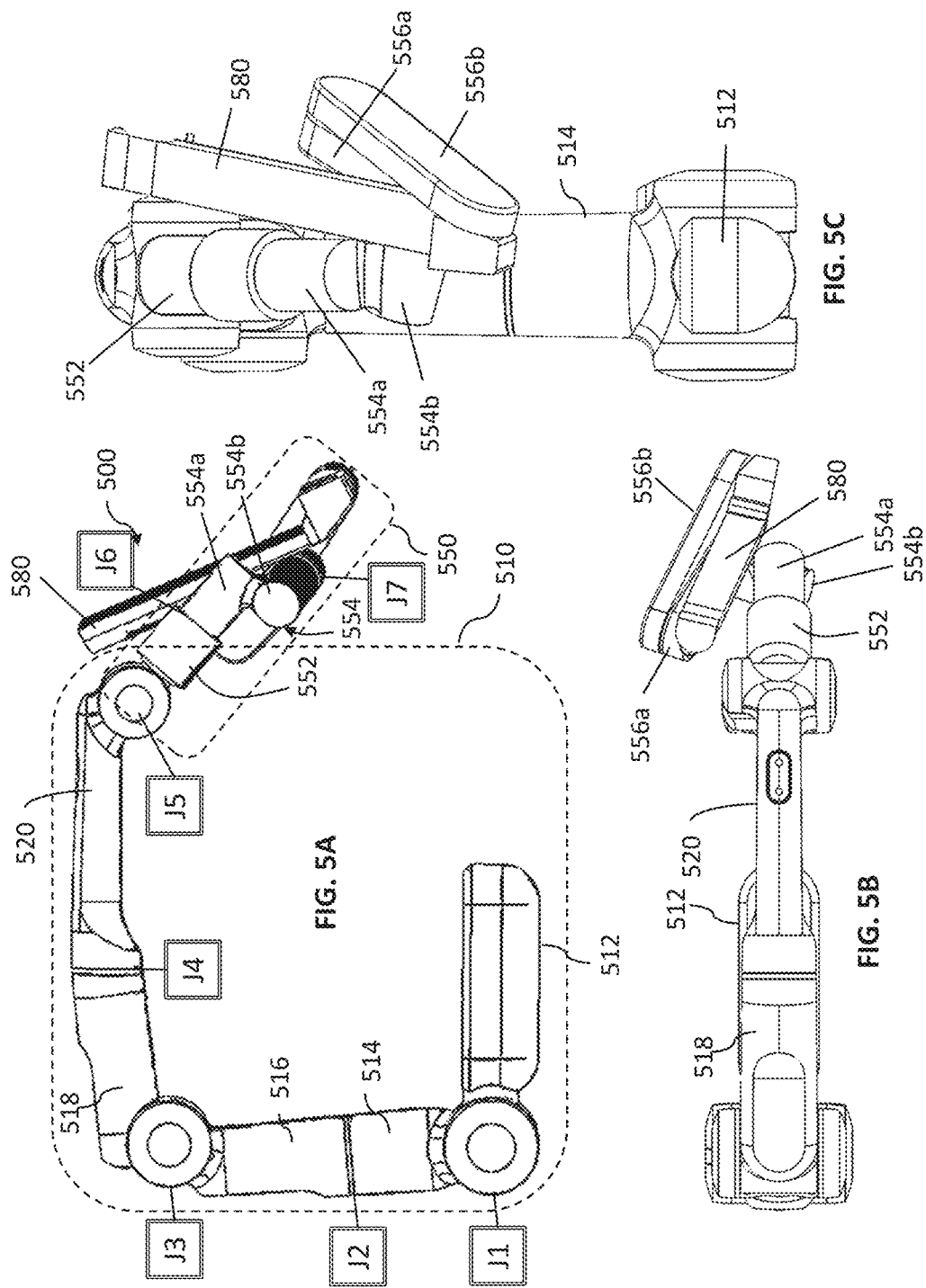

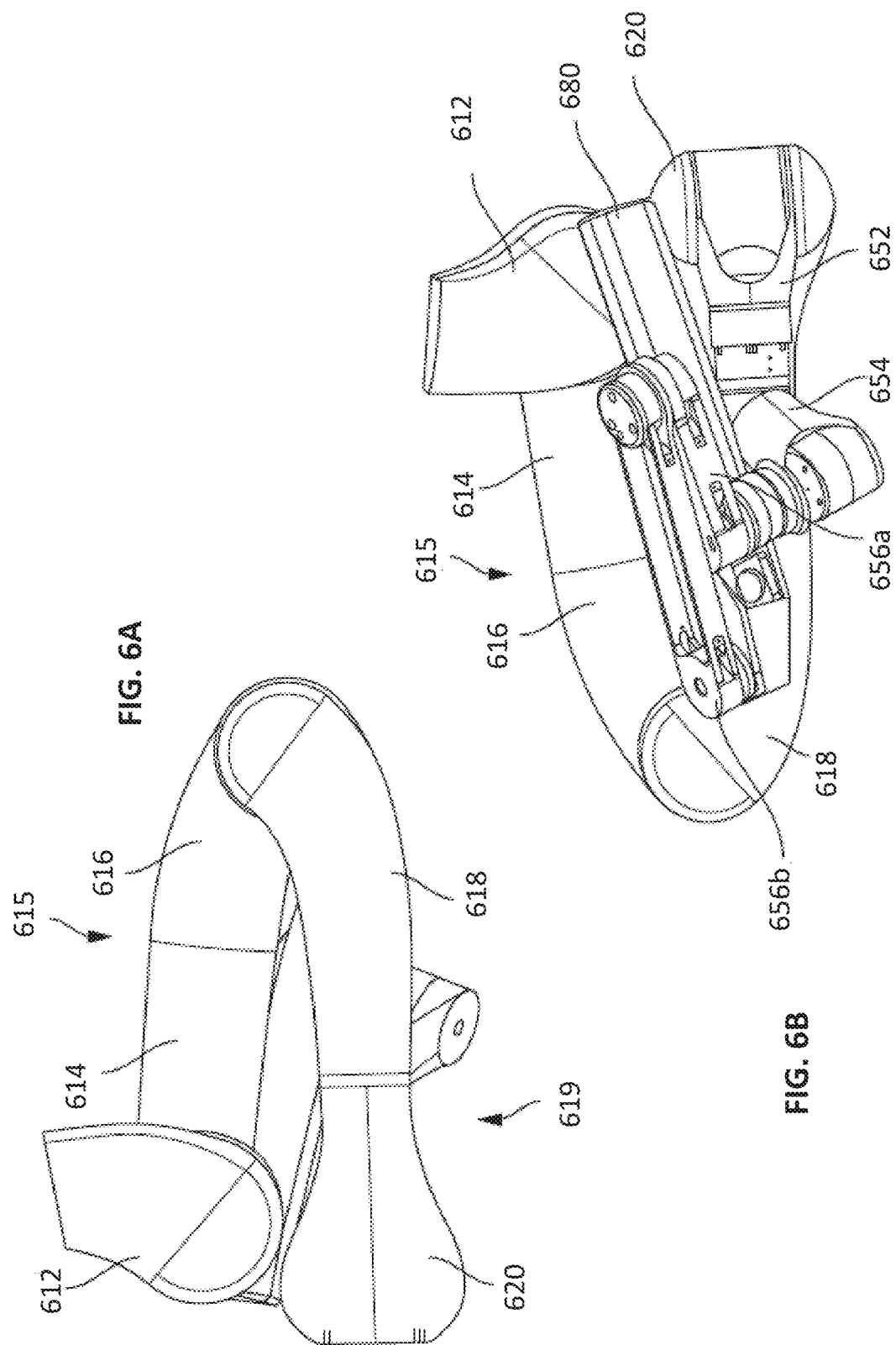

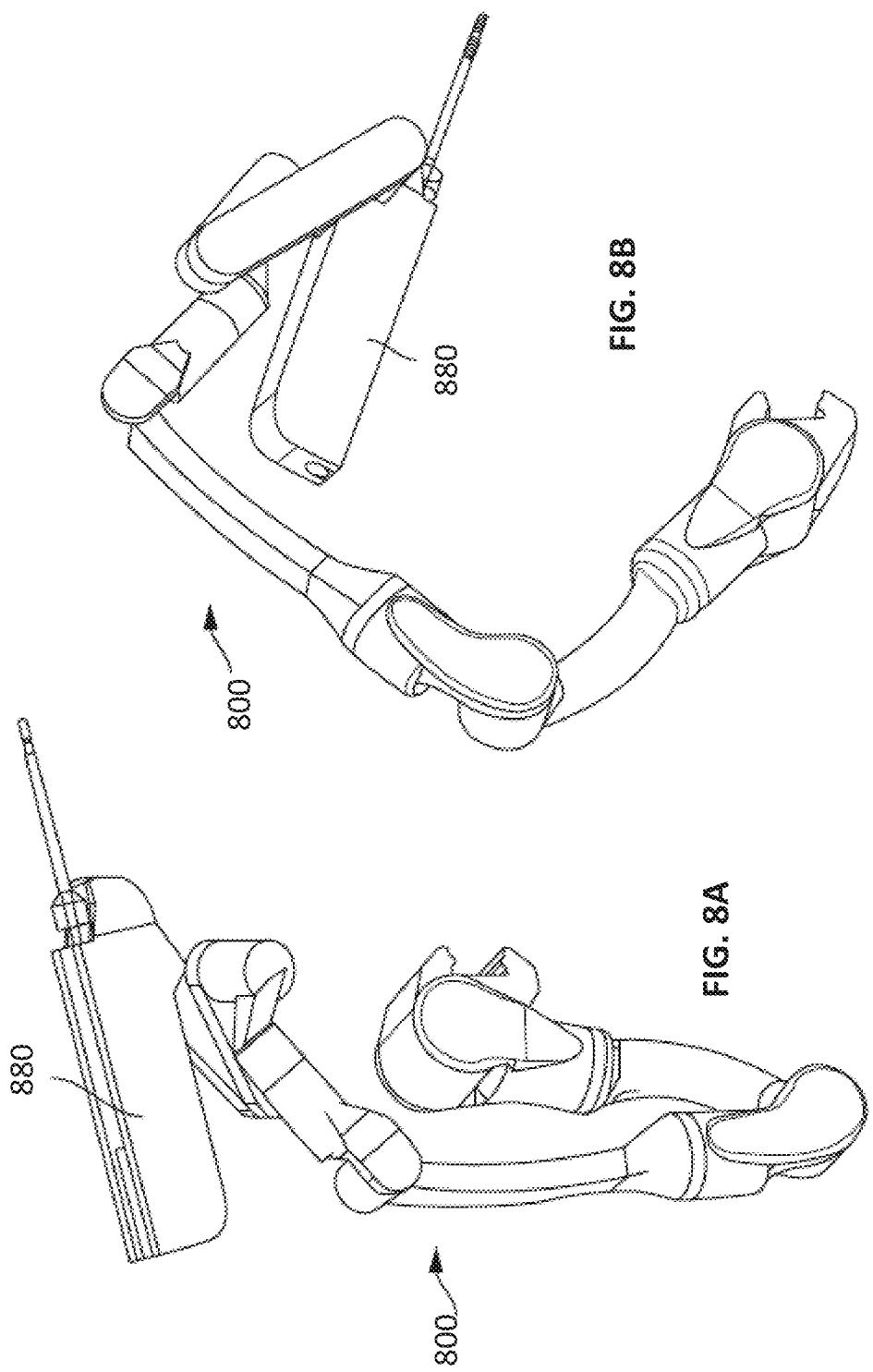

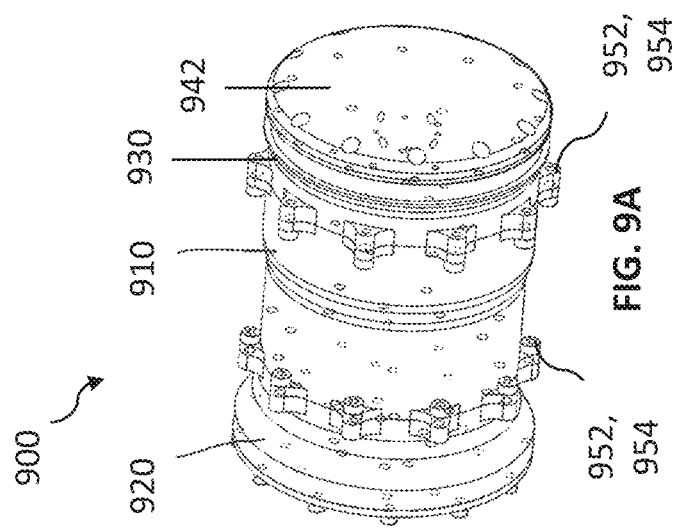

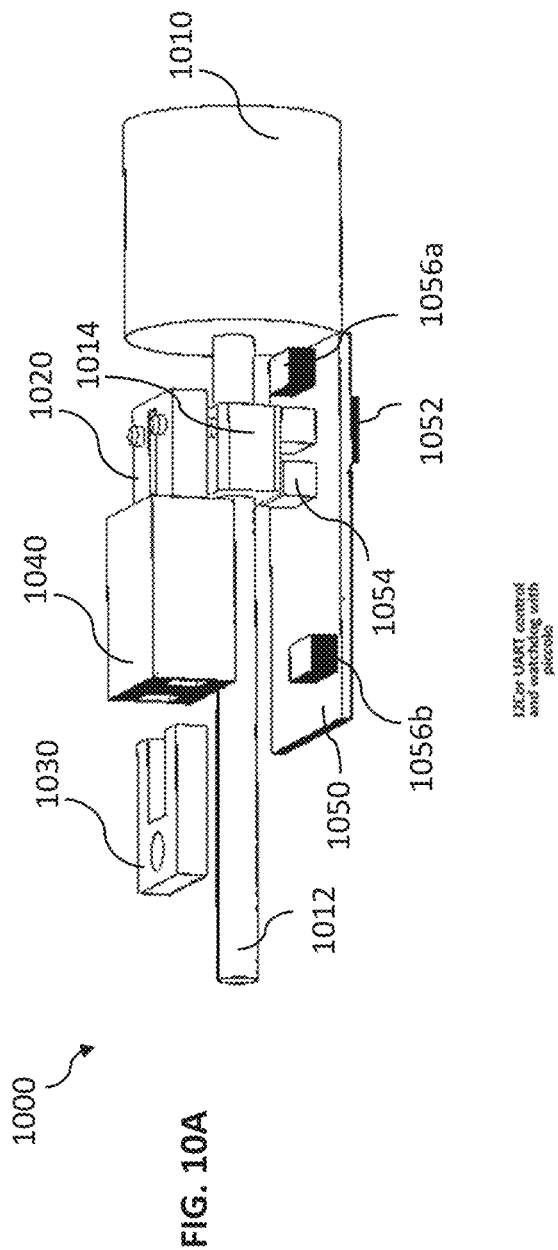
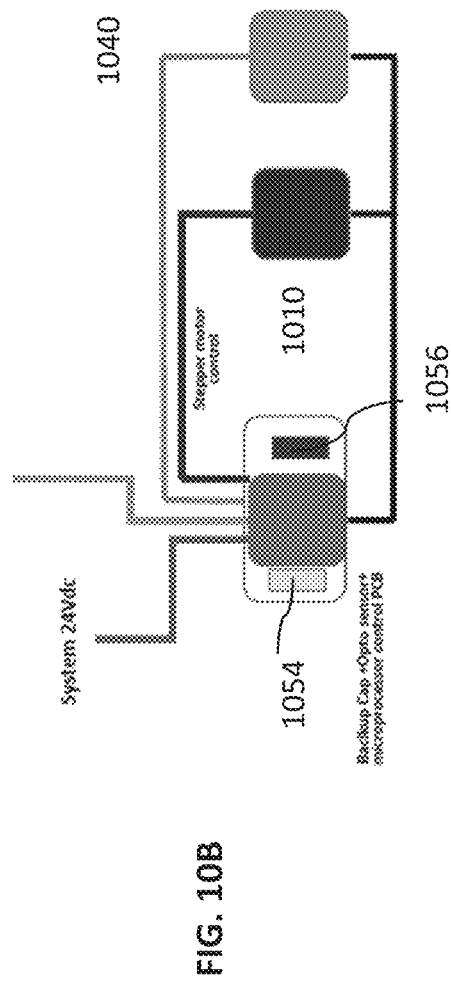
FIG. 10A
FIG. 10B

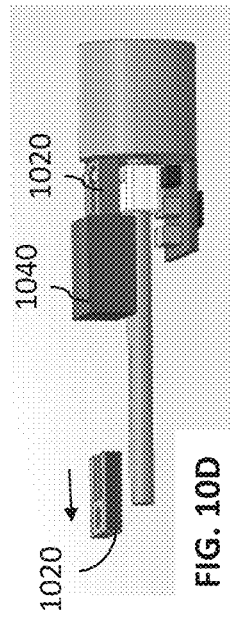 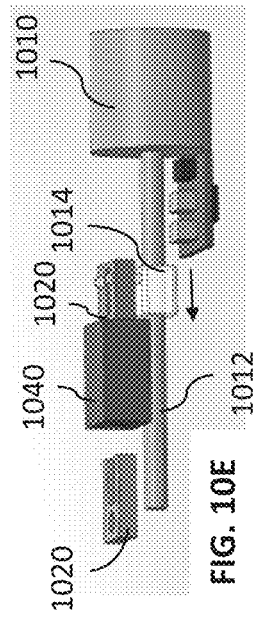 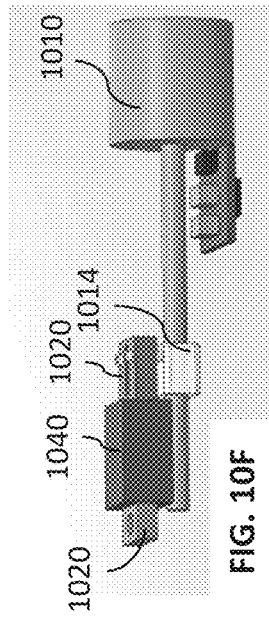 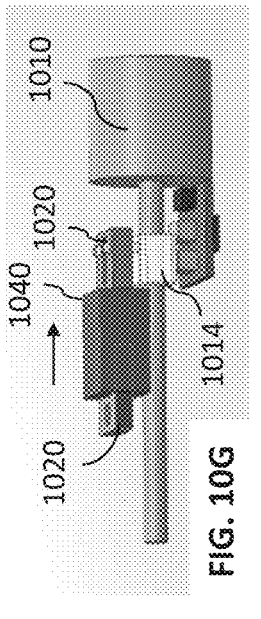
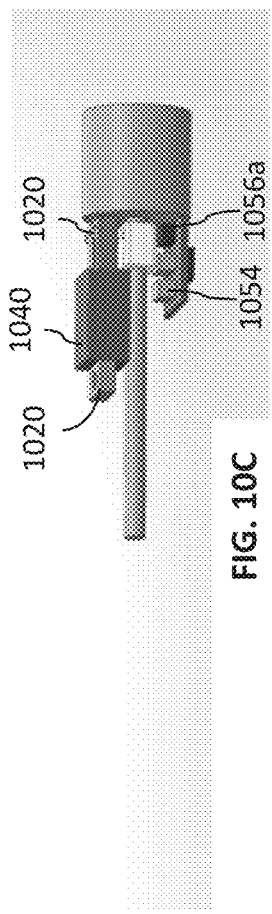

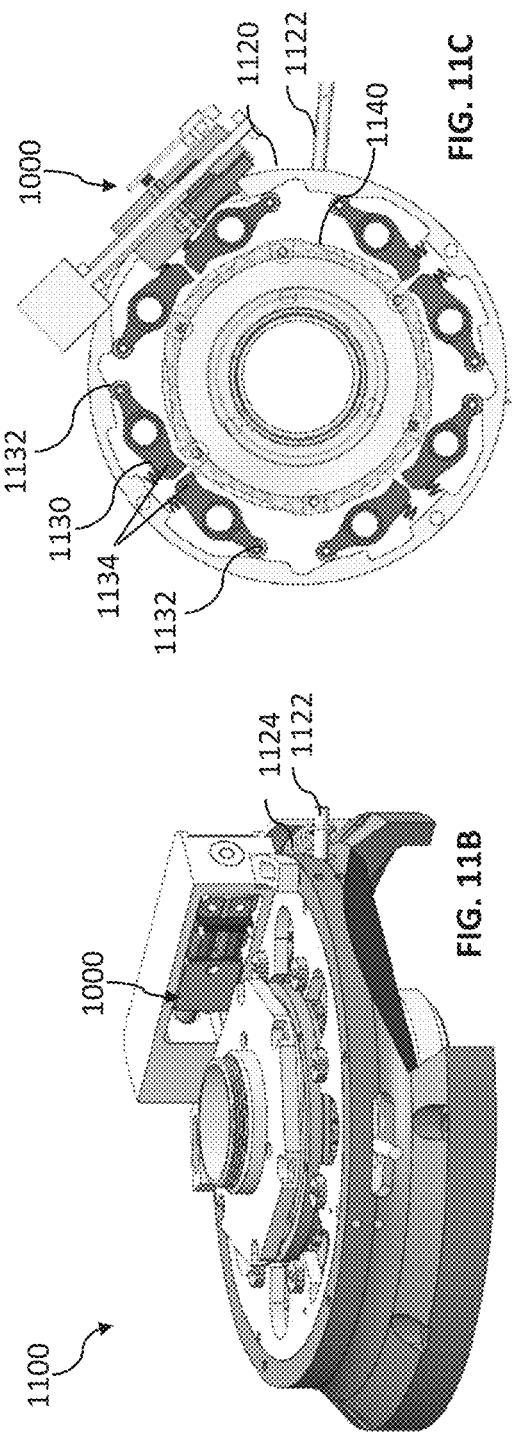

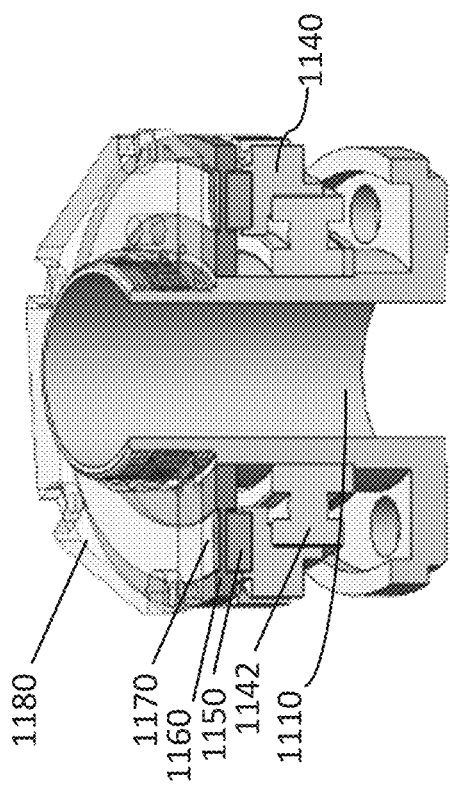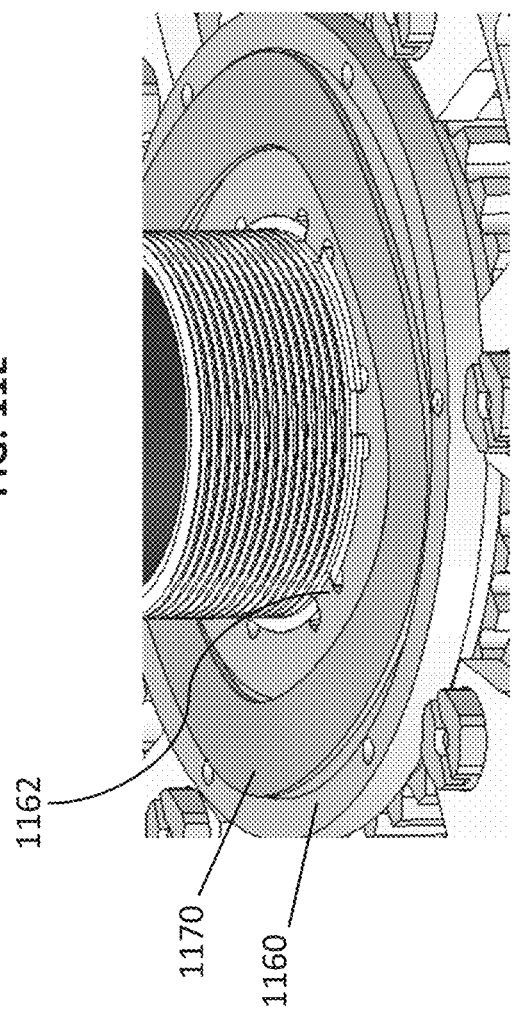

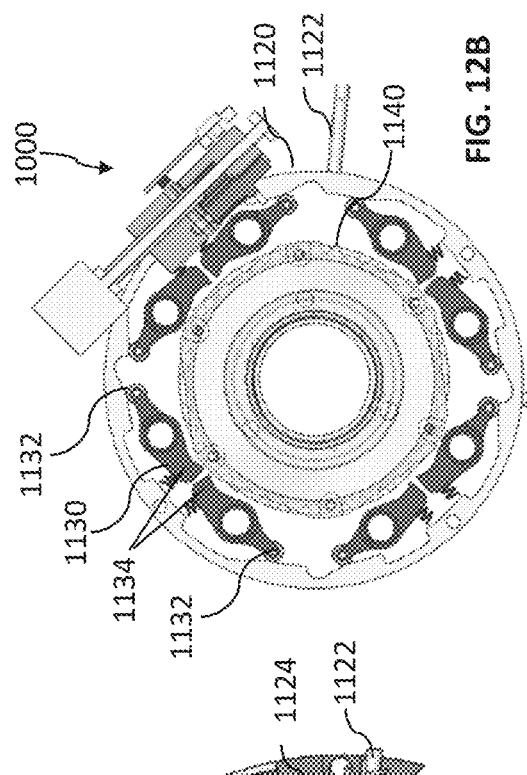
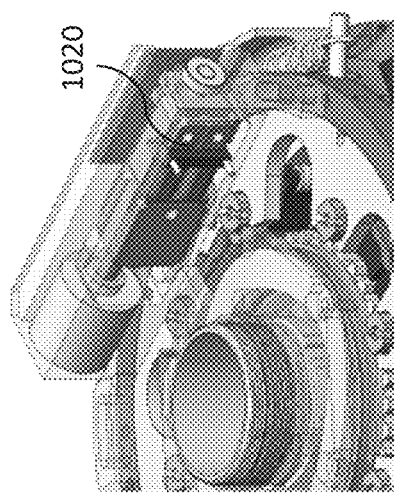
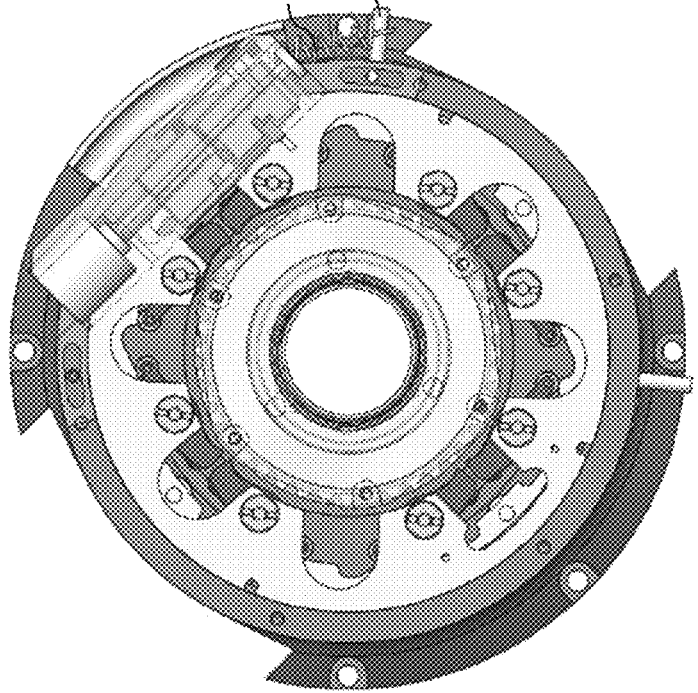

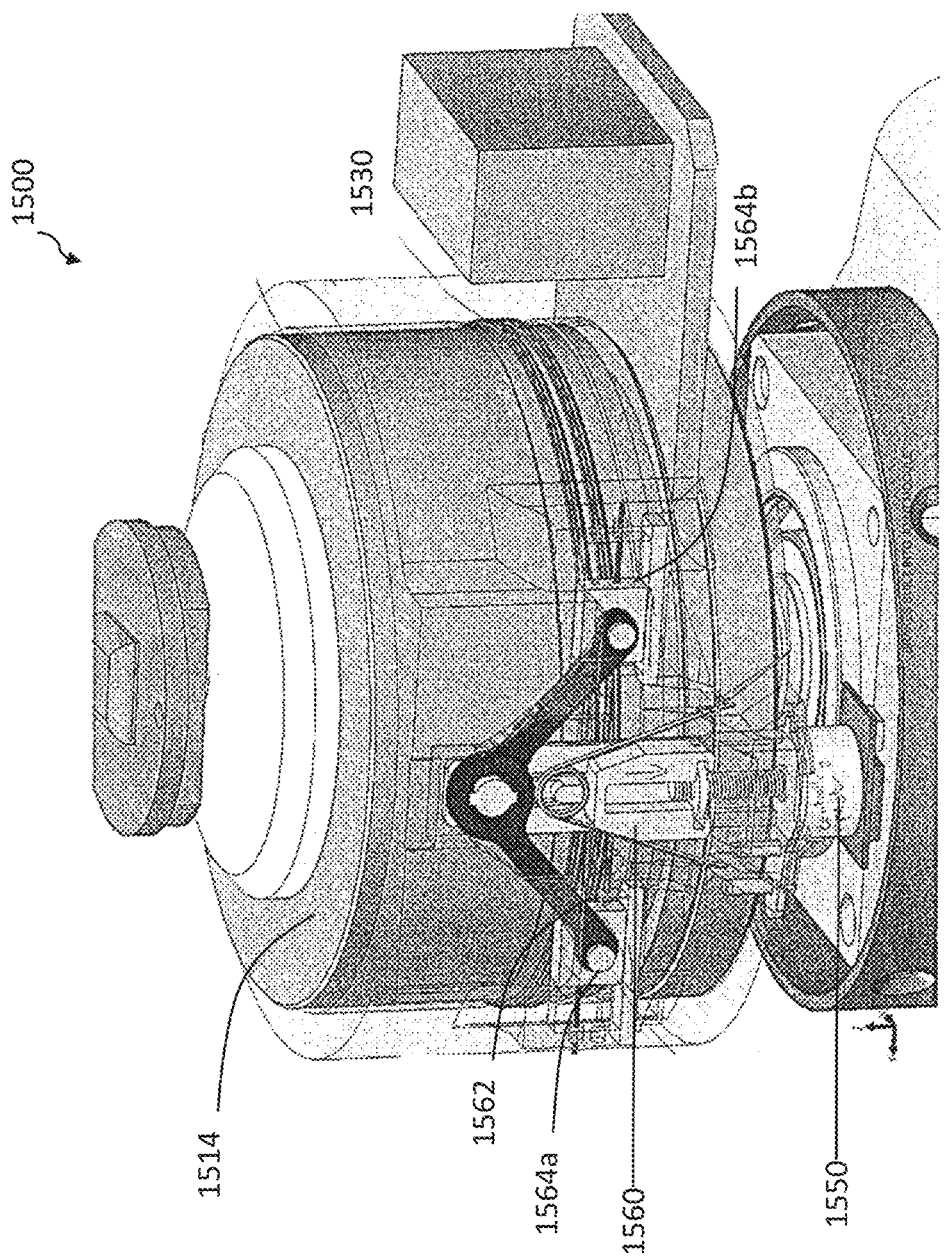

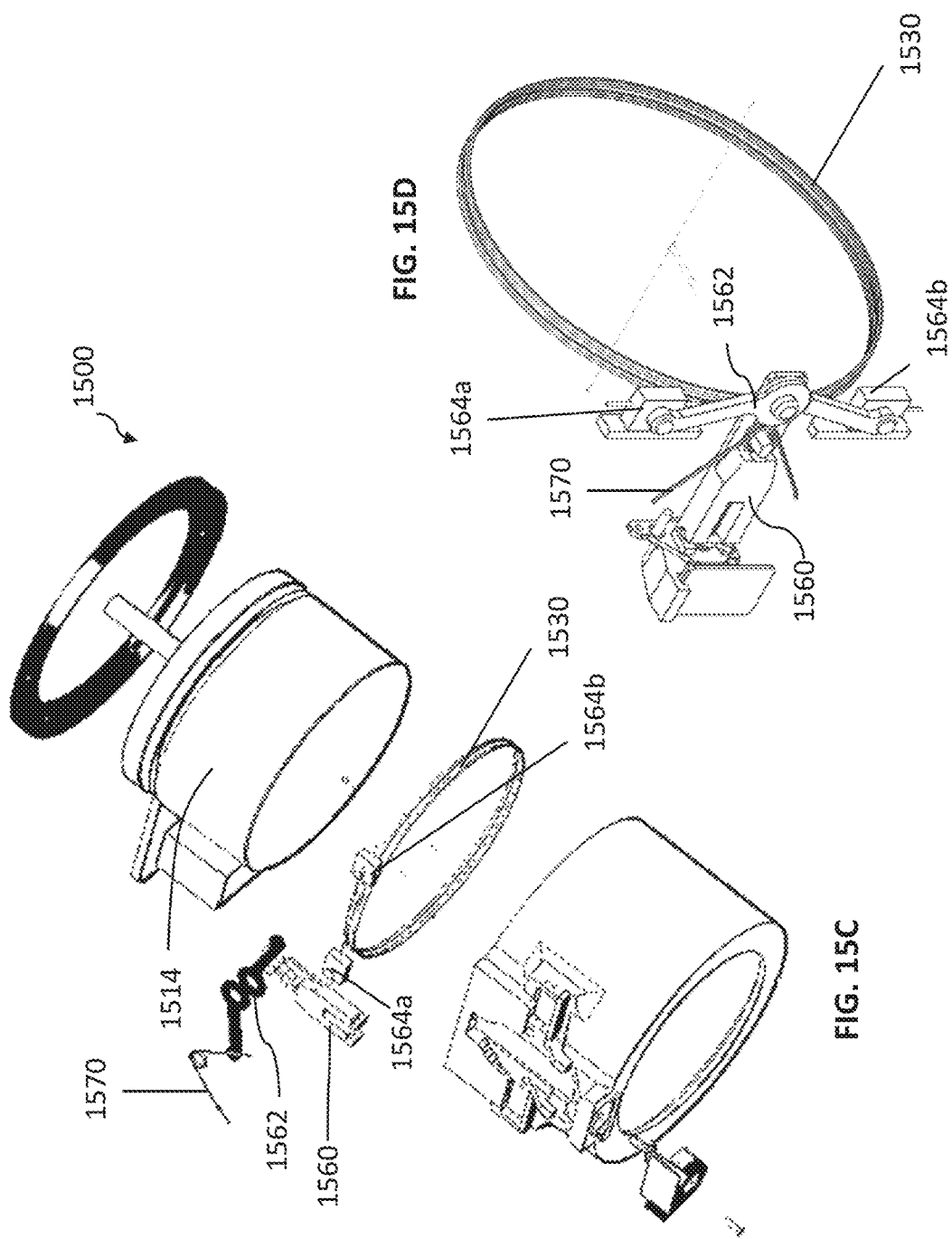

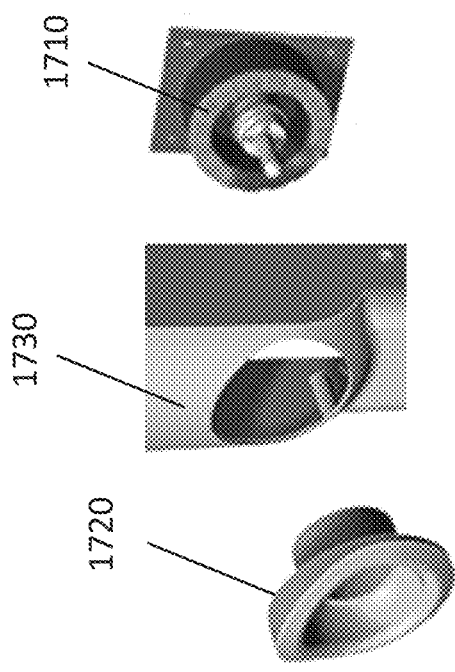
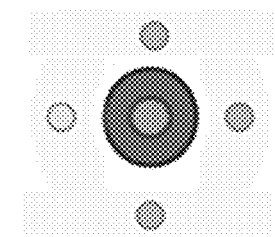
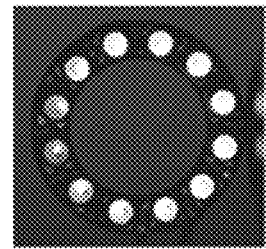
FIG. 17A
FIG. 17C
FIG. 17B

ROBOTIC ARMS

CROSS-REFERENCE TO RELATED APPLICATIONS

This application claims priority to U.S. Patent Application Ser. No. 62/395,704, filed on Sep. 16, 2016, which is hereby incorporated by this reference in its entirety.

TECHNICAL FIELD

This disclosure relates generally to robotic or robotic-assisted systems and, more particularly, to robotic arms for robotic or robotic-assisted surgical systems.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more tools and at least one camera through the incisions into the patient. The surgical procedures are then performed by using the introduced instruments, with the visualization aid provided by the camera.

Generally, MIS provides multiple benefits, such as reduced patient scarring, less patient pain, shorter patient recovery periods, and lower medical treatment costs associated with patient recovery. However, standard MIS systems have a number of drawbacks. For example, non-robotic MIS systems place higher demands on the surgeon, in part because they require surgeons to indirectly manipulate tissue via tools in a manner that may not be natural. Conventional robotic systems, which may include robotic arms for manipulating tools based on commands from an operator, may provide many benefits of MIS while reducing demands on the surgeon. However, such robotic arms tend to be large and difficult to set up and manage. Additionally, many conventional robotic arms have a significantly limited number of arm configurations such that they restrict accessibility to internal organs in the body. Thus, it is desirable to have robotic arms for robotic-assisted surgical systems that are easier to use and present more clinical options for a greater variety of procedures and patient types.

SUMMARY

Generally, a robotic surgical system may include a robotic arm and an instrument driver configured to hold a surgical instrument. The robotic arm may include a roll link, a first link rotatable within a first plane and having a proximal end coupled to a distal end of the base link, and a second link rotatable within a second plane and having a proximal end coupled to a distal end of the first link. The instrument driver may be coupled to a distal end of the second link such that the instrument driver is not parallel to at least one of the first and second planes. In some variations, the robotic arm may be foldable into a compact configuration in which the instrument driver is positioned between the roll link and the first link and/or second link. For example, at least a portion of the roll link may be oriented along a roll axis and at least a portion of the instrument driver may be angularly offset from the roll axis.

The first and second links in the robotic arm may be different lengths. For example, the first link may be shorter than the second link. The first and second links may be operatively coupled with a pulley arrangement (e.g., to operate a parallelogram or other suitable four-bar linkage, as described herein).

In some variations, the robotic arm may include a first arm segment including a first plurality of actuated links providing the robotic arm with at least five degrees of freedom. The robotic arm may include a second arm segment including a second plurality of actuated links providing the robotic arm with at least two degrees of freedom. In some variations, the second plurality of actuated links may include a roll link, a first link, and a second link (e.g., the roll link, the first link, and the second link described above). In some variations, the second arm segment may be configured to move the surgical instrument within a generally spherical workspace, and the first arm segment may be configured to move the location of the spherical workspace.

For example, a degree of freedom of the robotic arm (e.g., in the second arm segment) may be provided by rotation of the roll link relative to the first arm segment. Rotation of the roll link relative to the first arm segment may, for example, cause movement of the instrument driver in a roll direction. As another example, a degree of freedom of the robotic arm (e.g., in the second arm segment) may be provided by synchronous rotation of the first and second links relative to the roll link. Synchronous rotation of the first and second links may, for example, cause movement of the instrument driver in a pitch direction.

In some variations, the instrument driver may be configured to rotate the surgical instrument around a remote center of motion. In some of these variations, the second arm segment may be configured to rotate the instrument driver around a roll axis and a pitch axis, where at least one of the roll axis and the pitch axis does not intersect with the remote center of motion. For example, the roll axis and/or the pitch axis may be offset by about 5 centimeters or less, or about 2 centimeters or less, from the remote center of motion. In some variations, both the roll axis and the pitch axis may not intersect with the remote center of motion.

Generally, in some variations, a robotic surgical system may include a robotic arm and an instrument driver. The robotic arm may include a first arm segment having a first plurality of links providing the robotic arm with at least five degrees of freedom, and a second arm segment having a second plurality of links providing the robotic arm with at least two degrees of freedom. The instrument driver may be configured to hold a surgical instrument and configured to rotate the surgical instrument around a remote center of motion. The second arm segment may be configured to rotate the instrument driver around a roll axis and a pitch axis, where the roll axis and/or the pitch axis does not intersect with the remote center of motion. For example, in some variations, at least one of the roll axis and the pitch axis may be offset by about 5 centimeters of less, or about 2 centimeters or less, from the remote center of motion.

The second arm segment may be configured to move the surgical instrument held by the instrument driver within a generally spherical workspace, and the first arm segment may be configured to move the location of the generally spherical workspace. In some variations, the second plurality of links may include a roll link, a first pitch link, and a second pitch link. Rotation of the roll link relative to the first arm segment may cause movement of the instrument driver around the roll axis. Synchronous rotation of the first and second pitch links may cause movement of the instrument driver around the pitch axis. In some variations, the first and second pitch links may be different lengths (e.g., the first pitch link may be shorter than the second pitch link).

In some variations, the robotic surgical system may include a plurality of joint modules configured to actuate the first and second pluralities of actuated links. A controller may be configured to actuate at least one joint module based on at least one of a plurality of control modes. For example, in a gravity compensation mode, the controller may determine gravity force acting on at least a portion of the links, and actuate at least one joint module to counteract the determined gravity force. As another example, in a friction compensation mode, the controller may determine the presence of a user-applied force acting to back-drive at least one joint module, and actuate the at least one joint module to reduce the user-applied force required to back-drive the at least one joint module. In the friction compensation mode, the controller may, for example, actuate the at least one joint module based on a dithering signal until the controller determines the presence of the user-applied force.

In some variations, the robotic surgical system may include a fine positioning clutch configured to substantially restrict relative positions of at least a portion of the second plurality of links in the second arm segment while enabling relative movement among the first plurality of links in the first arm segment. Other suitable manually-operated and/or controller-operated features may be used to operate the robotic surgical system, such as those described herein.

BRIEF DESCRIPTION OF THE DRAWINGS

FIGS. 1A-1D are schematic illustrations of one variation of a robotic arm for a robotic-assisted surgical system. FIG. 1E is a symbolic schematic of one variation of a spherical pitch assembly for a robotic arm.

FIGS. 3A and 3B are schematic illustrations of one variation of a spherical pitch assembly for a robotic arm.

FIGS. 5A-5C are side view, top view, and front views of another variation of a robotic arm for a robotic-assisted surgical system.

FIGS. 6A and 6B are schematic illustrations of exemplary folded configurations of a variation of a robotic arm.

FIGS. 8A and 8B are schematic illustrations of "low" and "flipped" arm configurations of one variation of a robotic arm.

FIG. 9A is a perspective view of an exemplary joint module.

FIG. 10A is a schematic illustration of one variation of a secondary actuator for a bi-stable safety brake. FIG. 10B is a control diagram for the secondary actuator depicted in FIG. 10A.

FIGS. 10C-10G are schematic illustrations of the secondary actuator, in various states, for actuating a bi-stable brake.

FIGS. 11B-11F are schematic illustrations of various subassemblies in the bi-stable safety brake depicted in FIG. 11A.

FIGS. 12A-12C are schematic illustrations of the brake depicted in FIG. 11A in a "brake off" mode.

FIGS. 15A and 15B are partial perspective views of another variation of a band brake-type safety brake for a joint module. FIG. 15C is an exploded perspective view of the brake depicted in FIGS. 15A and 15B. FIG. 15D is a perspective view of a band assembly in the brake depicted in FIGS. 15A and 15B.

FIG. 17A is a schematic illustration of a light module assembly in one variation of a robotic arm for communicating information to a user. FIGS. 17B and 17C are exemplary illumination patterns of the light module assembly depicted in FIG. 17A.

DETAILED DESCRIPTION

Figure 1C:
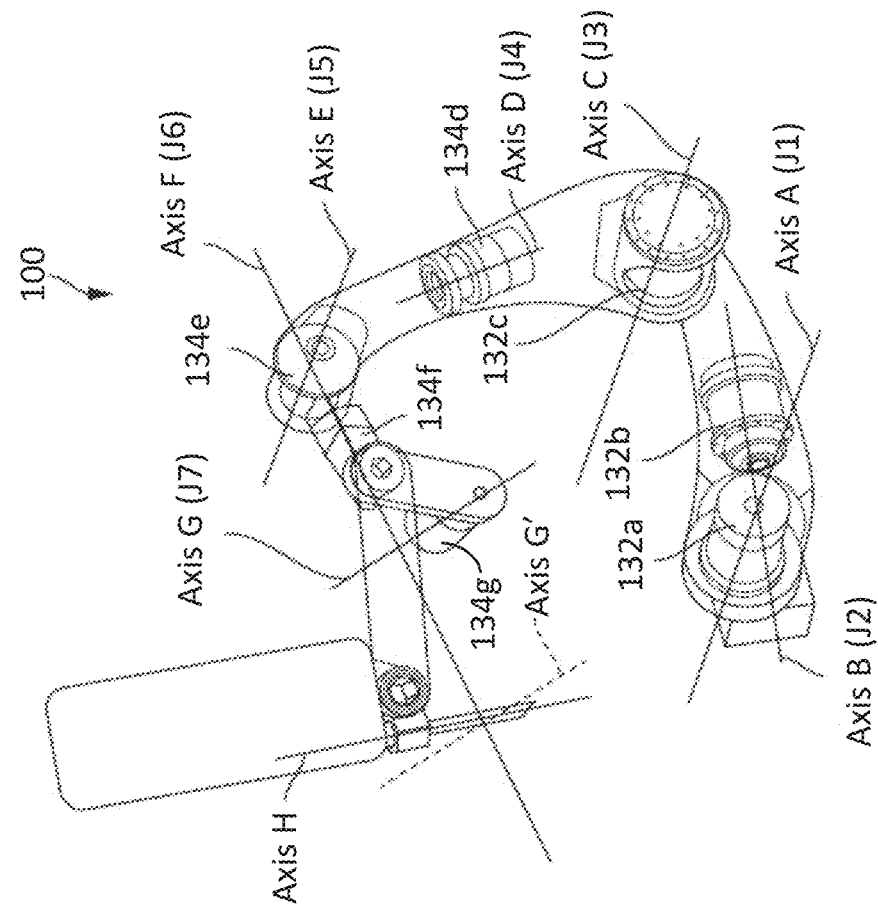

Non-limiting examples of various aspects and variations of the invention are described herein and illustrated in the accompanying drawings.

Robotic Arm Overview

Generally, a robotic or robotic-assisted surgical system (e.g., to enable a minimally-invasive surgical procedure) may include one or more robotic arms for manipulating surgical instruments, such as during minimally-invasive surgery. A robotic arm may include a plurality of links, a plurality of actuated joint modules that enable relative movement between adjacent links. For example, as shown in FIG. 1A, a robotic arm may include a first segment 110 having a proximal end and a distal end, and a second segment 150 having a proximal end (coupled to the distal end of first segment 110) and a distal end. Additionally, an instrument driver 180 may be coupled to the distal end of second segment 150 and be configured to hold and actuate a surgical instrument passing through a cannula 190.

During use of the robotic arm 100 for a surgical procedure, the proximal end of first segment 110 may be mounted or otherwise coupled to a structure (e.g., a surgical table, cart, wall, ceiling, etc.) at a mounting point near the patient during a surgical procedure. In some variations, the first segment 110 may be referred to as the "Cartesian arm" segment because the first segment 110 may position a mechanical remote center of motion (further described below) in three-dimensional space (e.g., x-y-z coordinates) relative to the mounting point of the first segment 110. Furthermore, the second segment 150 may be referred to as the "spherical arm" segment because the second segment 150 may move the tip of the surgical instrument held by the instrument driver within an approximately spherical volume of space as defined by the range of motion of the second segment 150. The combination of the Cartesian arm segment and the spherical arm segment may provide for a high degree of setup flexibility and dexterity for manipulating the surgical instrument for various procedure types and patient types.

Robotic Arm Links

Figure 1B:
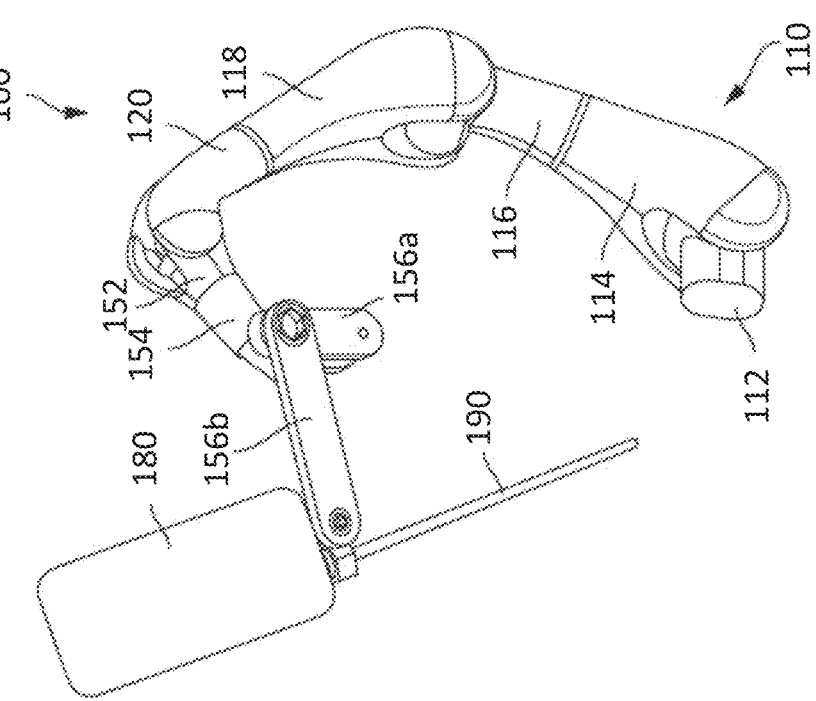

In some variations, as shown in FIG. 1B, the first segment 110 may include a first plurality of links and a first plurality of actuated joint modules for actuating the first plurality of links relative to one another. For example, the first segment 110 may include at least five links: a base link 112, a shoulder pitch link 114, a shoulder roll link 116, an elbow link 118, and a forearm link 120, which are arranged in series. Adjacent links may be connected in a manner such that the adjacent links are substantially constrained to movement around one axis relative to one another. For instance, the base link 112 and the shoulder pitch link 114 may be substantially constrained to relative movement around a pitch axis (e.g., the angle between the longitudinal axis of the base link 112 and the longitudinal axis of the shoulder pitch link 114 may increase or decrease), such as with a clevis joint construction. The shoulder pitch link 114 and the shoulder roll link 116 may be substantially constrained to relative movement around a roll axis (e.g., the longitudinal axes of the shoulder pitch link 114 and the shoulder roll link 116 may be substantially coaxial). The shoulder roll link 116 and the elbow link 118 may be substantially constrained to relative movement around another pitch axis (e.g., the angle between the longitudinal axis of the shoulder roll link 116 and the longitudinal axis of the elbow link 118 may increase or decrease), such as by a clevis joint construction. The elbow link 118 and the forearm link 120 may be substantially constrained to relative movement around another roll axis (e.g., the longitudinal axes of the elbow link 118 and the forearm link 120 may be substantially coaxial).

Additionally, the first segment 110 may include a first plurality of actuated joint modules 132 configured to actuate the first segment 110 with at least five degrees of freedom (DOFs), including at least two redundant DOFs beyond the 3 DOF task of positioning the mechanical remote center of motion in three-dimensional space. For instance, as shown in FIG. 1C, a first joint module 132a may couple the shoulder pitch link 114 to the base link 112, and include at least one actuator configured to pivot the shoulder pitch link 114 around Axis A relative to the base link 112. A second joint module 132b may couple the shoulder roll link 116 to the shoulder pitch link 114, and include at least one actuator configured to rotate the shoulder roll link 116 around Axis B relative to the shoulder pitch link 114. A third joint module 132c may couple the elbow link 118 to the shoulder roll link 116, and include at least one actuator configured to pivot the elbow link 118 around Axis C relative to shoulder roll link 116. A fourth joint module 132d may couple the forearm link 120 to the elbow link 118, and include at least one actuator configured to rotate the forearm link 120 around Axis D relative to the elbow link 118. A fifth joint module 132e may couple the second segment of the robotic arm (e.g., via spherical base link 152) to the distal end of the first segment (e.g., forearm link 120), and include at least one actuator configured to pivot the second segment of the robotic arm around Axis E relative to the forearm link 120. Exemplary actuation and control schemes of the links are described in further detail below.

The second segment 150 may include a second plurality of links and a second plurality of actuated joint modules for actuating the second plurality of links relative to one another. For example, as shown in FIG. 1B, the second segment 150 may include at least four links: a spherical base link 152, a spherical roll link 154, and first and second pitch links 156a and 156b, respectively, forming spherical pitch assembly 156. As described above, the spherical base link 152 may be coupled to a distal end of the first segment (e.g., forearm link 120) to connect the first arm segment 110 and the second arm segment 150. As in the first segment 110, adjacent links in the second segment 150 may be connected in a manner such that adjacent links are substantially constrained to movement around one axis relative to one another. For instance, as shown in FIG. 1A, the spherical base link 152 may couple to the forearm link 120 with a clevis joint construction that allows relative movement only around Axis E. Additionally, the spherical base link 152 and the spherical roll link 154 may be substantially constrained to relative movement around a roll axis (e.g., the longitudinal axes of the spherical base link 152 and the spherical roll link 154 may be substantially coaxial).

Additionally, the second segment 150 may include a second plurality of actuated joint modules configured to provide the second segment 150 with at least two DOFs. For instance, as shown in FIG. 1C, a sixth joint module 134f may couple the spherical roll link 154 to the spherical base link 152, and include at least one actuator configured to rotate the spherical roll link 154 around roll Axis F relative to the spherical base link 152. A seventh joint module 134g may couple the spherical pitch assembly (via first pitch link 156a) to the spherical roll link 154, and include at least one actuator configured to pivot the first pitch link 156 around Axis G relative to the spherical roll link 154. Exemplary actuation and control schemes of the links are described in further detail below.

As shown in FIG. 1D, the second segment 150 may include spherical pitch assembly 156 including a first pitch link 156a and a second pitch link 156b. Instrument driver 180 may be coupled to a distal end of second pitch link 156b. For instance, as shown in FIG. 1E, the first pitch link 156a, the second pitch link 156b, and the instrument driver may move as three links of a parallelogram or four-bar linkage, constrained with a drive mechanism (such as that further described below) with 1:1 ratio in order to replicate the rotation of first pitch link 156a around Axis G into rotation of the instrument driver around pitch Axis G' at the mechanical remote center of motion (RCM), where Axis G' is offset and parallel to Axis G. In other words, the seventh joint module 134g may actuate the first pitch link 156a to pivot around Axis G, which through the spherical pitch assembly 156 indirectly actuates the instrument driver (and the surgical instrument held by the instrument driver) to pivot around Axis G' at the RCM. The pitch assembly 156 may be configured to operate the surgical instrument about the RCM with increased ease, speed, and flexibility compared to other conventional pitch assembly mechanisms.

In some variations, the pitch assembly 156 may include first and second pitch links that are different lengths, where length is measured between pivoting points on the ends of a pitch link. For example, as shown in FIG. 1D, the first pitch link 156a may be shorter than the second pitch link 156b. For example, in some variations, the first pitch link 156a may have a length (as measured between pivot points) that is between about 10% and about 80% of the length of the second pitch link 156b (as measured between pivot points). In some variations, the first pitch link length may be between about 20% and about 70% of the second pitch link length, or between about 25% and about 65% of the second pitch link length. For example, the first pitch link 156a may rotate relative to the second pitch link 156b without physical interference and allow the pitch assembly 156 to collapse or fold down against itself into a smaller volume, or more compact configuration. Additionally, a shorter pitch link length may reduce the workspace volume required for the pitch assembly to operate, as a shorter pitch link will sweep a smaller volume throughout its rotation. Such a configuration can, for example, be useful for storage, transport, for reducing risk of collision between the pitch assembly and the patient or surgical personnel, and/or for reducing risk of collision between the pitch assembly and other parts of the robotic arm, etc.

For example, in some variations, the pitch assembly may be part of a four-bar linkage moving as an imperfect parallelogram. For example, as shown in the schematic of FIG. 2A, the distance between pivot points on the first pitch link 156a may be a distance "A", the distance between pivot points on the second pitch link 156b may be a distance "B", the distance between a distal pivot point on the second pitch link 156b and an RCM may be a distance "C", and the distance along a virtual link between the RCM and a proximal pivot point on the first pitch link 156a may be a distance "D." Distance "A" may be less than distance "C" such that the first link 156a having effective length "A" and the rotation of the link having effective length "C" are not always parallel as the pitch assembly 156 and instrument driver 180 move.

Figure 2B:
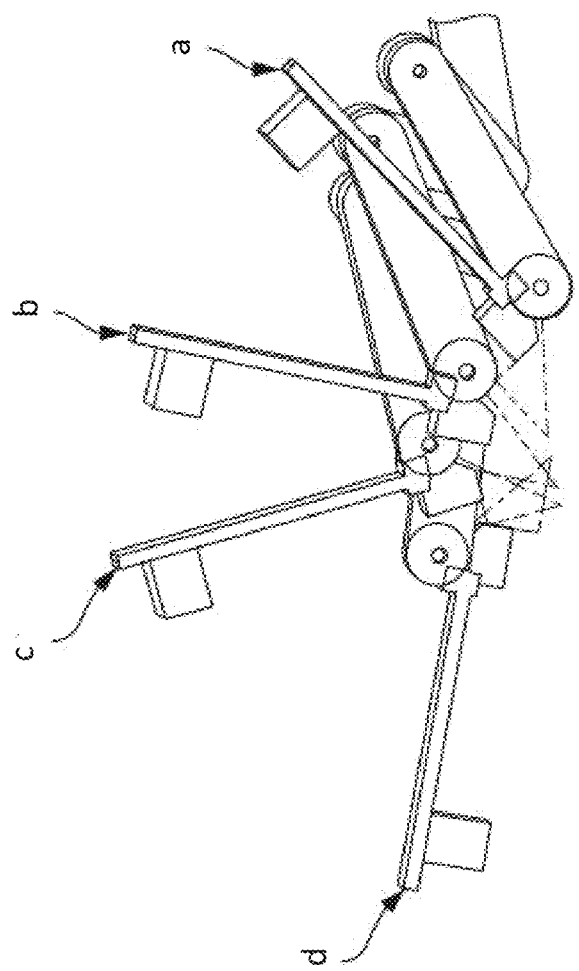
FIG. 2B is a schematic illustration of the spherical pitch assembly depicted in FIG. 2A, moving throughout a series of configurations with a moving remote center of motion.
Figure 2A:
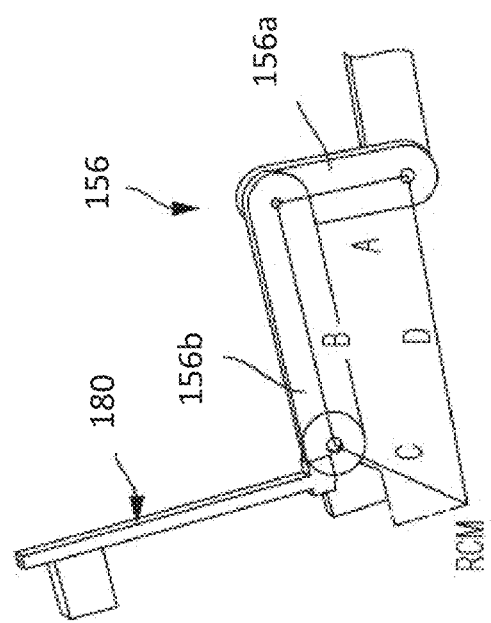
FIG. 2A is a schematic illustration of one variation of a spherical pitch assembly for a robotic arm.

Furthermore, as pitch assembly 156 shown in FIG. 2A moves, the RCM tends to move slightly. For example, FIG. 2B illustrates a series of four exemplary poses of the pitch assembly 156 that are the result of the first pitch link 156a rotating at its proximal end around Axis G (as noted in FIG. 1D, for example). As the pitch assembly moves through poses "a" through "d" in FIG. 2B, the RCM travels instead of remaining completely stationary, due to the imperfect nature of the parallelogram formed in part by the pitch links. In some variations, movement of the first pitch link 156a around Axis G may be limited due to the nature of a surgical task being performed. For example, in one exemplary variation, the first pitch link 156a may have a length (as measured between pivot points, described above as distance "A") between about 2 inches and about 4 inches, and the second pitch link 156b may have a length (as measured between pivot points, described above as distance "B") between about 7 inches and about 9 inches. In this exemplary variation, when the arm and instrument driver are performing typical surgical tasks, the pitch range of motion in the seventh joint module 134g may, for example, generally be between about 10 degrees and about 30 degrees. Under such exemplary conditions, the RCM in this exemplary variation may tend to travel between about 1 cm and about 3 cm. It should be understood that in other variations, the first and second pitch links 156a and 156b may have other suitable lengths, and/or the pitch range of motion for surgical tasks being performed may vary, which may cause the RCM to travel less than about 1 cm or more than about 3 cm. In some variations, the first arm segment (e.g., Cartesian arm segment) that is proximal to the pitch assembly may be controlled based on a control algorithm that maintains the RCM point fixed or substantially fixed in space, thereby compensating for the movement of the RCM that would otherwise occur. Such control algorithms or control modes for compensating for a deviating RCM may, for example, be similar to those described herein for maintaining a virtual RCM.

In the exemplary variation shown in FIGS. 3A and 3B, the spherical pitch linkage assembly 356 includes a series of pulleys and a series of bands connecting the pulleys that facilitate the four-bar linkage movement. First pitch link 356a is coupled to the output shaft of a joint module actuator that drives rotation of first pitch link 356a around Axis G, while second pitch link 356b is rotationally coupled to the instrument driver. First pitch link 356a includes a first pulley 310 coupled to the housing of the joint module actuator and located generally at a proximal point of first pitch link 356a, within an internal space of first pitch link 356a. First pitch link 356a also includes a second pulley 312 located generally at a distal point of first pitch link 356a, within the internal space of first pitch link 356a. The second pulley 312 is rigidly fixed to a proximal point of second pitch link 356b.

Additionally, second pitch link 356b includes a third pulley 314 located generally at a proximal point of second pitch link 356b, mounted on and rigidly fixed to a shaft of first pitch link 356a that extends into an internal volume of second pitch link 356b, such that when first pitch link 356a rotates, third pulley 314 rotates correspondingly. Second pitch link 356b also includes a fourth pulley 316 located generally at a distal point of second pitch link 356b, within the internal space of second pitch link 356b. The instrument driver is rotationally coupled to the distal point of second pitch link 356b and thus constrained to move when the fourth pulley 316 rotates.

At least one band (not shown in FIGS. 3A and 3B) wraps around the first and second pulleys such that when a joint module drives rotation of first pitch link 356a around Axis G, the orientation of the second pitch link 356b remains fixed relative to the orientation of the housing of the joint module actuator. Similarly, at least one band (not shown) wraps around the third and fourth pulleys such that when the second pitch link 356b rotates, the instrument driver orientation remains fixed relative to the orientation of the first pitch link 356a. In sum, rotation of the first pitch link 356a around Axis G is transformed through the system of pitch links, pulleys, and bands into rotation of the instrument driver around Axis G'. In alternative embodiments, the pulleys may be engaged with cables, belts, and/or other suitable driving members.

The bands connecting the first and second pulleys 310 and 312, and the third and fourth pulleys 314 and 316, should be appropriately tensioned in order to facilitate the transformation of rotational motion described above. Accordingly, the pitch assembly 356 may further include a tensioning assembly. For example, the tensioning assembly can include at least one tensioner pulley located in plane with the first and second pulleys 310 and 312 and corresponding bands, and at least one tensioner pulley located in plane with the third and fourth pulleys 314 and 316 and corresponding bands. The in-plane locations of the tensioning pulleys may be adjusted and set (e.g., with fasteners) in order to calibrate the tension of the bands. However, the pitch assembly 356 may include a turnbuckle, or any suitable tensioning assembly. The bands may be tensioned to a predetermined tension level during assembly of the pitch assembly, and monitored and re-tensioned during and over the course of use of the robotic arm. Alternatively, at least a portion of the pitch assembly may be swappable to be replaced with appropriately-tensioned pitch assembly parts, such as part of regular maintenance.

Exemplary variations of pulley arrangements (e.g., assemblies for attachment of a driving member to a pulley, tensioning mechanisms, etc.) for the pitch assembly in a robotic arm are further described in detail in U.S. patent application Ser. No. 15/706,582 filed concurrently herewith and titled "BELT TERMINATION AND TENSIONING IN A PULLEY ARRANGEMENT FOR A ROBOTIC ARM", which is hereby incorporated in its entirety by this reference.

The instrument driver 180 may be configured to orient the surgical instrument within cannula 190, along instrument Axis H shown in FIG. 1C. The instrument driver 180 can, for instance, enable rotation of the instrument around Axis H and translation along Axis H, thereby providing two additional DOFs. An alternative way of expressing a two DOF of redundancy may be to include the rotation of the instrument shaft around Axis H (a DOF residing in the instrument driver) with the seven DOF from the first and second arm segments for a total of eight DOF for the robotic arm including the instrument driver, then consider the purpose of the robotic arm to position a vector (the surgical instrument) in space as a six DOF task. Therefore, the eight DOF available to perform such a six DOF task results in two redundant degrees of freedom. The intersection of the spherical roll Axis F, offset pitch Axis G', and the instrument axis H defines the mechanical remote center of motion ("RCM") for the surgical instrument within cannula 190. Generally, the mechanical RCM may closely coincide with the port placement for the surgical instrument (e.g., cannula 190 couples to the port).

Figure 4:
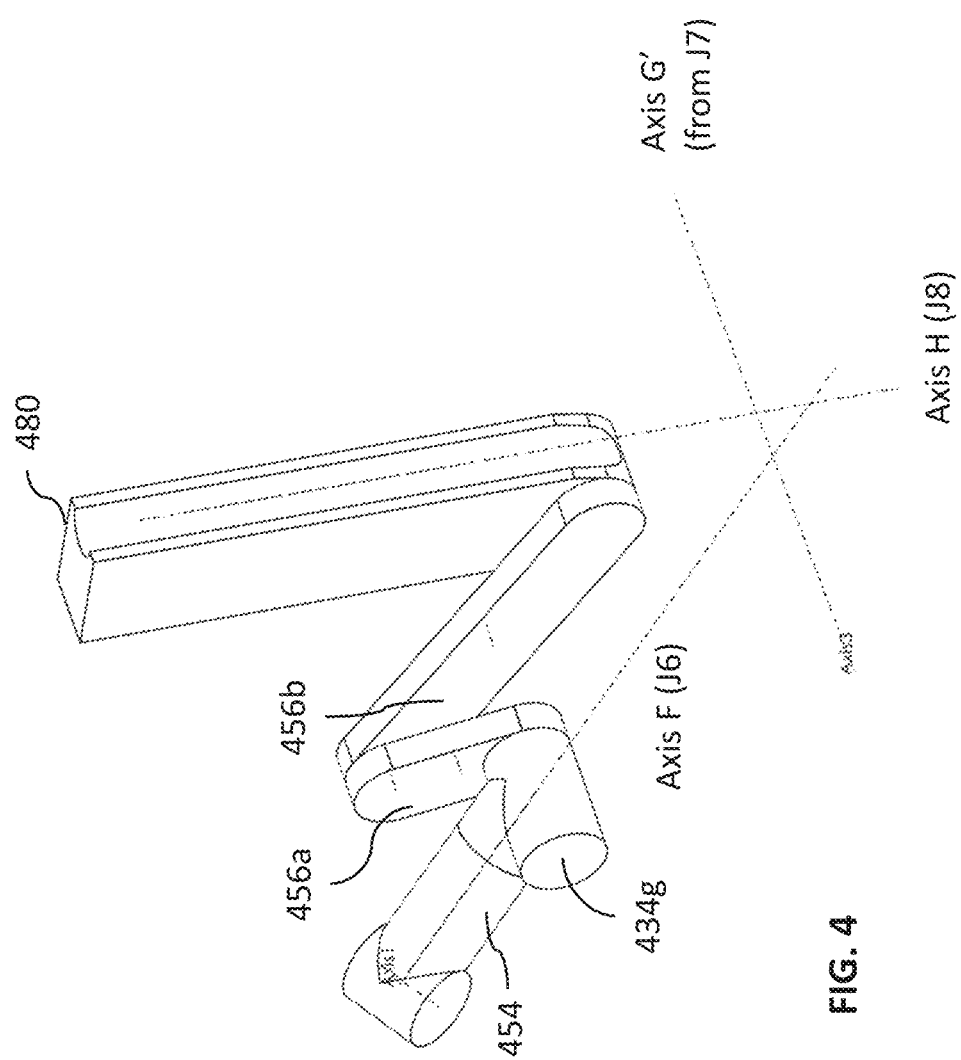
FIG. 4 is a schematic illustration of another variation of a spherical pitch assembly for a robotic arm with offset spherical roll, spherical pitch, and instrument rotation axes.

In another variation, as shown in FIG. 4, at least some of the rotational axes of the second arm segment (spherical arm) do not intersect at a common point, in contrast to the variation shown in FIGS. 1D and 1E. Rather, the links in the spherical arm may be configured such that Axis F (a spherical roll axis about which the spherical roll link 454 rotates), Axis G' (a spherical pitch axis, about which motion is remotely controlled by the joint module 434g with pitch links 456a and 456b), and Axis H (an instrument rotational axis about which the instrument driver 480 axially rotates the instrument) generally meet in a common region but are offset from one another by a predetermined distance (e.g., between about 1-5 centimeters, or between about 2-4 centimeters, or about 3 centimeters). In some variations, the instrument axis (Axis H) may intersect at an RCM, while the roll axis (Axis F) and/or the pitch axis (Axis G') does not intersect the RCM. For example, the roll axis and/or the pitch axis may be offset by about 5 centimeters or less from the remote center of motion, or about 2 centimeters or less from the remote center of motion. Various lengths of the arm links may be adjusted to accomplish this offset (e.g., shorter first pitch link 456a).

For example, to move the surgical instrument about the same point in 3D space as if that point were a mechanical RCM, a control algorithm for the arm calculates suitable actuation of some or all joints in the arm (including in the first segment, or Cartesian arm) during commanded motions of the instrument, in order to compensate for the axis offsets. For example, in some variations, the offset between a roll axis (Axis F) and an instrument axis (Axis H) may be about 2 centimeters. If the spherical roll link 454 rotates around the roll axis about 90 degrees clockwise as viewed in FIG. 4, the first segment with joints J1-J5 (e.g., Cartesian arm as described above) may collectively move to translate the spherical roll link 454 along an arc with an endpoint about 2 cm up and about 2 cm to the right (as viewed from the perspective of FIG. 4) in order to compensate for the axis offsets and maintain the same effective RCM. Specific rotational movements of each joint J1-J5 may depend on the specific pose of the robotic arm at the time of such motion.

In some areas, the control algorithm for compensating for the offsets may be similar to that implemented in the virtual RCM control mode described in further detail below. Accordingly, a compact arm design may be achieved without sacrificing the ability to maintain desired arcuate range of motion about an effective RCM during teleoperation. One benefit of a robotic arm that embodies these offset spherical roll, spherical pitch, and/or instrument rotation axes is that the robotic arm may be configured to more compactly collapse into a folded configuration. Such a compact configuration may be desirable, for example, for efficient storage under the patient table (or in another suitable storage location, such as in a mobile cart), such that the robotic arm does not impede or otherwise limit the range of motion (e.g., tilting) of the table, nor obstruct imaging fields of view (e.g., medical imaging such as CT scans). Additionally, as described above, in a robotic arm arrangement in which at least one of a spherical roll axis, a spherical pitch axis, and an instrument rotation axis is offset, a reduced workspace volume may be required for the pitch assembly to operate, as a shorter pitch link will sweep a smaller volume throughout its rotation.

In some variations, as shown in FIGS. 5A-5C, a robotic arm 500 may include a first segment 510 having a proximal end and a distal end, a second segment 550 having a proximal end that is coupled to the distal end of the first segment 510 and further has a distal end, and an instrument driver 580 coupled to the distal end of the second segment 550 and configured to hold and actuate a surgical instrument passing through a cannula. The first and second segments 510 and 550 may generally be similar to first and second segments 110 and 150 described above, with elements numbered similarly to that shown in FIGS. 1A-1C, except as described below. For example, similar to the robotic arm described above with reference to FIGS. 1A-1C, the first segment 510 may include a plurality of links providing at least five degrees of freedom, and the second segment 550 may include a plurality of links providing at least two degrees of freedom.

The first segment 510 may be configured to move the location of a workspace within which the second segment 520 moves. Furthermore, in the variation shown in FIG. 5A, at least some of the longitudinal axes of the first segment 510 may be offset from the joints between adjacent links. For example, the longitudinal axis of the shoulder roll link 516 and/or the longitudinal axis of the elbow link 518 may be laterally offset from the center of joint J3 (e.g., elbow joint). This lateral offset may, for example, enable the shoulder roll link 516 and the elbow link 518 to fold against each other more compactly. A suitable lateral offset may be, for example, a distance to about a quarter of the diameter (or about half the radius) of the link. Similarly, lateral offsets of other links in the robotic arm relative to adjacent joint(s) may be included to further enable a compact, folded configuration of the robotic arm.

As shown in FIGS. 5B and 5C, the second segment of the robotic arm 500 may include a spherical base link 552, a spherical roll link 554 coupled to the spherical base link 552, a first pitch link 556a having a proximal end coupled to a distal end of the spherical roll link 554, and a second pitch link 556b having a proximal end coupled to a distal end of the first pitch link 556a.

The spherical roll link 554 may include a proximal portion 554a and a distal portion 554b coupled to the proximal portion 554a. As shown in FIGS. 5A-5C, the proximal and distal portions 554a and 554b of the spherical roll link 554 may be generally cylindrical and aligned along respective longitudinal axes. The proximal and distal portions 554a and 554b may have similar diameters. However, in other variations the proximal and distal portions 554a and 554b may have any suitable shape (e.g., prismatic, irregular, etc.). The proximal portion 554a and the distal portion 554b may be integrally formed (e.g., through injection molding, machining from a common piece, etc.) or may separately formed and coupled to one another (e.g., via fasteners, welding, or other joining). A bridge portion or the connecting feature may facilitate translational and/or angular offsets between the proximal and distal portions 554a and 554b, as described below.

The proximal portion 554a may be oriented along a roll axis of the spherical roll link 554, such that rotation of the proximal portion 554a relative to the spherical base link 552 provides motion of the instrument driver 580 around a spherical roll axis (e.g., similar to Axis F shown in FIG. 1C). The distal portion 554b of the spherical roll link 554 may be oriented along a remote angled axis (e.g., similar to Axis G shown in FIG. 1C) that is correlated to a pitch axis (e.g., similar to Axis G'), where the angled axis is in a different plane than the spherical roll axis. For example, the remote angled axis may be an axis around which a parallelogram (formed at least in part by the first and second pitch links 556a and 556b) moves. In the robotic arm 500 pictured in FIGS. 5A-5C, the distal portion 554b (and its remote angled axis) is neither orthogonal nor parallel to the proximal portion 554a (and its spherical roll axis).

In some variations, the proximal portion 554a and the distal portion 554b may be offset in one or more directions (e.g., at least two directions). For example, the distal portion 554b may be translationally offset in a first direction from the proximal portion 554a (e.g., as shown in the side view perspective shown in FIG. 5A). The translational offset in the first direction (e.g., as measured between the longitudinal axes of the proximal portion 554a and the distal portion 554b) may be, for example, between about 1 and about 2 times the diameter of the proximal portion 554a or the distal portion 554b, between about 1 and about 1.75 times the diameter of the proximal portion 554a or the distal portion 554b, or between about 1 and about 1.5 times the diameter of the proximal portion 554a or the distal portion 554b.

Additionally or alternatively, the distal portion 554b may be angularly offset in a second direction from the proximal portion 554a (e.g., as shown in the top view perspective shown in FIG. 5B and the front view perspective shown in FIG. 5C). For example, the angular offset between the longitudinal axis of the proximal portion 554a (e.g., spherical roll axis) and the longitudinal axis of the distal portion 554b (e.g., remote angled axis) may be an obtuse angle. As measured from a top view perspective (e.g., as shown in FIG. 5B), the angular offset in the proximal and distal portions of the spherical roll link may be, for example, between about 90 degrees and about 135 degrees, between about 90 degrees and about 125 degrees, or between about 90 degrees and about 105 degrees, etc. As measured from a front view perspective (e.g., as shown in FIG. 5C), the angular offset in the proximal and distal portions of the spherical roll link may be, for example, between about 90 degrees and about 135 degrees, between about 90 degrees and about 125 degrees, or between about 90 and about 105 degrees, etc. Accordingly, in the robotic arm 500 pictured in FIGS. 5A-5C, the non-orthogonality of the spherical roll axis and the remote angled axis of the distal portion 554b is achieved by translationally offset and angularly offset portions of the spherical roll link.

Alternatively, in some variations, the spherical roll link 554 itself may be oriented only along a spherical roll axis. In these variations, the first pitch link 556a may include a lateral angled projection coupled to the spherical roll link 554 in order to achieve its rotation around an angled remote axis. Additionally or alternatively in these variations, the first pitch link 556a may be coupled to the spherical roll link 554 via any suitable angled coupling (e.g., directly to a portion similar to proximal portion 554a of the spherical roll link). Accordingly, in these variations, the non-orthogonality of the spherical roll axis and the remote angled axis may be achieved by translationally offset and angularly offset coupled portions of the spherical roll link 554 and the first pitch link 556a.

The first pitch link 556a may be rotatable within a first plane, and the second pitch link 556b may be rotatable within a second plane. For example, the first and second planes may be generally offset and parallel to one another. The first and second pitch links 556a and 556b may generally be similar to the pitch assembly 156 described above. The instrument driver 580 may be coupled to a distal end of the second pitch link 556b such that the instrument driver is not parallel to at least one of the first and second planes (e.g., offset from a parallelogram formed at least in part by the first and second pitch links) and/or not parallel to at least a portion of the spherical roll link 554 (e.g., offset from the spherical roll axis).

One effect of non-orthogonality of the spherical roll axis (e.g., of at least the proximal portion 554a of the spherical roll link) and the remote angled axis (e.g., of the distal portion 554b of the spherical roll link) is that at least a portion of the pitch assembly may be angled relative to at least a portion of the spherical roll link 554 (e.g., a parallelogram formed at least in part by the first and second pitch links may be angularly offset from the roll axis). Accordingly, space between the pitch assembly and the spherical roll link 554 may be provided to enable another portion of the robotic arm and instrument assembly to nestle and further collapse into a more compact space. For example, as shown in FIGS. 5A-5C, at least the second segment 550 of the robotic arm 500 may be foldable into a compact configuration in which the instrument driver 580 is positioned between the spherical roll link 554 and at least one of the pitch links 556a and 556b, such as when the pitch links 556a and 556b are folded against each other and against the spherical roll link 554. Accordingly, the second segment 550 of the robotic arm may have a greater range of motion throughout folded and unfolded configurations made possible without physical interference between adjacent links, thereby providing for greater dexterity. Additionally, the offset nature of the spherical roll link, the pitch assembly, and the instrument driver may increase the robotic arm's general ability to fold into smaller volume, such as for storage and/or transport purposes.

In some variations, some or all of the links may include bumpers that may help protect portions of the robotic arm from damage in the event of collision with other links, other joint modules, other robotic arms, surgical assistants or other users, other surgical equipment (e.g., surgical table), and/or other nearby obstacles. The bumpers may additionally or alternatively help protect the robotic arm from damage during packaging and transport. In one embodiment, a bumper may include one or more flexible plates (e.g., thin metal sheets) covering a link, where the plate flexes and absorbs energy upon impact, thereby reducing impact energy transferred to underlying components. In other embodiments, the bumpers may include foam, rubber, inflatable sleeves or other coverings. The bumpers may substantially cover the entire length of the robotic arm, or may cover only selected portions of the robotic arm (e.g., selected links, joint modules). For example, one or more bumpers may cover only part of or the entire length of the spherical segment of the arm, only part of or the entire length of the Cartesian segment of the arm, or a portion of the Cartesian segment and a portion of the spherical segment. As another example, one or more bumpers may cover only some or all of the joint modules in the robotic arm. As yet another example, a bumper may substantially surround a portion of the arm (e.g., circumferentially around the arm) or may cover only part of the circumference of the arm (e.g., a sleeve with an arcuate cross-section). Some or all of the bumpers may be connected to sensors (e.g., pressure sensors, capacitive sensors, etc.) so that the robotic arm can sense occurrence of collisions and/or close approximation to objects in the environment (e.g., other robotic arms, table fixtures, personnel, etc.). Upon detection of a collision or an impending collision, a control system may automatically adjust control of the arm to halt motion in the current direction and/or move in a different direction to reverse or avoid collision.

Generally, each link may include an internal volume for receiving at least one joint module, and/or for passing wiring (e.g., for communication or power) along the length of the robotic arm. For instance, the links may be generally tubular structures. Links may be made of metal (e.g., aluminum, steel, etc.) or other suitable rigid material, and may include parts that are machined, casted, molded, and/or formed through any suitable manufacturing process. Furthermore, a link may include multiple link parts (e.g., shell portions) that are welded or otherwise fastened together to form a generally tubular structure.

Arm Configurations

The various links in the robotic arm may be arranged in any number of predetermined configurations for different purposes. For instance, a robotic arm (e.g., a variation with offset axes for spherical roll, spherical pitch, and instrument rotation, as described above with reference to FIG. 1F) may be arranged in a compact, folded configuration, such as for stowage under a surgical table, storage, and/or transport. The folded arm configuration may also incorporate the folding, retraction, or other compact storage of components coupled to the robotic arm, such as a table adapter coupling the robotic arm to a surgical patient table, cart, or other surface. FIGS. 6A and 6B illustrate an exemplary folded configuration of a robotic arm in more detail (e.g., a variation without offset axes for spherical roll, spherical pitch, and instrument rotation, as described above with reference to FIGS. 1A and 1B). Shoulder pitch link 614 and shoulder roll link 616 are coaxial to form a shoulder limb 615, and elbow link 618 and forearm link 620 are coaxial to form a forearm limb 619. In the folded configuration, the shoulder limb 615 and the forearm limb 619 may fold toward one another generally arranged in a first plane or "layer." The spherical base link 652 and spherical roll link 654 may fold against the forearm limb 619 such that the pitch assembly (pitch links 656a and 656b) is generally arranged in a second plane or "layer." The instrument driver 680 may be tucked between the first and second "layers."

Figure 7A:
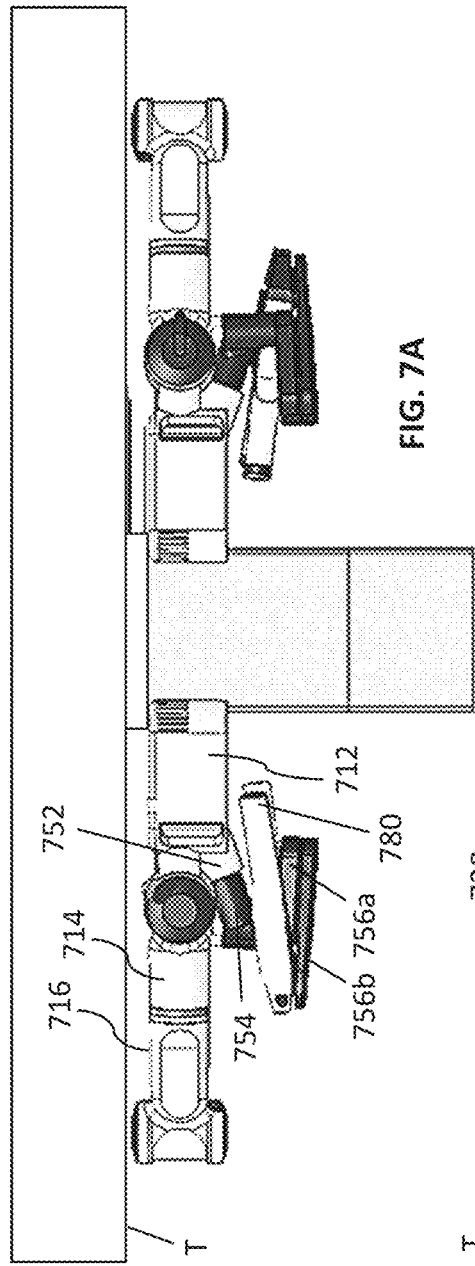
FIGS. 7A and 7B are side and bottom views of a robotic surgical system including a plurality of robotic arms in a folded configuration and coupled to a patient table.
Figure 7B:
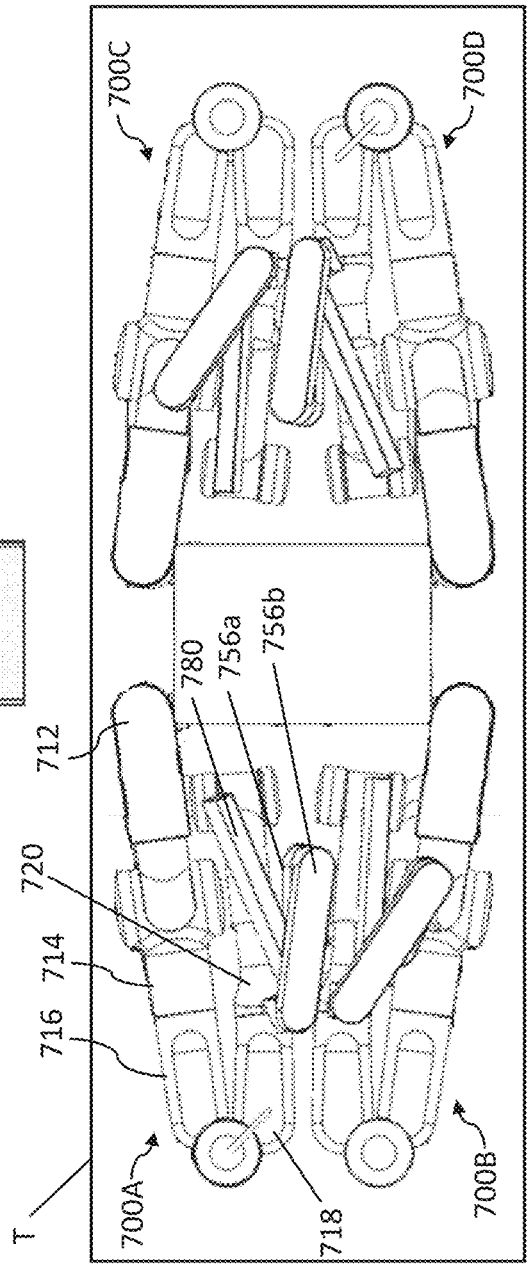

FIGS. 7A and 7B illustrate exemplary variations of robotic arms (similar to robotic arm 500 described above with reference to FIGS. 5A-5C) arranged in an exemplary folded configuration underneath a surgical patient table. This exemplary folded configuration may be used, for example, for storage and/or transport purposes. Referring to robotic arm 700A in FIG. 7B, in some variations, a robotic arm may include a base link 712 configured to couple to a table T, such as with pins or other suitable adapter. The base link 712 may, for example, couple to a column support of the table T that grounds the table T to the floor. The robotic arm may include a shoulder pitch link 714 coupled to the base link 712, and a shoulder roll link 716 coaxial with and coupled to the shoulder pitch link 714. An elbow link 718 is pivotally coupled to the shoulder pitch link 714 such that a forearm portion of the robotic arm (including elbow link 718 and forearm link 720) is foldable against the shoulder portion (including shoulder pitch link 714 and shoulder roll link 716) of the robotic arm. For example, the forearm portion of the robotic arm may be generally doubled-back on the shoulder portion of the robotic arm, with the shoulder portion and the forearm portion of the robotic arm generally located in the same plane or "layer." As best shown in FIG. 7A, the spherical base link 752 (which is coupled to the forearm link 720) may be oriented at an angle out of plane from the shoulder portion and the forearm portion. At least the rest of the spherical arm segment of the robotic arm, including the spherical roll link 754 (which is coupled to the spherical base link 752), the first pitch link 756a, and the second pitch link 756b, may arranged out of plane from the shoulder portion and the forearm portion of the robotic arm. For example, at least a proximal portion of the spherical roll link 754 may be coaxial with the spherical base link 752 to continue out of plane from the more proximal portions of the robotic arm. The first and second pitch links 756a and 756b may be arranged below the plane of the shoulder and forearm portions of the robotic arm. The instrument driver 780 may be tucked or collapsed between the spherical roll link and at least one of the first and second pitch links 756a and 756b, in a manner similar to the spherical arm segment configuration described above with reference to FIGS. 5A-5C. In some variations, for example, the stowage configuration of an arm shown in FIGS. 7A and 7B may occupy a volume of generally between about 8 and about 12 inches high (along the vertical height of the table), between about 8 and about 12 inches wide (along the width of the table), and between about 18 and 22 inches long (along the longitudinal length of the table). In one exemplary variations, for example, the stowage configuration of an arm may occupy a volume of about 10 inches high, about 10 inches wide, and about 20 inches long.

Although FIG. 7B depicts four robotic arms 700A, 700B, 700C, and 700D arranged in a 2×2 arrangement (i.e., so each robotic arm services or is coupled to a respective quadrant of the table T), it should be understood that a robotic surgical system may include fewer (e.g., one, two, or three) or more (four, five, six, etc.) robotic arms arranged in any suitable manner. Furthermore, in some variations one or more of the robotic arms may be permanently coupled to the table, while in other variations one or more of the robotic arms may be removably coupled to the table. For example, at least part of the system may be modular, with one or more of the robotic arms selectively removable and/or rearrangeable). Exemplary variations of coupling mechanisms to couple a robotic arm to a patient table are described in further detail in U.S. patent application Ser. No. 15/706,112 filed concurrently herewith and titled "LINKAGE MECHANISMS FOR MOUNTING ROBOTIC ARMS TO A SURGICAL TABLE", and U.S. patent application Ser. No. 15/706,087 filed concurrently herewith and titled "TABLE ADAPTERS FOR MOUNTING ROBOTIC ARMS TO A SURGICAL TABLE", each of which is incorporated in its entirety by this reference.

During use in a surgical procedure, a robotic arm may facilitate instrument reach in a wide variety of workspace regions by being configurable in a range of poses. For example, the robotic arm may be configurable in a "low" (or "tucked") arm position, a "high" arm position and a "flipped" arm position. Between the "low" arm position (or the "high" arm position) and the "flipped" arm position, the instrument driver can revolve entirely around the arm such that the weight of the instrument driver may be supported by the arm from different directions. For instance, as shown in FIG. 8A, in a "low" arm position, the robotic arm 800 may support the instrument driver 880 from below the instrument driver (with the arm 800 located at the side of and/or under the patient table or cart, or with at least some of the Cartesian arm located below the base link. Similarly, in a "high" arm position, the robotic arm 800 may similarly support the instrument driver from below the instrument driver (but with the robotic arm generally located above the patient table or cart). In the "low" and "high" arm positions, at least part of the robotic arm (e.g., at least a portion of the Cartesian arm) may be folded and/or positioned below the level of the patient, in order to position the arm below the instrument driver. As shown in FIG. 8B, in a "flipped" arm position, the robotic arm 800 may support the instrument driver 880 from above the instrument driver. In the "flipped" arm position, most of the robotic arm 800 may be extended and/or positioned above the level of the patient, in order to position the arm above the instrument driver. The robotic arm may additionally be positioned in other arm positions intermediate between the "low" or "high" arm positions and the "flipped" arm position, to position the instrument driver anywhere within a 360-degree revolution around the arm. Furthermore, in order to improve clearance of the instrument driver relative to the arm, at least some of the arm links (including, for example, the shoulder pitch link, the shoulder roll link, the elbow link, and the forearm link) may be curved. For instance, as shown in FIG. 1B, at least the elbow link 118 and forearm link 120 may form a forearm link that has a concave surface, where the concavity generally faces the workspace of the instrument driver.

In some variations, the robotic arm may be configured in any of a plurality of template poses correlated with surgical procedure types. Different port placements (i.e., where surgical instruments may enter the patient through a cannula) are generally preferred for different types of laparoscopic procedures. For instance, a particular surgical procedure may require at least a first port in a specific location in a lower right quadrant of the patient abdomen and a second port in another specific location in an upper left quadrant of the patient abdomen. Additionally, there may be different locations around the patient where surgical assistants are best located to assist during the procedure (e.g., manipulate one or more robotic arms, monitor the patient). A template for this procedure may include posing a first robotic arm in a "low" arm position to enable the first robotic arm to reach the first port, and a posing a second robotic arm in a "high" arm position to enable the second robotic arm to reach the second port. The base links of the first and second robotic arms may be mounted in suitable locations around the patient table to accommodate the surgical assistants. In other words, the collective arrangement and poses of the robotic arms may form a template configuration for a particular surgical procedure, which may be slightly customized or otherwise adjusted for particular patients (e.g., adjusting for patient characteristics such as height, girth, weight, sex, etc.). In some variations, template poses or other poses (e.g., "low" arm position, the "high" arm position, and/or the "flipped" arm position), and the associated joint angular positions in the arm, etc. may be stored in a memory device (e.g., hard drive) and recalled from the memory device when desired to move the arm to a stored pose. Furthermore, in some variations, a particular pose may be achieved (e.g., by actuator control and/or manual movement of the robotic arm), and a set of joint angular positions in the arm that are associated with the particular pose, may be stored to a memory device upon a user input of a save command, etc. Such a stored pose may be recalled in the future to reposition the arm.

Joint Modules

As described above, relative movement between adjacent arm links is generated by one or more joint modules. In some variations, a joint module may include a joint module including a servomotor or other suitable motor. Generally, each joint module may include one motor, or multiple motors (e.g., with a differential gear drive to combine the individual motor outputs). Additionally, the actuator assemblies may include a gearbox coupled to the motor output, such as a harmonic drive, planetary gearbox, cycloidal drive, etc. to increase overall torque output. A joint module may further include at least one sensor (e.g., encoders) that detects and provides feedback on the rotational position of the actuator. Generally, a joint module is designed to be robust, lightweight, and compact, so as to contribute to a robotic arm that is similarly robust, lightweight, and compact in view of physical space restrictions and medical device requirements. Additionally, the joint module may include at least one seal circumferential around the rotor shaft, which functions to retain lubrication inside the gearbox. Such seals ideally have a low and consistent amount of friction on the rotor shaft, so as to not significantly interfere with the actuation by the joint module.

In some variations, at least some of the joint modules may include a module assembly having a first housing including a motor portion, a second housing including a load (high-loaded) portion, and a third housing including an electronics portion. The joint module may combine the multiple housings in a modular manner that is simple to build and maintain. For example, as shown in FIGS. 9A and 9B, a joint module 900 includes a first housing with a motor portion 910, a second housing including a load portion 920 coupled to a first end of the motor portion 910, and a third housing including an electronic portion 930 coupled to a second end of the motor portion 910. The third housing may further include a cover 940 configured to enclose the electronics within the third housing. The various housings may be coupled to one another with removable fasteners 952 (e.g., screws) that bind coupling features 954 as shown in FIG. 9A, such that the fasteners 952 may be removed to disassemble the housings of the joint module, such as for maintenance. Alternatively, the housings may be coupled to one another with other suitable mechanisms, such as mechanical locks or snaps. The assembly of the housings for the load portion, the motor portion, and the electronics portion may further be enclosed in a module housing 940, which may be accessible by removable cover 942.

The motor portion 910 of the joint module may include various components associated with the motor, such as a stator and a rotor (e.g., as in a servomotor), a safety brake (e.g., one of the variations described below, or another suitable fail-safe brake), an encoder for measuring rotational position of the motor, bearings, etc. In embodiments in which the gearbox coupled to the motor output includes a harmonic drive, the motor portion 910 may include a harmonic drive wave generator. As shown in FIG. 9C, the motor portion 910 may be easily removable from the load portion 920 (e.g., in a modular fashion). Additionally, at least one seal may be present in the motor portion 910, such as a labyrinth seal that retains lubrication via a tortuous passageway and is inherently low-friction by nature of being non-contact with the rotor.

As shown in FIG. 9B, the load portion 920 of the joint module may include highly-loaded components, such as an output bearing, spline components 922 of a harmonic drive (e.g., circular spline and flex spline) or other portions of a gearbox, mechanical joint limits for restricting range of motion of the adjacent actuated links, etc. Other suitable components following the direct output of the motor portion may be included in the load portion 920 housing. As described above, the load portion 920 may be easily removable from the rest of the joint module.

Figure 9D:
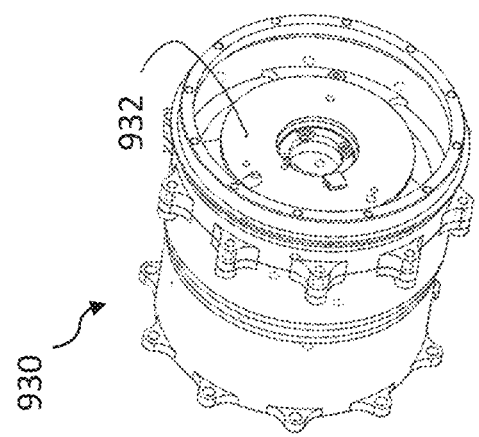
FIG. 9D is a perspective view of an exposed electronics housing in the joint module depicted in FIG. 9A.
Figure 9C:
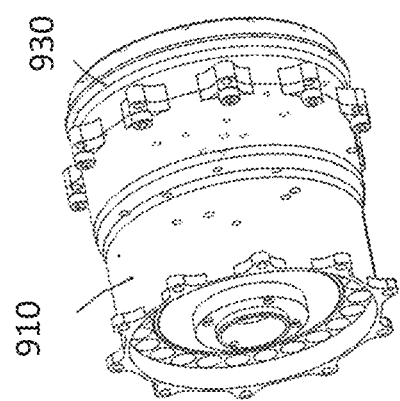
FIG. 9C is a perspective view of the motor portion and electronics housing in the joint module depicted in FIG. 9A.
Figure 9B:
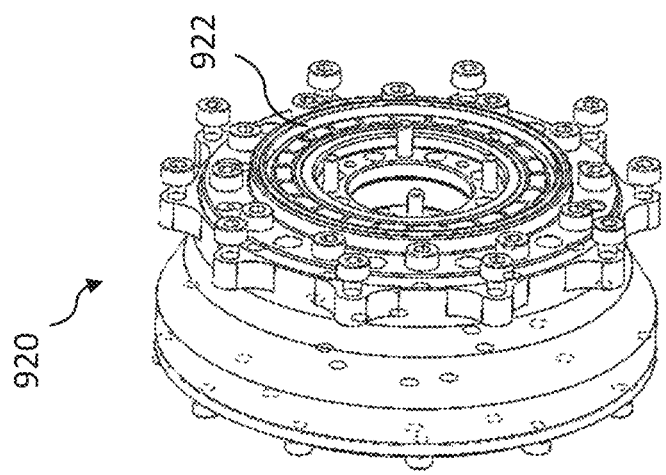
FIG. 9B is a perspective view of a high load portion of the joint module depicted in FIG. 9A.

As shown in FIG. 9D, the electronics portion 930 of the joint module may include various electronics associated with and coupled to the motor. For example, the electronics portion 930 may include motor drivers and/or signal processors on a circuit board 932, located at a rear end of the motor within the housing for electronics portion 930. Access to the electronics may be achieved by disassembling at least part of the module housing 940, such as by removing the rear cover 942 (e.g., removing fasteners).

Though the various joint modules in the robotic arm may generally have the same modular structure as shown in FIGS. 9A-9D, different joint modules in the robotic arm may have different sizes (e.g., different ratings and dimensions of the motor) depending on the space limitations and/or torque requirements at each joint in the robotic arm. To fit within an arm link or elsewhere in the robotic arm, the joint module may have a generally cylindrical profile so as to be sized within a suitable link.

Safety Brakes

One or more of the joint modules may include a safety brake or fail-safe brake that halts movement of the joint module, as well as the arm links connected by the joint module, in the event of actuator failure. For instance, actuator failure may be caused by loss of power (e.g., due to circuitry faults, failure of the main power supply), or loss of electrical current used to drive the actuators in the joint modules. Another example of a failure is discrepancy between the multiple encoder sensors that are used to measure rotational position of the actuator output or joint in a single joint module, which may indicate, for example, possible slipping of a mechanical component. Since the robotic arm requires power to operate, any sudden loss of that power may result in at least a portion of the robotic arm collapsing due to gravity or other external forces. Collapse of the robotic arm can result in injury to the patient if the failure occurs during a surgical procedure, injury to nearby operators of the robotic-assisted surgical system, damage to the robotic arm or surgical instruments, and/or damage to other surrounding equipment and surroundings. A fail-safe brake, which applies a braking force to the actuator in the event of a failure, may help reduce the undesirable consequences of actuator failure and/or other system fault.

In some variations, the safety brake may be configured to be overridden manually by a user, to enable movement of the robotic arm despite the activation of the safety brake. For example, in an instance in which system fault has occurred, the robotic arm may have to be removed from the operating field. However, such removal requires command control of the robotic arm (which may not be possible due to the system fault) and/or manual brute force (which may not be possible due to the fail-safe brakes locking the arm joints in place). Accordingly, the robotic arm may include mechanisms for overriding the safety brake. For example, the safety brake may be overpowered with manual force from a user, which may or may not be amplified with a gearbox or a mechanism for increasing leverage, etc. In one variation, the robotic arm may include an access panel (e.g., near one or more joint modules) that provides access, such as with a special tool or crank, for manually overpowering the safety brake (e.g., by manually powering the rotor in the joint module). Additionally or alternatively, the safety brake may be disengaged such as with a button or handle, though in some variations the location of such disengaging mechanisms may be limited to locations where the user is likely to be able to manually prevent collapse of the arm (e.g., near the distal end, where the user need only support the weight of the instrument driver, etc.).

Preferably, a safety brake is lightweight, compact, and generates relatively little heat (or a low temperature) when activated and engaged. Generally, a safety brake has a "brake on" mode and a "brake off" mode. In some variations, the brake may be a biased brake (e.g., spring-applied brake or permanent magnet brake) that is mechanically biased in the "brake on" mode and requires some force to maintain the brake in the "brake off" mode, meaning that the "brake on" mode is engaged in the event of a power failure. In other variations, the brake may be a bi-stable brake actuated by a secondary actuator that is powered by a stored energy source (e.g., capacitor or battery). In the event of power failure, the stored energy source quickly releases its stored energy to the secondary actuator, which engages the "brake on" mode. Exemplary variations of fail-safe brakes are described below in detail.

Bi-Stable Brakes

As described above, a bi-stable brake is actuated by a secondary actuator that is powered by a stored energy source (e.g., capacitor or battery). One example of a secondary actuator is shown in FIGS. 10A-10G. As shown in FIG. 10A, an exemplary stepper and coil brake actuator assembly for a bi-stable brake includes a magnet 1020 having a magnetic field, a driven element 1030 magnetically attracted to the magnet 1020, a coil 1040 configured to selectively cancel the magnetic field, and at least one capacitor 1054 configured to activate the coil 1040 to cancel the magnetic field. The magnet 1020 may, for example, include a permanent magnet with features (e.g., prongs) that can be suitably internal to the coil 1040 such that the coil 1040, when activated, cancels the magnetic field. The driven element 1030 may be made of a suitable magnetic material, such as iron.

The secondary actuator assembly may additionally include a stepper motor 1010 or other suitable actuator driving a leadscrew 1012 with a nut 1014 that travels on the leadscrew 1012 and engages the magnet 1020 (e.g., with pins). A PCB 1050 or other electronics assembly may additionally be provided for controlling and triggering the secondary assembly. The PCB 1050 may, for example, include a driver for the stepper motor 1010, the one or more capacitors 1054 (e.g., tantalum capacitor, ceramic capacitor, etc.) or one or more small batteries, at least one switch transistor, status sensors 1056a and/or 1056b, status indicator LEDs, other control elements etc. Redundant elements on the PCB 1050, such as multiple capacitors and/or multiple batteries (including a backup battery) may be provided.

During normal or typical operation of a joint module, the secondary actuator is as shown in FIG. 10C in a "brake off" mode. The coil 1040 is not activated, thereby permitting the magnetic field from magnet 1020 to keep driven element 1030 close (e.g., "parked" or locked by the passive magnetic field). In this state, energy is stored in the one or more capacitors 1804. A status sensor 1056a may detect that the driven element is positioned according to a "brake off" mode. As shown in the control schematic of FIG. 10B, the PCB 1050 may continually monitor and compare the provided power (e.g., 24V or 48V) to a trigger threshold level (e.g., 15V). Software may send a "brake off" command or signal periodically with high frequency (e.g., every 1 millisecond) as long as the monitored power is above the trigger threshold level. Additionally or alternatively, the status sensors 1056a and/or 1056b may verify position of the stepper motor and status of brake actuation. For example, the status sensor 1056a may be an opto-reflective or magnetic sensor that detects whether the magnet 1020 (or nut 1014, etc.) is in the position corresponding to the "brake off" mode.

A power failure may be indicated when the PCB 1050 fails to send the "brake off" command or signal because the system power is below the trigger threshold level. In the event of an indicated power failure (or an intentional brake command), circuitry on the PCB 1050 automatically triggers the one or more capacitors 1054 to release their stored energy, such as passively through a switch transistor on the PCB, to activate the coil 1040 which normally cancels the magnetic field. Once the coil 1840 is activated, the driven element 1020 is freed from the magnet 1020, as shown in FIG. 10D. The driven element 1020 may travel a predetermined distance (e.g., governed by a spring) to in turn actuate a component of the overall bi-stable brake.

The secondary actuator assembly may re-arm itself to return to the configuration shown in FIG. 10C. As shown in FIG. 10E, the stepper motor 1010 may rotate the leadscrew 1012 to drive the nut 1014, the magnet 1020 (which is engaged to the nut 1014 with pins or other suitable attachment mechanism), and/or coil 1040 distally toward the freed driven element 1020. Since at this point the coil has expended its energy received from the capacitors and no longer cancels the magnetic field, the magnetic field of magnet 1020 may be used to capture the driven element 1020 (FIG. 10F). As shown in FIG. 10G, the stepper motor 1010 may then drive the leadscrew in a reverse direction to cause the nut 1014, magnet 1020, driven element 1020, and coil 1040 to move back to the "brake off" configuration. Alternatively, another suitable mechanical feature (e.g., spring) may be used to fetch the driven element 1020 and return it to the "brake off" configuration. Once these components are back in the "brake off" position, the status sensor 1056a, located near a proximal end of the lead screw, may verify presence (and/or status sensor 1056b, located distally relative to the motor, may verify absence of the components) to confirm status of the brake system as in the "brake off" position.

Figure 11A:
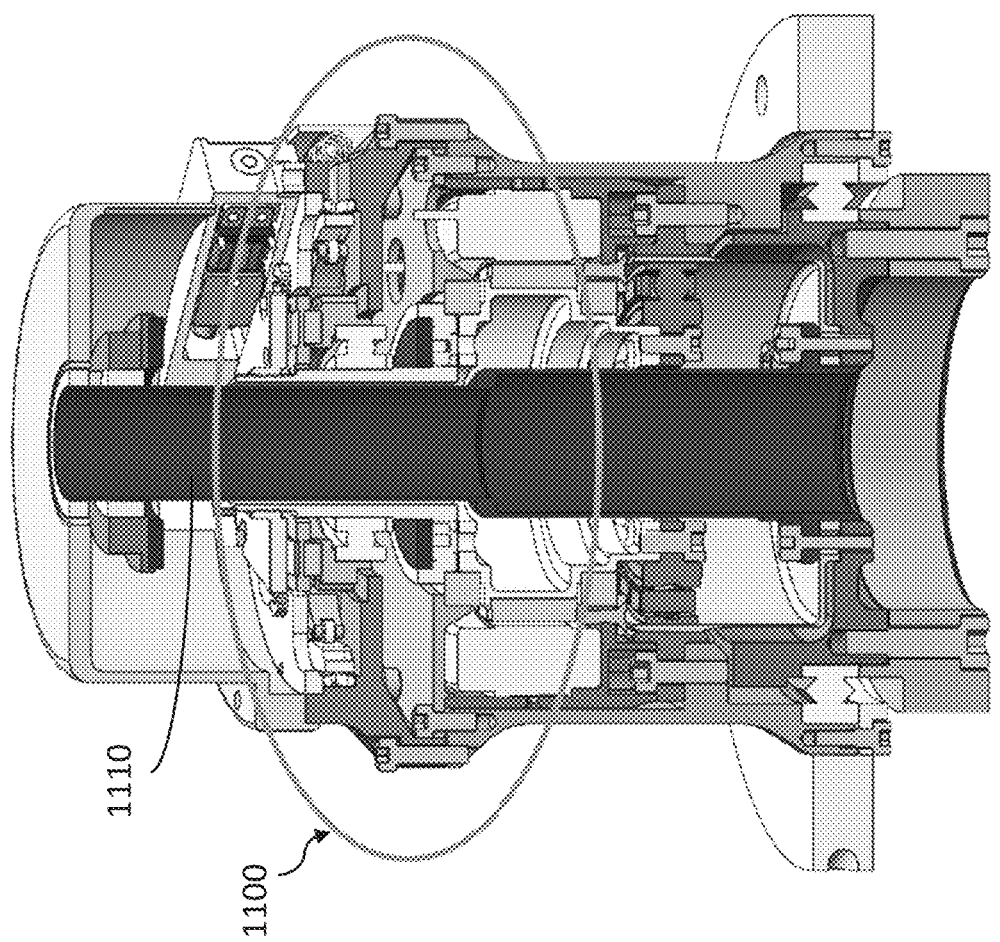
FIG. 11A is a longitudinal cross-sectional view of an exemplary joint module with one variation of a bi-stable safety brake.

One variation of a bi-stable safety brake, which may, for example, be paired with the secondary actuator 1000 described above, is shown in FIGS. 11-13. As shown in FIG. 11A, a ratchet safety brake module 1100 may be disposed in a joint module around rotor 1110, such as between encoders and control PCB boards in the joint module.

Referring to FIGS. 11B-11F, the driven element of secondary actuator 1000 may be coupled to one end of a tension spring 1124, while the other end of the tension spring 1124 may be coupled to a pin 1122. Pin 1122 is integral with or coupled to a cam wheel or ring 1120 disposed within the safety brake module 1100. The safety brake module 1100 may further include spring-biased and pivoting pawls 1130, which have rollers 1132 articulating on an internal surface of the cam wheel 1120. Each of the pawls 1130 also includes a tip 1134 configured to engage a ratchet wheel 1140. Ratchet wheel 1140 is disposed around the rotor 1110 via bearing 1142. As shown in FIG. 11E, also disposed around the rotor is a pressure nut 1180 (a top plate or disc) which is threaded onto the rotor 1110. The pressure nut 1180 cooperates with ratchet wheel 1140 to compress a stack including a friction pad 1150, an intermediate pressure plate 1160, and a wave spring 1170. The degree of this compression is correlated with brake force, which is tunable during assembly by the position of the top plate 1162 along the rotor shaft. As shown best in FIG. 11F, the pressure plate 1160 includes keys 1162 that engage longitudinal grooves on the rotor shaft.

The safety brake module 1100 in a "brake off" mode is shown in FIGS. 12A-12C. As with other bi-stable brakes, no power is needed to hold this state. The secondary actuator 1000 engages a magnetic latch, such that the driven element in the secondary actuator 1000 is held magnetically to magnet 1020, thereby allowing the pin 1122 (attached to the driven element via spring 1124) and the cam wheel 1120 to maintain a "brake off" position. In this position, the rollers 1132 of pivoting pawls 1130 articulate with lobes on the internal surface of the cam wheel 1120, thereby keeping the pawl tips 1134 disengaged from the ratchet wheel 1140.

Figure 13B:
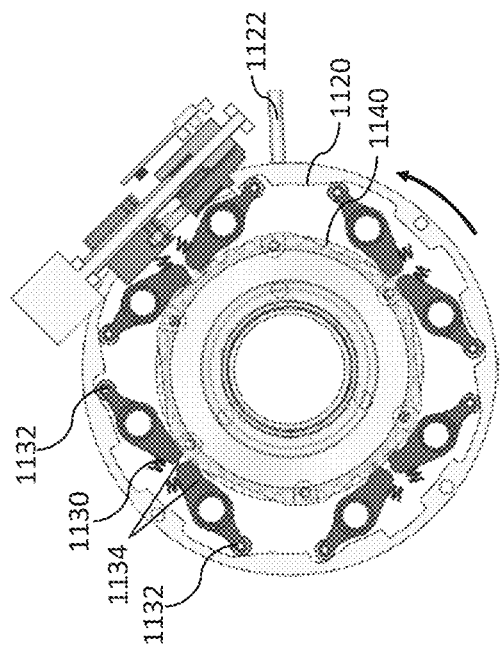
FIGS. 13A-13D are schematic illustrations of the brake depicted in FIG. 11A in a "brake on" mode.
Figure 13C:
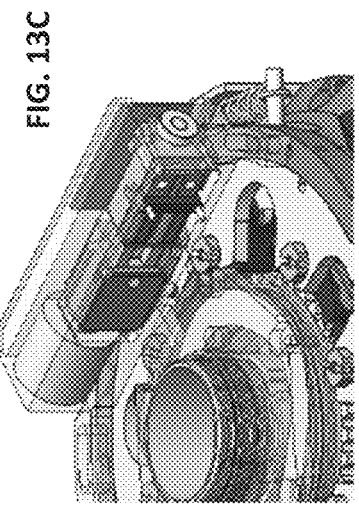
Figure 13A:
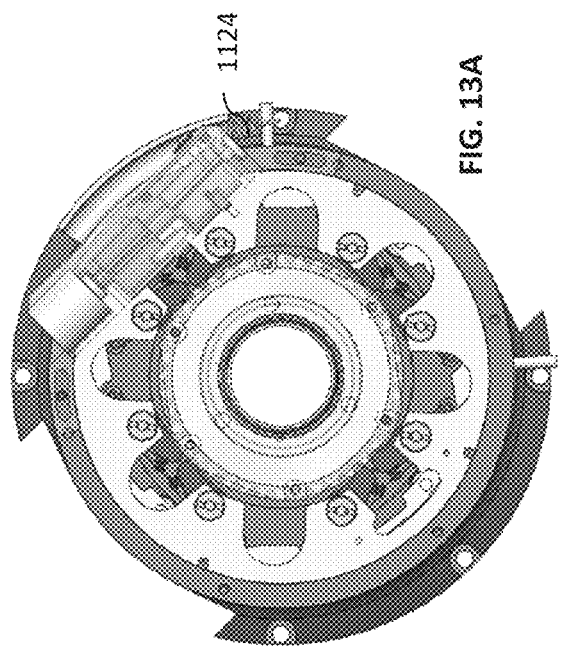
Figure 13D:
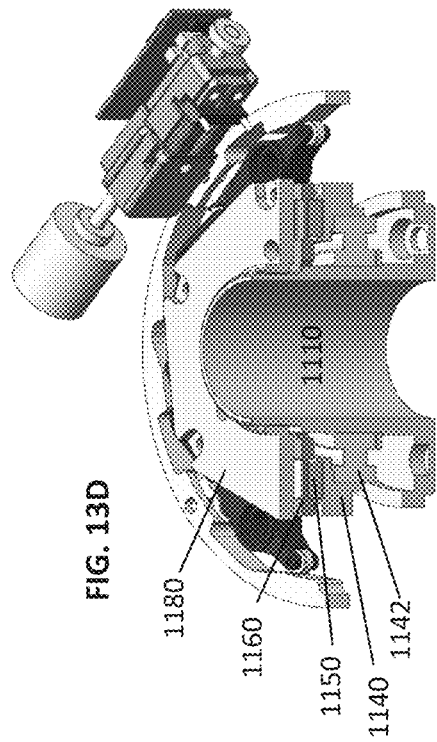

The safety brake module 1100 in a "brake on" mode is shown in FIGS. 13A-13D. In the event of power loss, the secondary actuator 1000 disengages the magnetic latch (as the driven element is released) and the spring 1124 abruptly pulls the cam wheel 1120 in rotation (in a counter-clockwise direction as shown in FIG. 13B). The spring-loaded pawl rollers 1132 articulate away from the lobes on the internal surface of the cam wheel 1120, thereby allowing the pawl tips 1134 to engage and stop rotation of the ratchet wheel 1140. When the ratchet wheel 1140 stops, the friction pad 1150 (located between the ratchet wheel 1140 and the pressure plate 1160) drags on the pressure plate 1160 to stop. Since the rotor is engaged with the axial keys 1162 on the pressure plate 1160, the rotor drags to a stop along with the pressure plate 1160, thereby halting the rotor and all actuation provided by the joint module. In this "brake on" mode, the safety brake assembly acts as a single setting clutch. No power is required to keep the brake in this "brake on" mode.

Subsequently, the safety brake module 1100 may be deactivated and returned to the "brake off" state. As described above with respect to FIGS. 10E-10G, the secondary actuator may be re-armed such that the magnetic latch is re-engaged. Re-engagement of the magnetic latch causes the cam wheel 1120 to rotate (in a clock-wise direction, opposite that depicted in FIG. 13B) and the pawls to pivot and disengage their tips 1134 from the ratchet wheel 1140. With the pawls disengaged from the ratchet wheel 1140, the ratchet wheel 1140 is free to rotate with the rotor on the bearing 1142. Again, no power is required to hold this "brake off" mode.

Figure 14B:
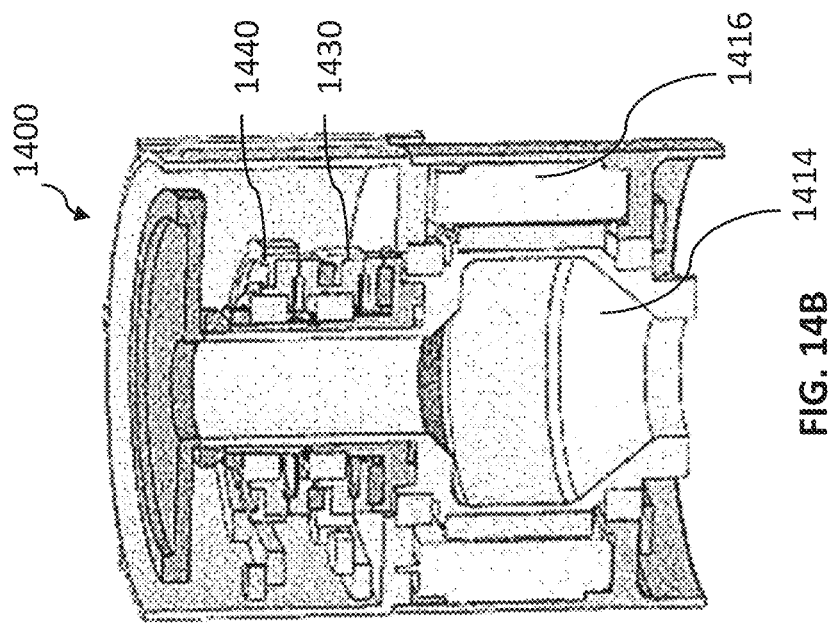
FIGS. 14A and 14B are perspective and longitudinal cross-sectional views, respectively of another variation of a bi-stable safety brake.
Figure 14A:
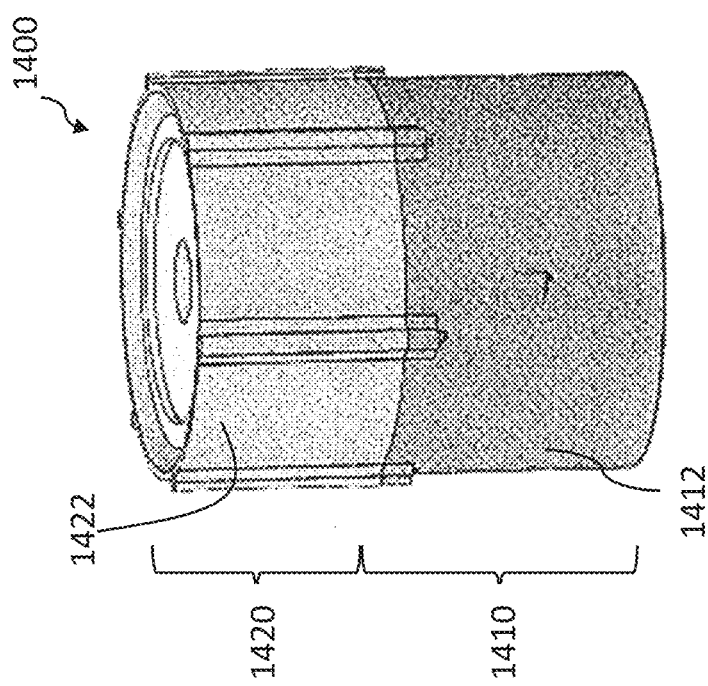

In another variation of a bi-stable safety brake, which may, for example, be paired with one or more instances of the secondary actuator 1000 described above, is shown in FIGS. 14A-14C. As shown in FIG. 14A, joint module 1400 may include a motor portion 1410 with motor housing 1412, and a brake portion 1420 with a brake housing 1422. As shown in FIG. 14B, the motor portion 1410 includes a rotor 1414 that spins and a stator 1416 that remains stationary.

Disposed around the rotor 1414 are two instances of a ratchet brake assembly similar to that described above with respect to FIGS. 12A-12C and 13A-13D. A first ratchet brake assembly 1430 may function as an arresting brake with high torque, while a second ratchet brake assembly 1440 may function as a clutch brake assembly with a low torque (lower than that for the first ratchet brake assembly 1430).

Figure 14C:
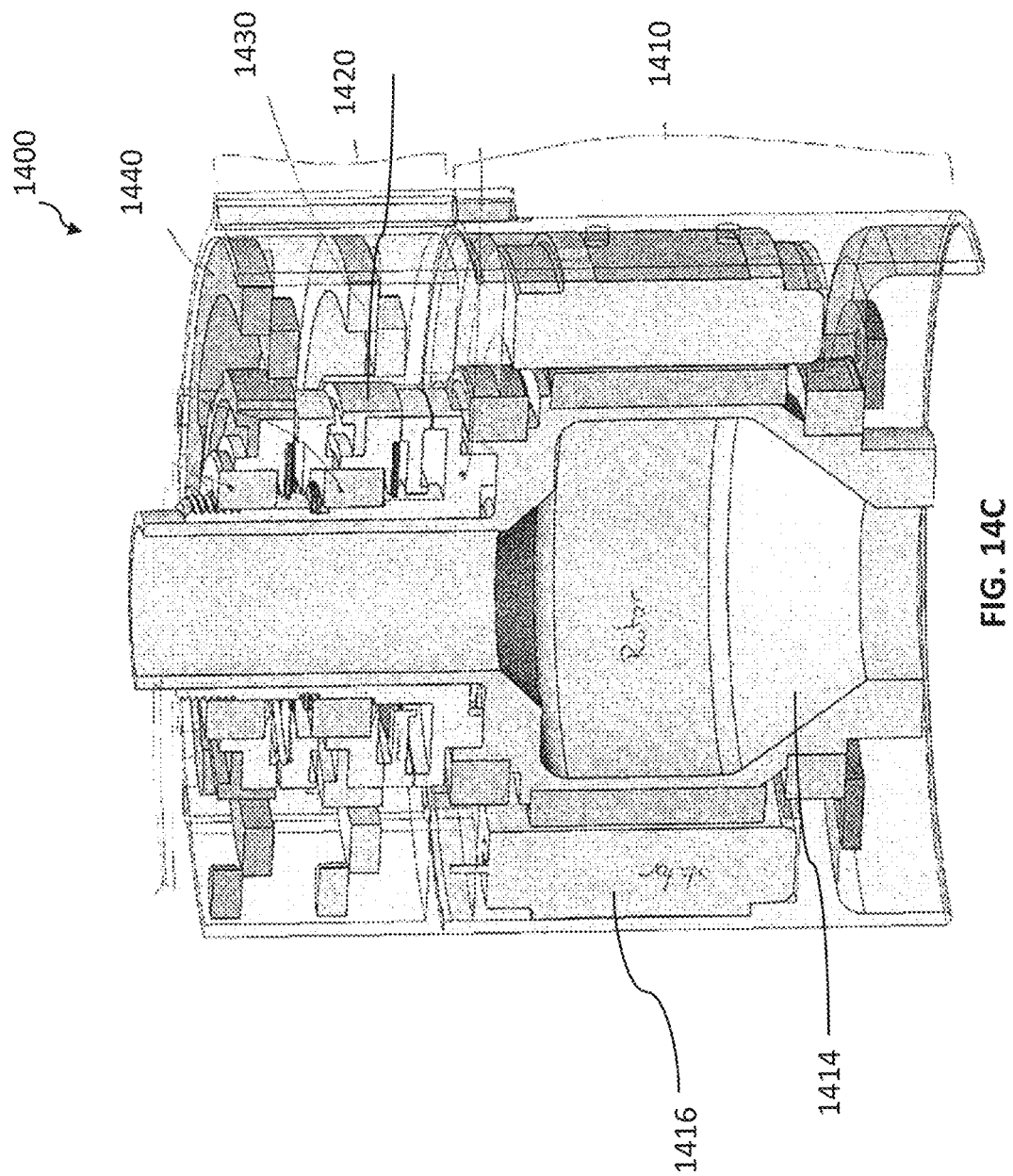
FIG. 14C is a detailed longitudinal cross-sectional view of the brake depicted in FIGS. 14A and 14B.

In the event of a power failure or system fault, the first ratchet brake assembly 1430 may engage its respective friction pad and cause the rotor to stop, as described above. Additionally, the second ratchet brake assembly 1440 may further engage its respective friction pad and provide supplemental force (to cooperate with the first ratchet brake assembly 1430 to stop the rotor, or to help maintain the static position of the rotor after it is already stopped). If the rotor needs to be movable after the first ratchet brake assembly stops the rotor (e.g., for manually reposing the robotic arm, backdriving, etc.), the first ratchet brake assembly 1430 may disengage from the stopped rotor (e.g., deactivating and re-engaging its magnetic latch), leaving the second ratchet brake assembly 1440 engaged. Since the second ratchet brake assembly 1440 has a lower torque, it may be overcome with manual force. Furthermore, although FIGS. 14B and 14C depict the second ratchet brake assembly (clutch brake) as being more distal relative to the rotor than the first ratchet brake assembly (arresting brake), alternatively the first ratchet brake assembly (arresting brake) may be more distal than the second ratchet brake assembly (clutch brake).

FIGS. 15A-15F illustrate another variation of a safety brake, which may be a bi-stable brake. In this variation, the safety brake 1500 may include at least one brake band arranged around the rotor of a motor. In the event of a power loss or other similar failure, the secondary actuator induces tightening of the brake bands, thereby causing the brake be in the "brake on" mode in which it provides a clamping force onto the rotor that frictionally stops the rotor from moving. Additionally, the brake band may be actuated by intentionally commanding the secondary actuator to release the brake band into the "brake on" mode. Alternatively, the brake 1500 may be a biased brake that is biased toward the "brake on" mode, where the brake 1500 actively requires power to maintain the brake in the "brake off" mode.

As shown in FIG. 15A, the safety brake 1500 includes one or more brake bands 1530 wrapped around or otherwise encircling the rotor 1514. The brake bands may be, for example, steel or other material with suitably high tensile strength (or alternatively, rubber or other elastomer which has high friction). In some variations, the joint module may include additional brake bands (e.g., third and fourth brake bands). As shown in FIGS. 15C and 15D, the bands are wrapped more than one full circumferential distance around the rotor, with each end connected to a band connector block 1564a or 1564b, such that when band connector blocks 1564a and 1564b are urged apart, the wrapped loop around the rotor tightens. This wrapping configuration permits the brake to have significant torque for stopping the rotor (even if the bands are made of a material with a low coefficient of friction), as a result of a "capstan" effect which is exponentially dependent on the total angle of wrap, thereby resulting in low force requirements for the secondary actuator as well as low friction requirements. For instance, the resulting braking torque may be governed by the capstan equation $T_{load}=T_{hold}*e^{\mu\varphi}$ where $T_{load}$ is the tension applied on the band, $T_{hold}$ is the resulting force exerted at the other end of the rotor, $\mu$ is the coefficient of friction between the band and the rotor, and $\varphi$ is the total angle swept by all turns of the band around the rotor (measured in radians).

The switching between the "brake on" and "brake off" modes is controlled by the secondary actuator 1550. For instance, the secondary actuator 1550 may include a bipolar stepper motor. The stepper motor may drive a lead screw, which causes the actuator nut 1560 to move linearly in a direction orthogonal to the plane of the brake bands 1530 and 1540. The actuator nut 1560 is coupled to the flex linkage 1562, which is configured to pull together and push apart the band connector blocks 1564a and 1564b. As shown in FIG. 15E, when the secondary actuator 1550 actively pushes forward the actuator nut 1550 and causes flex linkage 1562 to pull together the band connector blocks 1564a and 1564b, the brake bands are radially expanded in the "brake off" mode. In contrast, as shown in FIG. 15F, when the secondary actuator 1550 pulls back the actuator nut 1550, the flex linkage 1562 pushes apart the band connector blocks and the brake bands tighten in the "brake on" mode. Furthermore, the secondary actuator assembly may include a torsion spring 1570 configured to urge or somewhat bias the actuator nut 1550 toward the configuration for the "brake on" mode. Accordingly, the energy required to engage of the brake is in part provided by the torsion spring 1570, and compared to the torque needed to disengage the brake, the stepper motor can be driven with lower torque (and at higher speed, for quicker reaction to power loss or system failure) to engage the brake.

Figure 15B:
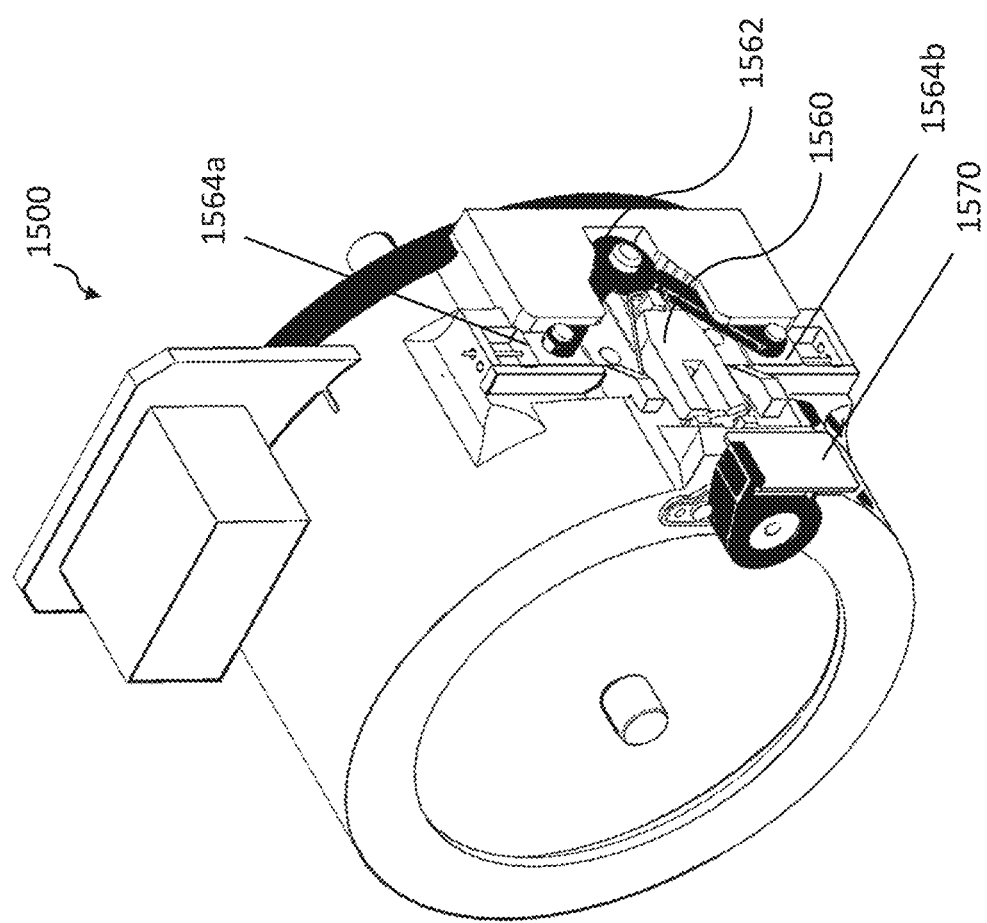
Figure 15F:
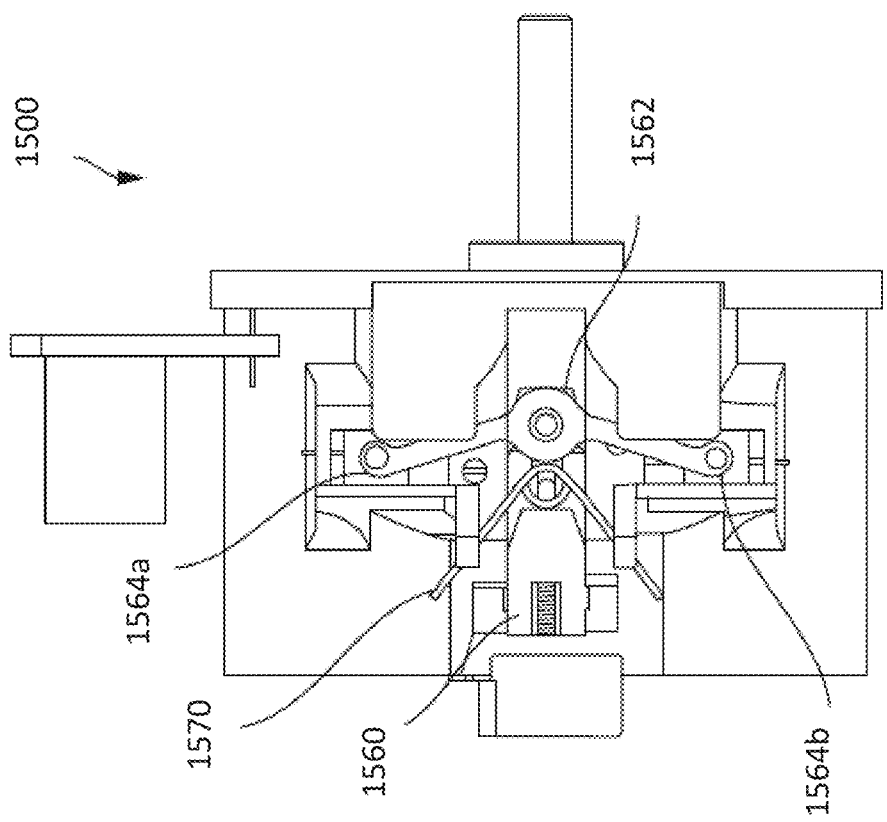
FIGS. 15E and 15F are side views of the brake depicted in FIGS. 15A and 15B, in a "brake off" mode and a "brake on" mode, respectively.
Figure 15E:
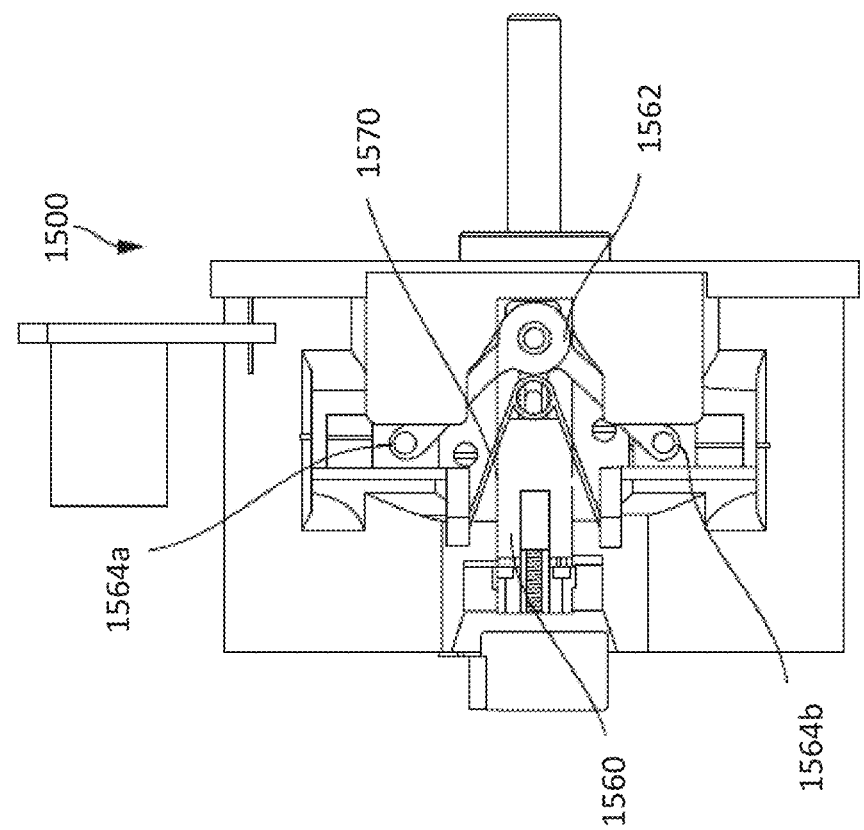
Figure 15G:
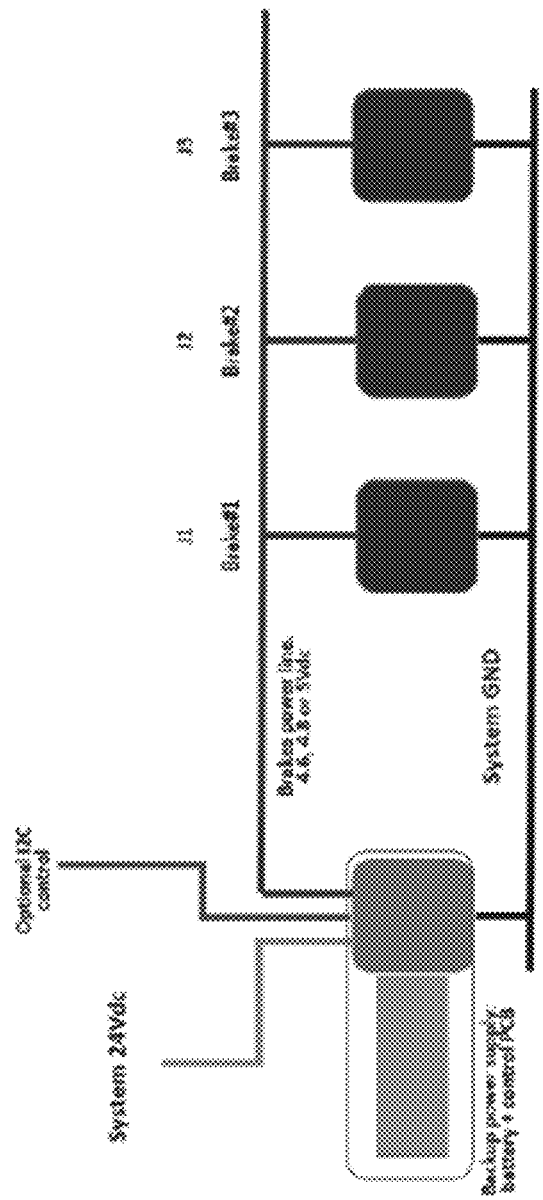
FIGS. 15G and 15H are exemplary control diagrams for controlling the brake depicted in FIGS. 15A and 15B.
Figure 15H:
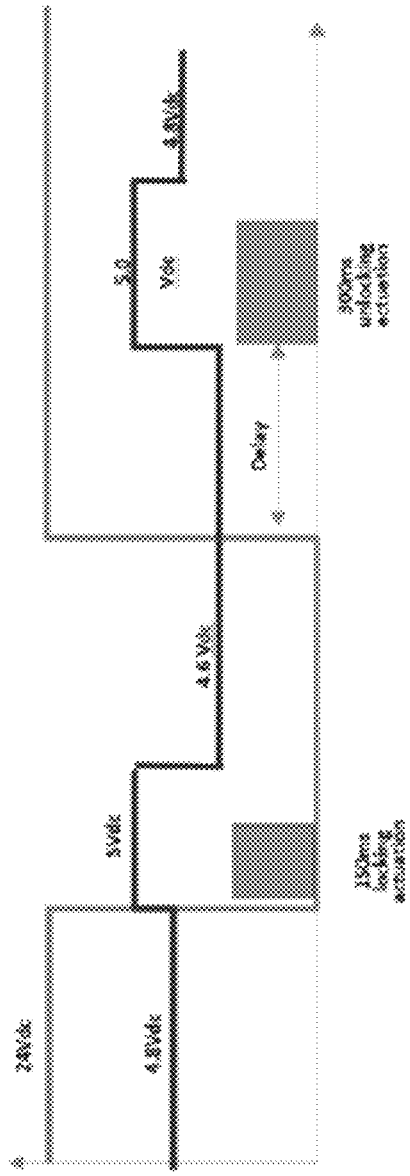

The secondary actuator 1550 may be controlled by a PCB 1570 as shown in FIG. 15B, where the PCB 1570 may include various electronic components such as a microprocessor for generating the stepper motor driving signals, a motor driver integrated circuit, and at least one backup battery (e.g., lithium ion) for powering actuation of the stepper motor in the event of system power failure. The backup battery may be automatically charged while the robotic arm system is powered, such that the backup battery always has some power in the event of robotic arm system loss. Driving signals sent to the stepper motor may cause the stepper motor to rotate in one direction (corresponding to "brake off") or the opposite direction (corresponding to "brake on"). For instance, in one exemplary embodiment as illustrated with the aid of FIGS. 15G and 15H, the PCB 1570 may be designed such that upon a system power loss (e.g., system power of about 24V suddenly drops to about zero), the backup battery automatically causes the power supply line to the secondary actuator to jump to a threshold power level (e.g., from about 4.8V to about 5V), thereby automatically triggering actuation to the "brake on" mode. Upon a system power restoration (e.g., system power supply is again about 24V), the secondary actuator may then disengage the brake. In some variations, before disengaging the brake, the secondary actuator may wait for a delay time (e.g., some number of milliseconds), which may allow the joint module actuator drivers to re-take control. Additionally or alternatively, the PCB 1570 may have a switch input to activate, on command, the "brake on" or "brake on" actions. Additionally or alternatively, the PCB 1570 may further include electronics for monitoring power supply and comparing power to a trigger threshold, similar to that described above with respect to secondary actuator 1000.

Touchpoints and Other User Interface Elements

Figure 16D:
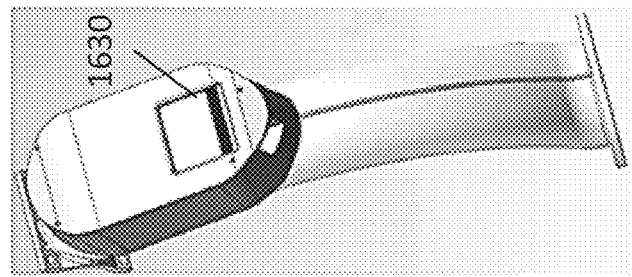
FIG. 16D is an exemplary variation of a display screen on the robotic arm for communicating information to a user.
Figure 16C:
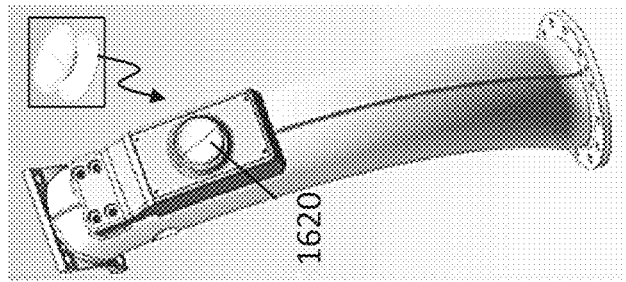
FIGS. 16A-16C are exemplary variations of touchpoints on the robotic arm.
Figure 16B:
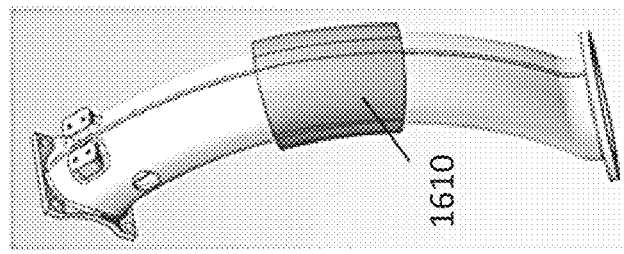
Figure 16A:
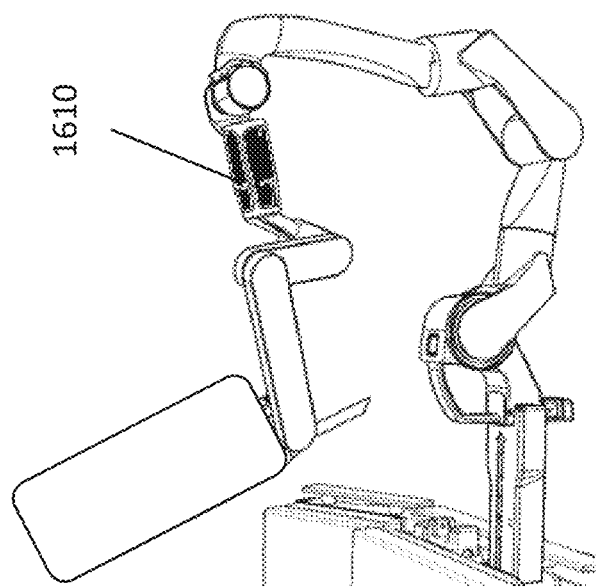

In some variations, as shown in FIGS. 16A-16C, the robotic arm may include a number of "touchpoints" which are regions of the arm configured to receive specific user interactions. A touchpoint may be in electrical communication with a control system that receives commands received at the touchpoint and provides actuation to one or more joint modules (and/or outputs other suitable commands) based on the received touchpoint commands. Additionally or alternatively, a touchpoint may be directly coupled a portion of the robotic arm for controlling an aspect of that arm (e.g., in direct communication with a joint module actuator for controlling the associated joint). For example, at least one of the robotic arm links may include a directional pad (e.g., cross-shaped D-pad, set of up-down-left-right buttons, etc.), which may be used, for example, for controlling desired arm movements when the robotic arm is operating in the repositioning mode (described further below). Other features, such as a handle, joystick, straps, a button switch, a capacitive sensor (e.g., tilting capacitive sensor, capacitive scroll, etc.), a mechanical scroll, a pressure sensor, force resistive sensor, and/or camera, etc. may additionally or alternatively be used to provide user interaction points for manually manipulating the robotic arm. For example, as shown in FIGS. 16A and 16B, the robotic arm may include a module 1610 for capacitive sensing, pressure sensing, and/or force sensing. As another example, as shown in FIG. 16C, the robotic arm may include a tilting dish-style cap 1620. In other variations, one or more of the touchpoints for manipulating the robotic arm may be located elsewhere in the system, such as a button on the instrument driver.

One or more touchpoints may be configured to receive manual input indicating user selection of a particular control mode (e.g., any of the control modes described further below). In some variations, a force resistive sensor may also offer positional information, such that a control mode may be toggled on/off in relation to location and/or orientation of the force. Additionally or alternatively, other force and/or torque sensors may be used to prove information to supplement inputs into the touchpoint control mechanisms. The user manipulation of these touchpoints may result in either an analog signal or digital signal (a threshold value may be defined in order to identify whether an analog signal represents an affirmative selection or input).

Different timing and combinations of manipulations of the touchpoints may be implemented. For example, one or more control modes may be selected upon a "press and hold" interaction (e.g., the control mode lasts as long as a pressure sensor or capacitive sensor detects sufficient force or presence of user contact on the touchpoint). As another example, one or more control modes may be selected and/or subsequently deselected upon a single contact or sufficient force (or contact lasting a predetermined threshold duration or force above a predetermined threshold of force).

Additionally, the robotic arm may include a number of electronics configured to provide the user with information about the robotic arm and/or instrument driver. For example, the robotic arm may include a speaker that provides auditory indications of operational status of the arm and/or instrument driver. As another example, the robotic arm may include one or more indicator lights (e.g., LEDs) on at least one of the robotic arm links. The indicator lights may communicate information through color and/or frequency or duration of illumination (e.g., blinking frequency). Such information may include, for example, control modes, control states, system fault, achievement or approximation of arm joint limits, directions, collision resolution, instrument change, instrument lifetime, instrument type, etc. For instance, a single indicator light may be green to indicate normal operational status, or yellow or red to indicate faults or other errors. As another example, some or all of the indicator lights may be illuminated in a particular color pattern to indicate instrument type (e.g., FIG. 17B). Additionally, the lighting pattern of a set of multiple indicator lights may communicate a code correlated to a specific kind of error (e.g., an on-off-on-on lighting pattern across four lights, such as that shown in FIG. 17C, may communicate a particular fault). The indicator lights may additionally or alternatively communicate information about other parts of the robotic-assisted surgical system. In one exemplary embodiment shown in FIGS. 17A-17C, the indicator lights may be part of a light module that communicates with users. As shown in FIG. 17A, the light ring module may include a plurality of LEDs (e.g., arranged in a ring, strip or other suitable pattern on a mount 1710), a light pipe bezel 1720 disposed over the plurality of LEDs to evenly diffuse light, and a microcontroller (e.g., on PCB) for controlling the illumination throughout the plurality of LEDs. Other lighting elements (e.g., laser diodes, etc.) may additionally or alternatively be included in the light module. The light pipe bezel may sit in a housing 1730 for an arm link, a portion of the instrument driver, or any other suitable location on or near the robotic arm. The light pipe bezel may, for example, include acrylic or any suitable light dissipating or propagating material. In some variations, a touchpoint, such as a joystick or button, may be positioned near the light module.

As another example, as shown in FIG. 16D, the robotic arm may include a display screen 1630 configured to textually and/or graphically display operational status, faults, other errors, and/or other suitable information. The indicator electronics may be mounted, for example, on the forearm link (or between the joint modules 134e and 134f shown in FIG. 1C), which may be a location at which the indicator electronics is typically at least partially visible to a user standing patient-side (e.g., next to a surgical table). In some variations, the display screen may include a touchscreen that is receptive to user input through a user interface (e.g., a GUI with menus, buttons, sliders, and/or other suitable controls for operating the robotic arm). The display screen may include any suitable screen, such as an LCD and/or capacitive touch screen.

Furthermore, as shown in FIG. 1D, the robotic arm may include a fine positioning clutch 170, which, when engaged, is configured to substantially restrict or lock (or substantially restrict deviation from) at least a portion of the pose of the second arm segment 150 (spherical arm segment) while enabling the joint modules of the first arm segment 110 (Cartesian arm segment) to move. Restricting at least a portion of the pose of the second arm segment 150 may be accomplished, for instance, by sending current commands to some or all of the joint modules in the second arm segment 150 that maintain their respective rotational positions, even if the entire second arm segment 150 is relocated as a whole by reposing the first arm segment 110. This functionality may be useful, for example, while docking the robotic arm to the cannula located in a port in the patient, so as to provide a fine positioning capability (i.e., facilitating small movements of the arm in response to user positioning guidance). In one exemplary embodiment, when the fine positioning clutch 170 is engaged, only the seventh joint module 134g in the spherical arm is substantially restricted (e.g., limited to movement within 10 degrees, within 5 degrees, or within 2 degrees, etc. in one or both directions relative to a reference locking position corresponding to when the clutch 170 is engaged) or locked (e.g., limited to substantially no movement relative to the reference locking position), while the other joint modules in the arm (e.g., first, second, third, fourth, fifth, and sixth joint modules) may be actuated to move without restriction. In another exemplary embodiment, when the fine positioning clutch 170 is engaged, both the sixth joint module 134f and/or seventh joint module 134g are substantially restricted or locked, while the joint modules in the first arm segment 110 may be actuated to move without restriction. Other combinations of restricted and/or locked joint modules and movable joint modules may be possible upon engagement of the fine positioning clutch. In some variations, the fine positioning clutch 170 may be located on the second arm segment 150, such as on the pitch linkage assembly 156 or another suitable location near the instrument driver, where the fine positioning clutch 170 may be easily accessible by a user standing near the port in the patient.

The fine positioning clutch 170 may include any suitable mechanism. For example, any of the touchpoints described above may operate as a fine positioning clutch. In some control modes of the robotic arm, the fine positioning clutch 170 may be biased toward the "disengage" mode so as to enable changing the pose of the entire robotic arm by default, and to restrict movement of the spherical arm only if the fine positioning clutch 170 is engaged. Additionally or alternatively, in some control modes such as in one variation of a docking mode, the fine positioning clutch 170 may be biased toward the "engage" mode so as to enable changing the pose of only the first arm segment 110 unless the fine positioning clutch 170 is disengaged. Furthermore, in some variations, the robotic arm 100 may include one or more other clutches that similarly lock one set of links in the current pose while enabling relative movement among another set of links, in any suitable combination.

Controller

Figure 18:
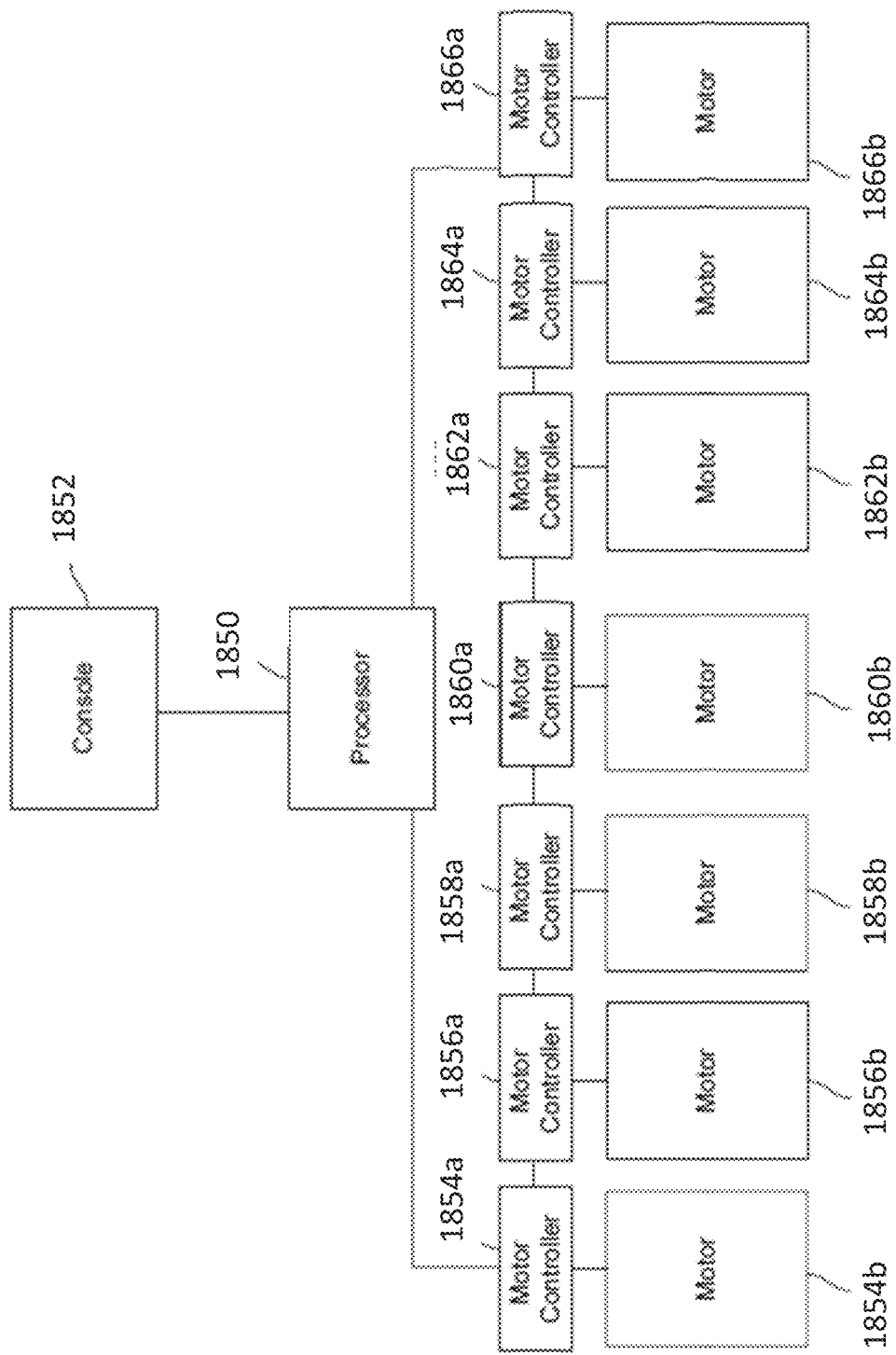
FIG. 18 is an overview schematic of an exemplary control system setup for controlling actuation of the joint modules of one variation of a robotic arm.

A robotic-assisted surgical system may include a control system that governs actions of the robotic arm (or multiple robotic arms, if the robotic-assisted surgical system includes more than one robotic arm). As shown in FIG. 18, the control system may include one or more processors 1850 (e.g., a microprocessor, microcontroller, application-specific integrated circuit, field programmable gate array, and/or other logic circuitry). The processor 1850, which may be physically located on the robotic arm itself, in a cart-carried unit, or other suitable structure, may be communicatively linked to a console (e.g., user interface). The control system may further include a set of multiple motor controllers (e.g., 1854a, 1856a, 1858a, 1860a, 1862a, 1864a, and 1866a), each of which is communicatively coupled to the processor 1850 and dedicated to control and operate at least one actuator in a respective joint module in the robotic arm (e.g., 1854b, 1856b, 1858b, 1860b, 1862b, 1864b, and 1866b).

Signals from the motor controller may be communicated to the actuators through wired connections bundled (e.g., in a wire harness) and passing within the internal volumes of the arm links and joint modules of the robotic arm. In some variations, the wired connections may be bundled together, such as in a wire harness. Furthermore, the physical layer of the networking hardware may be designed to reduce electrical interference caused by switching transients or sudden bursts of energy generated by motor drivers when they actuate the joint modules. For instance, the physical layer can include RS485-type transceivers, opto-isolated, and/or transformer-coupled interfaces to reduce such interference.

In some variations, it may be desirable to reduce the number of total wires inside the robotic arm, which would reduce the profile of the wire bundle or harness and simplify the routing of the wires through the links and moving joint modules. For example, the wiring connections may be arranged in a daisy chain ring configuration, in which the wiring for communication to and from a node (e.g., actuator or sensor) is reduced to one wire pair going into the node and another wire pair going out of the node. Furthermore, the daisy chain ring configuration of the wiring inside the robotic arm may be extended throughout the rest of the robotic-assisted surgical system (e.g., other robotic arms). As a result, the extension of the daisy chain ring configuration may, for example, reduce time lags in the exchange of data (e.g., command and feedback information) between the nodes and the control system. The daisy chain ring configuration may also distribute timing information that may be used to phase lock or synchronize all actuator nodes to the control system, which helps ensure that feedback information from all actuator nodes is been generated synchronously, thereby enabling more precise control loops for governing behavior of the one or more robotic arms.

Figure 19:
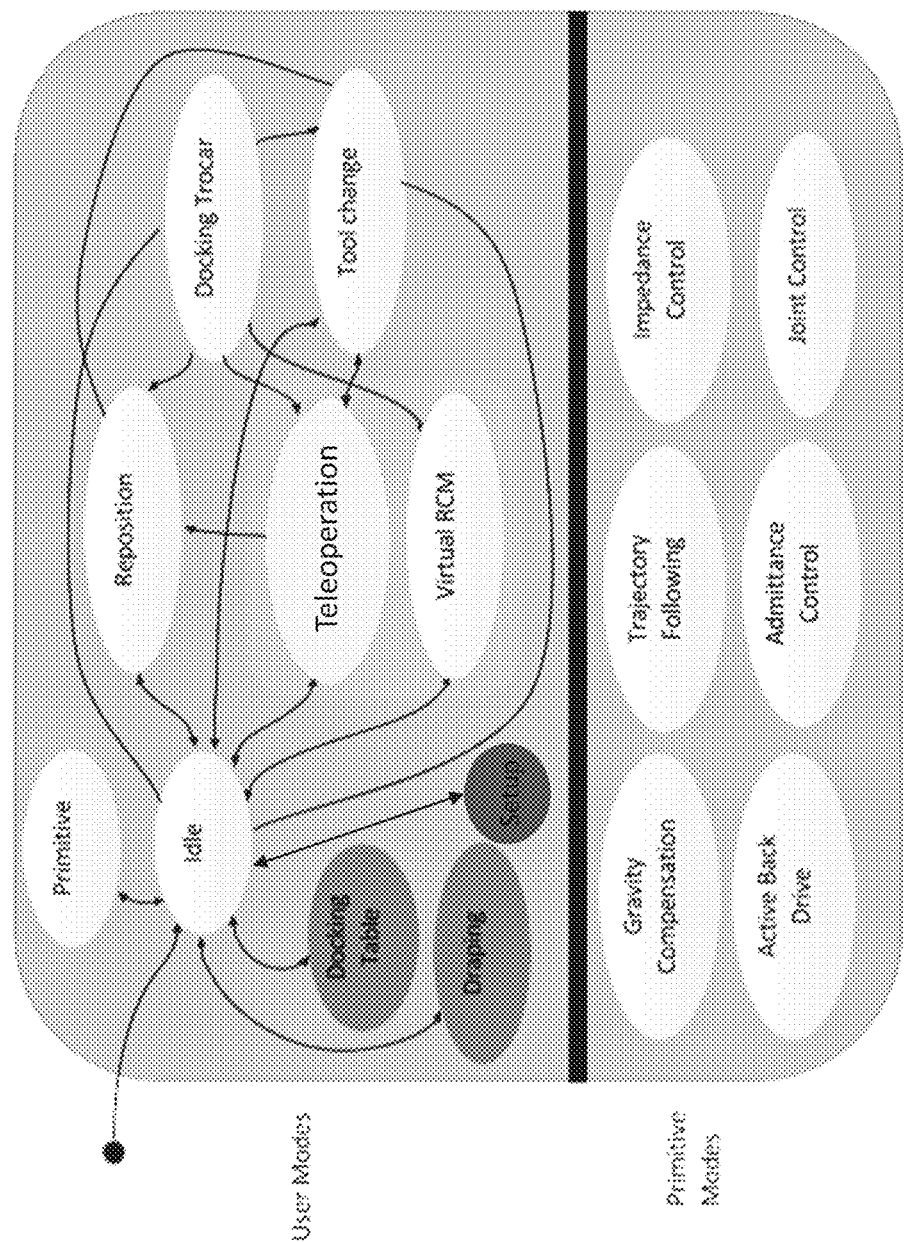
FIG. 19 is a state diagram summarizing primitive modes and user modes for one variation of a control system for a robotic arm.

As shown in FIG. 19, the control system may be configured to actuate at least one joint module based on one or more control modes. For example, a control mode may be classified as a primitive mode (which governs the underlying behavior for actuation of at least one joint module) or as a user mode (which governs higher level, task-specific behavior and may utilize one or more primitive modes). In some variations, a user may select a particular control mode through a user interface device (e.g., selecting a particular mode from an operation command list) or by activating buttons, touchscreens, or other touchpoint surface such as those described above on the surface of the robotic arm. Upon a user engaging a particular touchpoint surface, the switching between the various control modes may, for example, be handled by a state machine/controller.

Primitive Modes

In some variations, a primitive mode may be the smallest functional block that enables the robotic arm to carry out a particular task (e.g., actuate a joint module to increase or decrease the angle between arm links on either side of the joint module). As shown in FIG. 19, one example of a primitive control mode is a joint command mode, which allows a user to directly control a single joint module actuator individually, and/or multiple joint module actuators collectively. In the joint command mode, the robotic arm may be commanded joint-by-joint. The commands are direct or "pass through," in that outputs are the same as inputs. For instance, the inputs/outputs of the control system include joint module indices (e.g., index defining which joint module is associated with the command), an indication of the commanded mode (defining whether commands are to control the current or power to the one or more actuators in the joint module, the rotational position of the one or more actuators in the joint module, the rotational velocity of the one or more actuators in the joint module, etc.), and an indication of the reference command (values for the commanded current, position, velocity, etc.). In some variations, the joint command mode may include some error handling steps on the joint module and/or actuator level. For instance, the joint command mode may include a check that the joint command will not cause the joint module to exceed its physical limit, and/or a check that the joint command will not exceed the current limits of the one or more actuators. In some variations, the joint command mode may, for example, be used for system tuning and testing.

As shown in FIG. 19, another example of a primitive control mode is gravity compensation mode, in which the robotic arm holds itself in a particular pose (i.e., particular position and orientation of the links and joint modules) without drifting downward due to gravity. In gravity compensation mode, the control system determines the gravitational force acting on at least a portion of the links in the robotic arm. In response, the control system actuates at least one joint module to counteract the determined gravitational force such that the robotic arm can maintain the current pose. To determine the gravitational force, the controller may perform calculations based on measured joint angles between adjacent links, known kinematic and/or dynamic properties of the robotic arm and instrument driver, and/or known characteristics of the actuator (e.g., gear ratio, motor torque constants), etc. Furthermore, the robotic arm may include at least one accelerometer or other suitable sensor configured to determine the direction of the applied gravitational force on the arm. Based on these calculations, the controller may algorithmically determine what force at each joint module is needed to compensate for gravitational force acting on that joint module. For instance, the controller may utilize a forward kinematic algorithm, an inverse dynamic algorithm, or any suitable algorithm. The controller may then generate a set of commands to provide the actuators in the joint modules with appropriate level of current which holds the robotic arm in the same pose. The gravity compensation mode may, for example, be used alone or in combination with other modes in user modes described below, such as docking mode, draping mode, setup mode, and/or instrument change mode (e.g., coupling a surgical instrument to the instrument holder, swapping an existing surgical instrument in the instrument holder with a new surgical instrument, etc.).

As shown in FIG. 19, another example of a primitive control mode is friction compensation mode, or active back-drive mode. Often, a user may want to directly manipulate (e.g., pull or push) one or more of the arm links to arrange the robotic arm in a particular pose. These actions back-drive the actuators of the robotic arm. However, due to friction caused by mechanical aspects such as high gear ratios in the joint modules, the user must apply a significant amount of force in order to overcome the friction and successfully move the robotic arm. To address this, the friction compensation mode enables the robotic arm to assist a user in moving at least a portion of the robotic arm, by actively back-driving appropriate joint modules in the direction needed to achieve the pose desired by the user. As a result, the user may manually manipulate the robotic arm with less perceived friction or with an apparent "lightweight" feel. In some variations, the controller may also incorporate pre-defined parameters (e.g., duration of a force) to help distinguish between movement that is accidental (e.g., a brief bump of an arm) and a sudden intended shift in arm position, then correct or reestablish arm position in the event a movement is determined to be accidental. In friction compensation mode, the control system determines the presence and direction of a user-applied force acting on at least one joint module (either directly or indirectly as the result of force on one or more arm links) to back-drive the actuator in that joint module. In response, the control system actuates the joint module in the same direction as the user-applied force to help the user overcome static or dynamic friction. To determine the presence, magnitude, and direction of the user-applied force, the control system may monitor the velocity and/or position of the joint modules or robotic links (e.g., with force or torque sensors, accelerometers, etc.). Additionally, when in friction compensation mode, the control system may send a dithering current signal to (e.g., a sine wave or square wave centered at zero, with frequency of about 0.5 Hz-1.0 Hz or other suitable frequency, and with amplitude within the friction band in both directions) one or more joint modules, such that the joint modules are primed to nearly, but not quite, overcome friction in either actuator direction. In response to determining the presence and direction of user-applied force, the control system may then generate a set of commands to provide the actuators in the joint modules with appropriate level of current to more responsively overcome friction. The friction compensation mode may, for example, be used alone or in combination with other modes during docking, instrument change, etc.

As shown in FIG. 19, another example of a primitive control mode is trajectory following mode, in which the robotic arm may move to follow a sequence of one or more Cartesian trajectory commands. Trajectory commands may include, for example, velocity commands (framed in terms of linear and/or angular movement) or target pose commands (framed in terms of end objective position and orientation of the links and joint modules, such as a template pose for a particular kind of surgical procedure). If the command is a target pose that requires a number of link movements to transition from a current pose to the target pose, then the control system may generate a trajectory (defining the necessary link movements). If the command relates to a target pose that is the same as the current pose, then the control system may generate trajectory commands effectively resulting in a commanded "hold" position. For instance, the trajectory may be based on inputs including: commanded velocities or poses (e.g., transformation matrix, rotation matrix, 3D vector, 6D vector, etc.), the arm links to be controlled, measured joint parameters (angles, velocities, accelerations, etc.), tool parameters (type, weight, size, etc.), and environmental parameters (e.g., predefined regions which the arm link is barred or forbidden from entering, etc.). The control system may then use one or more algorithms to generate the outputs of commanded joint parameters (position, velocity, acceleration, etc.) to the firmware and/or commanded motor currents as current feedforward to the firmware. Suitable algorithms for determining these output commands include algorithms based on forward kinematics, inverse kinematics, inverse dynamics, and/or collision avoidance (e.g., collision between arm links, between different instances of the robotic arm, between the arm and environment, etc.). The trajectory following mode may, for example, be used alone or in combination with other modes in user modes described below, such as docking table mode, a draping mode, a setup mode and/or instrument change mode.

As shown in FIG. 19, another example of a primitive control mode is an impedance control mode, which allows the robotic arm to be compliant to a virtual environment without using a force and/or torque sensor. Generally, impedance control modulates the mechanical impedance of a mechanical system. Mechanical impedance of a system is defined as the ratio of force output of the system to motion input to the system. By controlling the mechanical impedance of the system, one may control the amount of the system's resistance to environment-imposed external motions. For instance, the impedance control mode may use a spring and damper system to model the surrounding environment, where a spring constant defines the force output for a modeled spring, and a damping constant defines the force output for a given velocity input. In some variations, one application of the impedance control mode is the creation and use of a virtual fixture, or haptics, such that the robotic arm can complete an operation (i.e., movement) that is compliant with defined restrictions, such as the environment and/or one or more virtual, geometric constraints applied to the robotic arm. One exemplary type of a virtual fixture is a "forbidden region" virtual fixture, which prevents the arm from entering into a predefined space in the environment (e.g., for collision avoidance). Another exemplary type of a virtual fixture is a "guidance" virtual fixture, which provides a guided motion to the arm by geometrically constraining range of motion limits of the arm (e.g., constraining relative motion of arm links). Control techniques in the impedance control mode can be framed as controlling the joint space (controlling actuation of each joint module) and/or Cartesian space (controlling the arm location in space). Inputs to the control algorithm may include measured joint angles and/or velocities of one or more portions of the robotic arm, selected virtual fixture configuration, and location of a targeted control point on the robotic arm. The control system may then use one or more algorithms to generate commanded joint actuator parameters (required current/torque, etc.) and/or status of the compliance to the imposed constraints. Suitable algorithms for determining these output commands include algorithms based on forward kinematics, inverse kinematics, inverse dynamics, collision avoidance (e.g., collision between arm links, between different instances of the robotic arm, between the arm and environment, etc.), and/or virtual force rendering (with the use of a virtual model such as geometric shape, mass, spring-and-damper, etc.). The impedance control mode may, for example, be used alone or in combination with other modes during instrument change.

As shown in FIG. 19, another example of a primitive control mode is an admittance control mode, which allows the robot arm to respond to sensed user force according to a virtual model (e.g., virtual mass/inertia properties). For instance, in response to one or more force/torque sensors that measure user force directed on the robotic arm, the actual robotic arm may move in the same manner that the virtual arm model would if the user pushed/pulled on the virtual arm model in the same manner. In some variations, the user force is measured at least with torque sensors in one or more joint modules in the arm. In other variations, the user force is measured at least with a six DOF force/torque sensor on one or more links of the robotic arm (e.g., such as the six DOF sensor described above) or multiple sensors detecting six DOF in aggregate (e.g., two 3 DOF sensors). The control system may take as an input the actual force/torque sensor readings, the force/torque sensor transformations to map the actual robotic arm to the virtual model, the virtual model transformations to map parameters to a known reference frame of the robotic arm, other virtual model properties, and/or robotic arm and instrument driver kinematics. The control system may then use one or more algorithms to generate commands to joint module actuators for particular current, torque, joint positions, and/or other suitable joint module parameters, in order to cause the robotic arm to move according to the virtual mode. Suitable algorithms for determining these output commands include algorithms based on forward kinematics, inverse kinematics, inverse dynamics, collision avoidance, and/or forward dynamics for the virtual model. The admittance control mode may, for example, be used alone or in combination with other modes during port docking or instrument change.

User Modes

In some variations, user modes may be control modes that overlay on top of primitive modes, in that a user mode can incorporate one or more primitive modes described above. The user modes allow the user to physically interact with the robotic arm in a number of different ways during different phases of a surgical procedure (e.g., during pre-operation setup and testing, surgery, post-operation tear-down and storage). For instance, certain user modes allow the robotic arm to react in a certain way depending on a particular combination of incorporated primitive modes. Additionally, certain user modes may involve a predetermined sequence of automated movement steps designed to increase efficiency for a particular phase of the surgical procedure. Many user modes are mutually exclusive from one another and cannot be selected simultaneously, but some user modes (e.g., teleoperation mode and virtual RCM mode) may operate in parallel.

As shown in FIG. 19, one example of a user mode is an idling mode, in which the robotic arm may rest in a current arm pose or a default arm pose awaiting further commands or instruction. In one variation, the idling mode incorporates the trajectory following mode described above, defining the target pose as the same as the current pose, thereby resulting in a commanded "hold" position. In another variation, the idling mode additionally or alternatively incorporates the gravity compensation mode described above.

As shown in FIG. 19, another example of a user mode is a setup mode, in which robotic arm may transition from a first pose (e.g., folded configuration for storage and transport) to a default pose (e.g., at least partially extended) such as a default setup pose or a predetermined template pose for a particular type of surgical procedure. Additionally, the robotic arm may initialize itself by completing a predetermined checklist (e.g., safety and functionality checks) of action items. The movement to a default pose and/or the checklist completion may be at least partially automatic or autonomous. Readiness of the robotic arm for use may be confirmed by a user and/or supervisory control system. While the robotic arm is in the setup mode, users may perform various pre-operative tasks on the robotic arm, such as inspection (e.g., visually or manually), cleaning, draping, etc.

As shown in FIG. 19, another example of a user mode is a mounting mode, in which the robotic arm is connected to an operative platform (e.g., surgical table or cart) and/or initialized for setup. For instance, while being connected to the operative platform, the robotic arm may rest in a current arm pose (e.g., the default pose achieved at the end of the action sequence in the setup mode). Similar to the idling mode, the docking table mode may incorporate the trajectory following mode resulting in a commanded "hold position", and/or may incorporate the gravity compensation mode described above.

As shown in FIG. 19, another example of a user mode is a draping mode, in which the robotic arm facilitates the process in which sterile barriers are coupled to the robotic arm (to maintain a sterile barrier between the robotic arm and the surgical instrument). For example, in the draping mode, the robotic arm may automatically move itself to a pre-determined draping pose, such as extended away from the patient and closer to a surgical assistant, that improves access to regions requiring the attachment of sterile barriers (e.g., at the instrument attachment point on the instrument driver). The surgical assistant may, for instance, walk around the patient table to each of multiple robotic arms in the draping poses to sequentially attach the sterile barrier to each individual robotic arm. Alternatively, the multiple robotic arms may automatically move closer to the surgical assistant so that the surgical assistant may remain stationary, thereby improving setup efficiency. For instance, when the sterile draping on a first robotic arm is complete and a second robotic arm is ready to be similarly draped, the control system may move the first robotic arm away to another position and may move the second robotic arm closer to the surgical assistant (e.g., after using sensors to automatically detect sterile barrier attachment, and/or after a user command indicating that the draping is complete). Furthermore, during draping, the user may be able to adjust the shape and position of the robotic arm to adapt to specific circumstances, such as clutter in the room, size of the patient, and/or limited height of the surgical assistant performing draping. In some variations, the draping mode may incorporate the joint command mode and/or gravity compensation mode to control the robotic arm.

As shown in FIG. 19, another example of a user mode is a docking mode, in which the robotic arm facilitates the process in which the user attaches the robotic arm to a port (with cannula pre-inserted into the patient's body) on the patient. In order to perform minimally-invasive surgery, the distal end of the robotic arm is generally rigidly latched to the port using gross or coarse positioning and fine positioning steps. During gross positioning, the surgical assistant may manually guide the distal end of the robotic arm closer to the port (e.g., within about six inches, or other suitable distance to the port) by grabbing, pushing, pulling, or otherwise manually the arm directly (alternatively while grasping a handle, or by manipulating a joystick, D-pad, or other user interface touchpoint). During gross positioning, gravity compensation and/or friction compensation may be applied at the arm joints as described above. Furthermore, in some variations, in order to prevent accidental or inadvertent bumps from moving the arm undesirably, the user's manually applied force may be required to overcome a threshold virtual spring force before the user's force causes the arm to move. During fine positioning, the surgical assistant may further manually guide the distal end of the robotic arm to couple to the cannula inserted in the port. Fine positioning may be further enabled with the use of a fine positioning clutch 170 (e.g., located on the spherical arm 150, near the instrument driver as shown in FIG. 1D and described above), such as a trigger, button, switch, etc. Upon engagement of the fine positioning clutch 170, the linkages of the first arm segment (Cartesian arm segment) may move under user guidance similar to during gross positioning, while locking at least some of the joint modules of the linkages of the second arm segment (spherical arm segment) such that at least some of the linkages of the second arm segment do not move relative to one another. During these steps, the control system may operate the robotic arm in gravity compensation mode and/or friction compensation mode described above.

As shown in FIG. 19, another example of a user mode is a teleoperation mode, in which the robotic arm is remotely controlled by a user interface device during the surgical procedure. While in the teleoperation mode, typically the Cartesian arm segment may be fixed in space (thereby preserving the mechanical RCM and the corresponding range of motion of the end effector) and the motion of the end effector may be controlled by the spherical arm segment and the instrument driver. The teleoperation mode may incorporate the gravity compensation mode, the trajectory following mode, and/or impedance control mode described above. In some variations, the trajectory following mode and/or the impedance control mode may focus on collision avoidance (e.g., with other robotic arms) while the robotic arm is in teleoperation mode.

As shown in FIG. 19, another example of a user mode is repositioning mode, in which the user may move the robotic arm in a new pose without changing the end effector instrument position and orientation. This kind of repositioning is possible due to the redundant DOFs in the robotic arm. For instance, the distal end of the robotic arm may remain docked to the port (allowing the mechanical RCM and the instrument to remain fixed in space) while the robotic arm is moved around the instrument driver (e.g., switching between either the "low" or "high" arm position and the "flipped" arm position described above). In the repositioning mode, the control system knows where the instrument is located, and tracks arm movement as the user repositions the robotic arm so as to avoid collisions with the robotic arm. Alternatively, the robotic arm may disengage from the instrument while the instrument is still inserted in the patient, then the robotic arm may reposition and subsequently reengage the instrument. After the robotic arm settles into a new pose and reengages with the instrument, the control system may initiate a check to help ensure that the functionality and control of the instrument is behaving correctly. The repositioning mode may incorporate the gravity compensation mode, trajectory following mode, and/or impedance control mode described above.

As an illustrative example, when the robotic arm is in the repositioning mode, the entire robotic arm may operate with gravity compensation. At least part of the first segment of the robotic arm (e.g., at least a portion of the Cartesian arm segment) may be passive, with joint modules that are passively back-drivable. At least part of the second segment of the robotic arm (e.g., at least a portion of the spherical arm segment) may be active, with joint modules that are locked in an active "hold" position in trajectory following mode in order to maintain the RCM and end effector position/orientation. After the robotic arm receives a user force (e.g., push or pull) on the robotic arm, the user force is propagated to the passive joint modules and causes the passive joints to move generally in compliance with the user force, with some constraints (e.g., implemented through impedance control). In particular, certain features (e.g., the distal most end of the passive arm segment) may be constrained on the surface of a virtual fixture, such as a generally spherical surface, such that the passive arm segment can only move within the regions not forbidden by the virtual fixture. While the passive arm segment is moving, the joint modules in the active arm segment may be actively driven to maintain a substantially constant/stable instrument and RCM position and angle, despite the passive arm segment being pushed to a new location on the virtual spherical surface. As shown in FIG. 19, another example of a user mode is virtual RCM mode, in which the robotic arm establishes a virtual remote center of motion that is not coincident with the mechanical remote center of motion. The virtual remote center of motion is created as the result of software combined with mechanical design. Typically, during a surgical procedure, the mechanical RCM is preserved by fixing the pose of the Cartesian arm segment and moving the spherical arm segment (i.e., during teleoperation mode). However, in the virtual RCM mode, the mechanical RCM can move in order to create better physical clearance between the robotic arm and the patient, while maintaining the previous effective range of motion of the end effector at a virtual RCM. The virtual RCM is achieved by moving both the Cartesian arm segment and spherical arm segment, as the Cartesian arm segment creates the offset between the mechanical and virtual RCMs. In contrast to the mechanical RCM, the virtual RCM can dynamically change, such as during a surgical procedure or between different surgical procedures. In some variations, the virtual RCM mode may incorporate the gravity compensation mode and trajectory following mode, or alternatively may incorporate the gravity compensation mode and the impedance control mode.

In some instances, the virtual RCM may be compliant, in that rather than being constrained to a point, the virtual RCM may be constrained to a plane which is generally normal to the instrument shaft axis and intersects the instrument shaft axis at a specified height relative to the mechanical RCM. In such instances, the joints of the Cartesian arm operate in gravity compensation, active back drive, and/or impedance control modes such that the joints allow the arm to respond to forces in line with the virtual plane, but resist forces perpendicular to the plane. The joints of the spherical arm (e.g., J6 and J7) and the joints of the instrument driver are still in trajectory following mode, thereby allowing the user to optionally continue driving the instrument and performing surgery. This allows the robotic arm to naturally find the pivot point which creates a low amount of force on the patient's tissue, while preventing the instrument and cannula from being pulled or pushed into or out of the patient. Such a mode of operation may be useful, for example, during cases with large instrument ranges of motion (e.g., multi-quadrant procedures) in which only a single, fixed pivot point may not be ideal. Other cases, such as procedures for operating on overweight/obese patients with thicker tissue layers, and thoracic procedures in which the cannula and instrument pass between ribs, may also benefit from such a compliant virtual RCM mode. The compliant virtual RCM mode may be used in conjunction with teleoperation mode or it may be engaged by the user selectively and intermittently. This mode may also be useful during cases in which the patient table is tilted during the procedure, as it would allow the arm to compliantly follow any shifts in patient tissue that result from the shift of the table (e.g., from Trendelenburg to reverse Trendelenburg position).

As shown in FIG. 19, another example of a user mode is instrument change or instrument change mode, in which multiple joint modules of the robotic arm may act to move the surgical instrument in or out of the cannula (e.g. translation along instrument axis H) beyond the range of motion available by actuating solely the distal most joint module. By moving the surgical instrument further out of the cannula (for instance, with an actuated cannula latch mechanism, e.g. operated by a motor, so that the cannula may be detached without a user's manual direct assistance), the robotic arms may easily dock or change between cannulae and instruments. In some variations, the instrument change mode may additionally or alternatively allow automatic instrument change in which the control system commands automatically taking the instrument out of the cannula, changing end effector tips or instruments, and re-docking the robotic arm to the cannula. Various selected end effector tips may be arranged in a pre-defined order on a surface (e.g., table), such that the control system may locate and identify desired end-effector tips for an automatic instrument change operation. In some variations, the instrument change mode may incorporate gravity compensation mode and trajectory following mode.

Other user modes may be programmed into the control system that incorporate and combine aspects of the various control modes described above. For example, another example of a user mode is a post-operative mode which may be similar to the set-up mode, except some steps may occur in a different order (e.g., system check, followed by folding the robotic arm into a folded configuration for storage). The post-operative mode may also include triggering a complete power off cycle. Other potential modes include a servicing mode, cleaning mode (e.g., move the robotic arm into a fully extended pose to increase exposed surface area during cleaning or sterilization), inspection mode, parade or marketing mode (e.g., pre-programmed series of movements for demonstration poses), cycle testing mode, and/or any other suitable mode.

Software Updateability

In some variations, the robotic surgical system may further include one or more processors for governing operation of the robotic arm and/or other components (e.g., instrument driver). For example, the robotic surgical system may include a control console or control tower including one or more computers, or other suitable computer arrangement. For example, as shown in FIG. 18, a control console 1852 may be communicative coupled to the at least one processor 1850 that controls the motor controllers for one or more robotic arms.

The control console 1852 may include software that may be changed (e.g., upgraded) periodically or intermittently for altering control of the robotic arm and/or other components of the robotic surgical system (e.g. handheld user interface devices). Advantageously, for example, updating the software that controls operation of the robotic arm may enable different functionalities and characteristics of the robotic arm without swapping out actual hardware of the robotic arm. Furthermore, in some variations, the software (within a particular version of software, or among different versions of software) may be specific to a surgeon or other user operating the robotic surgical system, and/or otherwise customizable to a user.

A different version of software may, for example, provide newer versions of control modes and/or control algorithms. For example, a new version of software may provide a new gravity compensation mode that more accurately or more quickly (through a faster computational process, etc.) counteracts gravitational force acting upon the robotic arm. As another example, a new version of software may provide a new scheme (parameters, boundaries, impedance values, etc.) for a virtual RCM and/or virtual fixture.

As another example, a different version of software may provide a different set of template or predetermined poses for the robotic arm (e.g., different variations of a "low", "high", and/or "flipped" arm configurations described above).

In other examples, different versions of software may be patient-specific, patient-type specific, and/or surgical procedure-type specific, etc. For example, certain predetermined robotic arm poses or configurations may be more optimized for smaller patients (e.g., pediatric patients), while other robotic arm poses or configurations may be more optimized for larger patients.

As another example, different versions of software may provide newer versions of graphical user interfaces on a display, touchscreen, etc. through which a user may view characteristics of the robotic arm (e.g., control mode, operational errors or warnings, etc.), where the newer versions of the a graphical user interface may include changes to, for example, layout and content of a menu.

Software updates to the arm may be administered, for example, through transfer of a file from a storage medium (e.g., hard drive, flash drive, floppy disk, cloud storage), through a wired and/or wireless connection. Software updates for the console 1852 (or other controlling computer arrangement) may be pushed or pulled on a periodic basis (e.g., daily, weekly, biweekly, monthly, bimonthly, semi-annually, annually, etc.), such as from a preexisting storage medium or other source. Additionally or alternatively, software updates may be triggered based in response to a user input (e.g., user selection on a user interface to update software).

Sterilization

In some variations, sterilization of the robotic arm prior to use in a robotic-assisted surgical system may be desirable in order to reduce the likelihood of inadvertently transmitting bacteria and other pathogens to the patient. For example, the robotic arm may be sterilized and then covered (e.g., with a bag, wrap, or other suitably sealed covering) to maintain its sterile condition. As another example, the robotic arm may first be covered and then sterilized through the cover, which can then subsequently maintain the sterile condition of the robotic arm. A sterilized and bagged robotic arm may be subsequently handled with less concern for maintaining sterility throughout packaging, transport, etc. until removal in a sterile field of use (e.g., operating room). Suitable sterilization procedures may include, for example, treating the robotic arm with ultraviolet light, e-beam radiation, gamma rays, and/or gas. The robotic arm may additionally or alternatively be sterilized in an autoclave or through another suitable medical grade sterilization process (e.g., in a resterilization process after a single use).

In other variations, the robotic arm may be treated for general cleanliness, but not sterility. For example, the robotic arm may be wiped down for dust, dirt, and/or other visible foreign objects. Following such a cleaning procedure, the robotic arm may be bagged to maintain its generally clean state. For instance, the robotic arm may be covered with a bag, drape, tarp, or other covering to help protect the robotic arm from splashes and other dangers.

Other examples of systems for maintaining sterility of the robotic arm and other components are described in detail in U.S. Provisional Patent Application Ser. No. 62/436,957 titled "STERILE ADAPTERS WITH A SHIFTING PLATE FOR USE IN A ROBOTIC SURGICAL SYSTEM," U.S. Provisional Patent Application Ser. No. 62/436,965 titled "STERILE ADAPTER DRIVE DISKS FOR USE IN A ROBOTIC SURGICAL SYSTEM," U.S. Provisional Patent Application Ser. No. 62/436,974 titled "STERILE ADAPTERS WITH A TOOL SEAT FOR USE IN A ROBOTIC SURGICAL SYSTEM," and U.S. Provisional Patent Application Ser. No. 62/436,981 titled "DRAPE ATTACHMENT TO STERILE ADAPTERS FOR USE IN A ROBOTIC SURGICAL SYSTEM," each of which was filed Dec. 20, 2016 and is hereby incorporated in its entirety by this reference.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications, and variations are possible in view of the above teachings. The embodiments were chosen and described in order to best explain the principles of the invention and its practical applications, and they thereby enable others skilled in the art to best utilize the invention and various embodiments with various modifications and/or in various combinations as are suited to the particular use contemplated.

The invention claimed is:

1. A robotic surgical system, comprising:
   a robotic arm comprising:
      a first arm segment comprising a first plurality of links providing the robotic arm with at least five degrees of freedom; and
      a second arm segment comprising a second plurality of links providing the robotic arm with at least two degrees of freedom, wherein the second plurality of links comprises a roll link, a first link rotatable within a first plane and having a proximal end coupled to a distal end of the roll link, and a second link rotatable within a second plane and having a proximal end coupled to a distal end of the first link; and
   an instrument driver configured to hold a surgical instrument and rotate the surgical instrument around a remote center of motion, wherein the instrument driver is coupled to a distal end of the second link such that the instrument driver is not parallel to at least one of the first and second planes, and the second arm segment is configured to rotate the instrument driver around a roll axis about which the roll link is configured to rotate, and a pitch axis about which rotation is remotely controlled by the first link and the second link, and wherein the roll axis and the pitch axis are offset from each other and the remote center of motion.

2. The system of claim 1, wherein the robotic arm is foldable into a compact configuration in which the instrument driver is positioned between the roll link and at least one of the first and second links.

3. The system of claim 1, wherein at least a portion of the roll link is oriented along the roll axis and at least a portion of the instrument driver is angularly offset from the roll axis.

4. The system of claim 1, wherein the second arm segment is configured to move the surgical instrument within a generally spherical workspace, and wherein the first arm segment is configured to move the location of the spherical workspace.

5. The system of claim 1, wherein a first degree of freedom of the robotic arm is provided by rotation of the roll link relative to the first arm segment.

6. The system of claim 5, wherein rotation of the roll link relative to the first arm segment causes movement of the instrument driver in a roll direction.

7. The system of claim 5, wherein a second degree of freedom of the robotic arm is provided by synchronous rotation of the first and second links relative to the roll link.

8. The system of claim 7, wherein synchronous rotation of the first and second links causes movement of the instrument driver in a pitch direction.

9. The system of claim 1, wherein at least one of the roll axis and the pitch axis is offset by about 2 centimeters or less from the remote center of motion.

10. The system of claim 1, wherein the first and second links are different lengths.

11. The system of claim 10, wherein the first link is shorter than the second link.

12. The system of claim 1, wherein the first and second links are operatively coupled with a pulley arrangement.

13. The system of claim 1, wherein the robotic arm is coupled to a table.

14. A robotic surgical system, comprising:
   a robotic arm comprising a roll link, a first link rotatable within a first plane and having a proximal end coupled to a distal end of the roll link, and a second link rotatable within a second plane and having a proximal end coupled to a distal end of the first link; and
   an instrument driver configured to hold a surgical instrument and rotate the surgical instrument around a remote center of motion, wherein the instrument driver is coupled to a distal end of the second link such that the instrument driver is not parallel to at least one of the first and second planes, and the robotic arm is configured to rotate the instrument driver around a roll axis and a pitch axis, wherein the roll axis and the pitch axis are offset from each other, and wherein at least one of the roll axis and the pitch axis is offset by about 5 centimeters or less from the remote center of motion such that the robotic arm is foldable into a compact configuration.

15. The system of claim 14, wherein when in the compact configuration, the instrument driver is positioned between the roll link and at least one of the first and second links.

16. The system of claim 14, wherein at least a portion of the roll link is oriented along the roll axis and at least a portion of the instrument driver is angularly offset from the roll axis.

17. The system of claim 14, wherein the roll axis and the pitch axis are offset from the remote center of motion.

18. The system of claim 14, wherein at least one of the roll axis and the pitch axis is offset by about 2 centimeters or less from the remote center of motion.

19. The system of claim 18, wherein the robotic arm is coupled to a table.

20. A robotic surgical system, comprising:
a robotic arm comprising:
a first arm segment comprising a first plurality of links providing the robotic arm with at least five degrees of freedom; and
a second arm segment comprising a second plurality of links providing the robotic arm with at least two degrees of freedom, wherein he second plurality of links comprises a roll link, a first pitch link having a proximal end coupled to a distal end of the roll link, and a second pitch link having a proximal end coupled to a distal end of the first link; and
an instrument driver configured to hold a surgical instrument and configured to rotate the surgical instrument around a remote center of motion,
wherein the second arm segment is configured to rotate the instrument driver around a roll axis about which the roll link is operable to rotate and a pitch axis about which rotation is remotely controlled by the first pitch link and the second pitch link, and wherein the roll axis and the pitch axis are offset from each other and the remote center of motion.

21. The system of claim 20, wherein at least one of the roll axis and the pitch axis is offset by about 5 centimeters or less from the remote center of motion.

22. The system of claim 21, wherein at least one of the roll axis and the pitch axis is offset by about 2 centimeters or less from the remote center of motion.

23. The system of claim 21, wherein the roll axis and the pitch axis are offset by about 2 centimeters or less from the remote center of motion.

24. The system of claim 20, wherein the second arm segment is configured to move the surgical instrument within a generally spherical workspace, and wherein the first arm segment is configured to move the location of the spherical workspace.

25. The system of claim 20, wherein rotation of the roll link relative to the first arm segment causes movement of the instrument driver around the roll axis, and wherein synchronous rotation of the first and second pitch links causes movement of the instrument driver around the pitch axis.

26. The system of claim 25, wherein the robotic arm is coupled to a table.

* * * * *